US009056918B2

(12) United States Patent
Napper et al.

(10) Patent No.: US 9,056,918 B2
(45) Date of Patent: Jun. 16, 2015

(54) PRION EPITOPES AND METHODS OF USE THEREOF

(75) Inventors: Scott Napper, Saskatoon (CA); Peter Hedlin, Saskatoon (CA); Philip Griebel, Saskatoon (CA); Lorne Babiuk, Edmonton (CA); Neil Cashman, Vancouver (CA); Avijit Chakrabartty, Toronto (CA); Andrew Potter, Saskatoon (CA)

(73) Assignee: University of Saskatchewan, Saskatoon, Saskatchewan (CA)

( * ) Notice: Subject to any disclaimer, the term of this patent is extended or adjusted under 35 U.S.C. 154(b) by 437 days.

(21) Appl. No.: 12/386,906

(22) Filed: Apr. 23, 2009

(65) Prior Publication Data

US 2009/0280125 A1 Nov. 12, 2009

Related U.S. Application Data

(60) Provisional application No. 61/125,507, filed on Apr. 25, 2008.

(51) Int. Cl.

| | |
|---|---|
| ***A61K 39/00*** | (2006.01) |
| ***C07K 7/06*** | (2006.01) |
| ***C07K 7/08*** | (2006.01) |
| ***C07K 16/28*** | (2006.01) |
| ***C07K 14/47*** | (2006.01) |
| ***G01N 33/68*** | (2006.01) |

(52) U.S. Cl.
CPC ............. *C07K 14/47* (2013.01); *A61K 39/0007* (2013.01); *A61K 2039/6037* (2013.01); *C07K 7/06* (2013.01); *C07K 7/08* (2013.01); *C07K 16/2872* (2013.01); *G01N 33/6893* (2013.01); *G01N 2800/2828* (2013.01); *C07K 2317/34* (2013.01)

(58) Field of Classification Search
None
See application file for complete search history.

(56) References Cited

U.S. PATENT DOCUMENTS

| | | | | |
|---|---|---|---|---|
| 5,422,110 | A | 6/1995 | Potter et al. | |
| 5,476,657 | A | 12/1995 | Potter | |
| 5,723,129 | A | 3/1998 | Potter et al. | |
| 5,837,268 | A | 11/1998 | Potter et al. | |
| 5,969,126 | A | 10/1999 | Potter et al. | |
| 6,022,960 | A * | 2/2000 | Potter et al. | 536/23.1 |
| 7,041,807 | B1 | 5/2006 | Cashman | |
| 2002/0168377 | A1* | 11/2002 | Schaetzl | 424/185.1 |
| 2003/0091579 | A1* | 5/2003 | Manns et al. | 424/185.1 |
| 2004/0072236 | A1* | 4/2004 | Cashman et al. | 435/7.1 |
| 2005/0244895 | A1* | 11/2005 | Ebringer et al. | 435/7.2 |
| 2005/0255525 | A1* | 11/2005 | Bastian | 435/7.1 |
| 2006/0183156 | A1 | 8/2006 | Cashman et al. | |
| 2009/0047696 | A1* | 2/2009 | Caughey et al. | 435/15 |

FOREIGN PATENT DOCUMENTS

| | | |
|---|---|---|
| EP | 1251138 | 10/2002 |
| WO | WO 00/78344 | 12/2000 |
| WO | WO 03/040685 | 5/2003 |
| WO | WO 03/080665 | 10/2003 |

OTHER PUBLICATIONS

Enari, et al., "Scrapie Prion Protein Accumulation by Scrapie-Infected Neuroblastoma Cells Abrogated by Exposure to a Prion Protein Antibody," *PNAS USA* 98:9295-9299 (2001).
Highlander et al., "DNA Sequence of the *Pasteurella* Haemolytica Leukotoxin Gene Cluster," DNA 8:15-28 (1989).
Lo, "Molecular Characterization of Cytotoxins Produced by Haemophilus, Actinobacillus, *Pasteurella*," Can J Vet Res 54:S33-S35 (1990).
Paramithiotis, et al., "A Prion Protein Epitope Selective for the Pathologically Misfolded Conformation," *Nat Med* 9:893-899 (2003).
Peretz, et al., "Antibodies Inhibit Prion Propagation and Clear Cell Cultures of Prion Infectivity," *Nature* 412:739-743 (2001).
Strathdee, et al., "Extensive Homology Between the Leukotoxin of *Pasteurella* Haemolytica A1 and the Alpha-Hemolysin of *Escherichia coli," Infect Immun* 55:3233-3236 (1987).
Welch, "Pore-Forming Cytolysins of Gram-Negative Bacteria," *Mol Microbiol* 5:521-528 (1991).
White, et al., "Monoclonal Antibodies Inhibit Prion Replication and Delay the Development of Prion Disease," *Nature* 422:80-83 (2003).
Bainbridge, et al., "Multiple Antigenic Peptides Facilitate Generation of Anti-Prion Antibodies," *Clin Exp Immunol* 137:298-304 (2004).
Gregoire, et al., "Identification of Two Immunogenic Domains of the Prion Protein—PrP—Which Activate Class II-Restricted T Cells and Elicit Antibody Responses Against the Native Molecule," *J Leukocyte Biology* 76:125-134 (2004).
Hedlin, et al., "Design and Delivery of a Cryptic $PRP^{C}$ Epitope for Induction of $PRP^{SC}$-Specific Antibody Repsonses," Vaccine, 28:981-988 (2010).

* cited by examiner

*Primary Examiner* — S. Devi

(74) *Attorney, Agent, or Firm* — Roberta L. Robins; Robins Law Group

(57) ABSTRACT

Prion peptides comprising prion epitopes and fusions thereof, that display enhanced immunogenicity are described. Also described are methods of treating and diagnosing prion disease.

17 Claims, 29 Drawing Sheets

```
Sheep          1 mvkshigswilvlfvamwsdvglckkrpkpgggwntggsrypgqgspggnryppqg--------gggwgqphgggwgqphgggwgqphgggwgqphgggg
Bovine         1 mvkshigswilvlfvamwsdvglckkrpkpgggwntggsrypgqgspggnryppqggggwgqphgggwgqphgggwgqphgggwgqphgggwgqphgggg
Human          1 --manlgcwmlvlfvatwsdlglckkrpkp-ggwntggsrypgqgspggnryppqg--------gggwgqphgggwgqphgggwgqphgggwgqph-ggg
Mouse          1 --manlgywllalfvtmwtdvglckkrpkp-ggwntggsrypgqgspggnryppq---------ggtwgqphgggwgqphggswgqphggswgqph-ggg
Elk            1 mvkshigswilvlfvamwsdvglckkrpkpgggwntggsrypgqgspggnryppqg--------gggwgqphgggwgqphgggwgqphgggwgqphgggg
Mule Deer      1 mvkshigswilvlfvamwsdvglckkrpkpgggwntggsrypgqgspggnryppqg--------gggwgqphgggwgqphgggwgqphgggwgqphgggg
Whitetail Deer1 mvkshigswilvlfvamwsdvglckkrpkpgggwntggsrypgqgspggnryppqg--------gggwgqphgggwgqphgggwgqphgggwgqphgggg

Sheep         93 wgq-ggshsqwnkpskpktnmkhvagaaaagavvgglggymlgsamsrplihfgndyedryyrenmyrypnqvyyrpvdqysnqnnfvhdcvnitvkqht
Bovine       101 wgq-ggthgqwnkpskpktnmkhvagaaaagavvgglggymlgsamsrplihfgkdyedryyrenmhrypnqvyyrpvdqysnqnnfvhdcvnitvkeht
Human         89 wgqgggthsqwnkpskpktnmkhmagaaaagavvgglggyvlgsamsrpiihfgsdyedryyrenmhrypnqvyyrpmdeysnqnnfvhdcvnitikqht
Mouse         88 wgqgggthnqwnkpskpktnlkhvagaaaagavvgglggymlgsamsrpmihfgndwedryyrenmyrypnqvyyrpvdqysnqnnfvhdcvnitikqht
Elk           93 wgq-ggthsqwnkpskpktnmkhvagaaaagavvgglggymlgsamsrplihfgndyedryyrenmyrypnqvyyrpvdqynnqntfvhdcvnitvkqht
Mule Deer     93 wgq-ggthsqwnkpskpktnmkhvagaaaagavvgglggymlgsamsrplihfgndyedryyrenmyrypnqvyyrpvdqynnqntfvhdcvnitvkqht
Whitetail Deer93 wgq-ggthsqwnkpskpktnmkhvagaaaagavvgglggymlgsamsrplihfgndyedryyrenmyrypnqvyyrpvdqynnqntfvhdcvnitvkqht

Sheep         192 vttttkgenftetdikimervveqmcitqyqresqayy--qrgasvilfssppvillisfliflivg
Bovine        200 vttttkgenftetdikmmervveqmcitqyqresqayy--qrgasvilfssppvillisfliflivg
Human         189 vttttkgenftetdvkmmervveqmcitqyeresqayy--qrgssmvlfssppvillisfliflivg
Mouse         188 vttttkgenftetdvkmmervveqmcvtqyqkesqayydgrrssstvlfssppvillisfliflivg
Elk           192 vttttkgenftetdikmmervveqmcitqyqreseayy--qrgasvilfssppvillisfliflivg
Mule Deer     192 vttttkgenftetdikmmervveqmcitqyqresqayy--qrgasvilfssppvillisfliflivg
Whitetail Deer192 vttttkgenftetdikmmervveqmcitqyqresqayy--qrgasvilfssppvillisfliflivg
```

Fig. 1

```
        .       10        .       20        .       30        .       40        .       50        .       60        .       70        .       80        .       90
ATG GCT ACT GTT ATA GAT CTA AGC TTC CCA AAA ACT GGG GCA AAA AAA ATT ATC CTC TAT ATT CCC CAA AAT TAC CAA TAT GAT ACT GAA
TAC CGA TGA CAA TAT CTA GAT TCG AAG GGT TTT TGA CCC CGT TTT TTT TAA TAG GAG ATA TAA GGG GTT TTA ATG GTT ATA CTA TGA CTT
Met Ala Thr Val Ile Asp Leu Ser Phe Pro Lys Thr Gly Ala Lys Lys Ile Ile Leu Tyr Ile Pro Gln Asn Tyr Gln Tyr Asp Thr Glu>
---c---c---c---c---c---c---c---c---c---c----RECOMBINANT LEUKOTOXIN PEPTIDE_c---c---c---c---c---c---c---c---c---c---c--->
---a---a---VECTOR SEQUENCE_a---a---a-->

        .      100        .      110        .      120        .      130        .      140        .      150        .      160        .      170        .      180
CAA GGT AAT GGT TTA CAG GAT TTA GTC AAA GCG GCC GAA GAG TTG GGG ATT GAG GTA CAA AGA GAA GAA CGC AAT AAT ATT GCA ACA GCT
GTT CCA TTA CCA AAT GTC CTA AAT CAG TTT CGC CGG CTT CTC AAC CCC TAA CTC CAT GTT TCT CTT CTT GCG TTA TTA TAA CGT TGT CGA
Gln Gly Asn Gly Leu Gln Asp Leu Val Lys Ala Ala Glu Glu Leu Gly Ile Glu Val Gln Arg Glu Glu Arg Asn Asn Ile Ala Thr Ala>
---c---c---c---c---c---c---c---c---c---c----RECOMBINANT LEUKOTOXIN PEPTIDE_c---c---c---c---c---c---c---c---c---c---c--->

        .      190        .      200        .      210        .      220        .      230        .      240        .      250        .      260        .      270
CAA ACC AGT TTA GGC ACG ATT CAA ACC GCT ATT GGC TTA ACT GAG CGT GGC ATT GTG TTA TCC GCT CCA CAA ATT GAT AAA TTG CTA CAG
GTT TGG TCA AAT CCG TGC TAA GTT TGG CGA TAA CCG AAT TGA CTC GCA CCG TAA CAC AAT AGG CGA GGT GTT TAA CTA TTT AAC GAT GTC
Gln Thr Ser Leu Gly Thr Ile Gln Thr Ala Ile Gly Leu Thr Glu Arg Gly Ile Val Leu Ser Ala Pro Gln Ile Asp Lys Leu Leu Gln>
---c---c---c---c---c---c---c---c---c---c----RECOMBINANT LEUKOTOXIN PEPTIDE_c---c---c---c---c---c---c---c---c---c---c--->
```

FIG. 11A

```
                280             290             300             310             320             330             340             350             360
AAA ACT AAA GCA GGC CAA GCA TTA GGT TCT GCC GAA AGC ATT GTA CAA AAT GCA AAT AAA GCC AAA ACT GTA TTA TCT GGC ATT CAA TCT
TTT TGA TTT CGT CCG GTT CGT AAT CCA AGA CGG CTT TCG TAA CAT GTT TTA CGT TTA TTT CGG TTT TGA CAT AAT AGA CCG TAA GTT AGA
Lys Thr Lys Ala Gly Gln Ala Leu Gly Ser Ala Glu Ser Ile Val Gln Asn Ala Asn Lys Ala Lys Thr Val Leu Ser Gly Ile Gln Ser>
---C---C---C---C---C---C---C---C---C---C----RECOMBINANT LEUKOTOXIN PEPTIDE-C---C---C---C---C---C---C---C---C---C---C--->

                370             380             390             400             410             420             430             440             450
ATT TTA GGC TCA GTA TTG GCT GGA ATG GAT TTA GAT GAG GCC TTA CAG AAT AAC AGC AAC CAA CAT GCT CTT GCT AAA GCT GGC TTG GAG
TAA AAT CCG AGT CAT AAC CGA CCT TAC CTA AAT CTA CTC CGG AAT GTC TTA TTG TCG TTG GTT GTA CGA GAA CGA TTT CGA CCG AAC CTC
Ile Leu Gly Ser Val Leu Ala Gly Met Asp Leu Asp Glu Ala Leu Gln Asn Asn Ser Asn Gln His Ala Leu Ala Lys Ala Gly Leu Glu>
---C---C---C---C---C---C---C---C---C---C----RECOMBINANT LEUKOTOXIN PEPTIDE-C---C---C---C---C---C---C---C---C---C---C--->

                460             470             480             490             500             510             520             530             540
CTA ACA AAT TCA TTA ATT GAA AAT ATT GCT AAT TCA GTA AAA ACA CTT GAC GAA TTT GGT GAG CAA ATT AGT CAA TTT GGT TCA AAA CTA
GAT TGT TTA AGT AAT TAA CTT TTA TAA CGA TTA AGT CAT TTT TGT GAA CTG CTT AAA CCA CTC GTT TAA TCA GTT AAA CCA AGT TTT GAT
Leu Thr Asn Ser Leu Ile Glu Asn Ile Ala Asn Ser Val Lys Thr Leu Asp Glu Phe Gly Glu Gln Ile Ser Gln Phe Gly Ser Lys Leu>
---C---C---C---C---C---C---C---C---C---C----RECOMBINANT LEUKOTOXIN PEPTIDE-C---C---C---C---C---C---C---C---C---C---C--->

                550             560             570             580             590             600             610             620             630
CAA AAT ATC AAA GGC TTA GGG ACT TTA GGA GAC AAA CTC AAA AAT ATC GGT GGA CTT GAT AAA GCT GGC CTT GGT TTA GAT GTT ATC TCA
GTT TTA TAG TTT CCG AAT CCC TGA AAT CCT CTG TTT GAG TTT TTA TAG CCA CCT GAA CTA TTT CGA CCG GAA CCA AAT CTA CAA TAG AGT
Gln Asn Ile Lys Gly Leu Gly Thr Leu Gly Asp Lys Leu Lys Asn Ile Gly Gly Leu Asp Lys Ala Gly Leu Gly Leu Asp Val Ile Ser>
---C---C---C---C---C---C---C---C---C---C----RECOMBINANT LEUKOTOXIN PEPTIDE-C---C---C---C---C---C---C---C---C---C---C--->
```

FIG. 11B

```
                 640         650         660         670         680         690         700         710         720
       *           *           *           *           *           *           *           *           *           *
GGG CTA TTA TCG GGC GCA ACA GCT GCA CTT GTA CTT GCA GAT AAA AAT GCT TCA ACA GCT AAA AAA GTG GGT GCG GGT TTT GAA TTG GCA
CCC GAT AAT AGC CCG CGT TGT CGA CGT GAA CAT GAA CGT CTA TTT TTA CGA AGT TGT CGA TTT TTT CAC CCA CGC CCA AAA CTT AAC CGT
Gly Leu Leu Ser Gly Ala Thr Ala Ala Leu Val Leu Ala Asp Lys Asn Ala Ser Thr Ala Lys Lys Val Gly Ala Gly Phe Glu Leu Ala>
___C___C___C___C___C___C___C___C___C___C____RECOMBINANT LEUKOTOXIN PEPTIDE_C___C___C___C___C___C___C___C___C___C___C___>

                 730         740         750         760         770         780         790         800         810
       *           *           *           *           *           *           *           *           *           *
AAC CAA GTT GTT GGT AAT ATT ACC AAA GCC GTT TCT TCT TAC ATT TTA GCC CAA CGT GTT GCA GCA GGT TTA TCT TCA ACT GGG CCT GTG
TTG GTT CAA CAA CCA TTA TAA TGG TTT CGG CAA AGA AGA ATG TAA AAT CGG GTT GCA CAA CGT CGT CCA AAT AGA AGT TGA CCC GGA CAC
Asn Gln Val Val Gly Asn Ile Thr Lys Ala Val Ser Ser Tyr Ile Leu Ala Gln Arg Val Ala Ala Gly Leu Ser Ser Thr Gly Pro Val>
___C___C___C___C___C___C___C___C___C___C____RECOMBINANT LEUKOTOXIN PEPTIDE_C___C___C___C___C___C___C___C___C___C___C___>

                 820         830         840         850         860         870         880         890         900
       *           *           *           *           *           *           *           *           *           *
GCT GCT TTA ATT GCT TCT ACT GTT TCT CTT GCG ATT AGC CCA TTA GCA TTT GCC GGT ATT GCC GAT AAA TTT AAT CAT GCA AAA AGT TTA
CGA CGA AAT TAA CGA AGA TGA CAA AGA GAA CGC TAA TCG GGT AAT CGT AAA CGG CCA TAA CGG CTA TTT AAA TTA GTA CGT TTT TCA AAT
Ala Ala Leu Ile Ala Ser Thr Val Ser Leu Ala Ile Ser Pro Leu Ala Phe Ala Gly Ile Ala Asp Lys Phe Asn His Ala Lys Ser Leu>
___C___C___C___C___C___C___C___C___C___C____RECOMBINANT LEUKOTOXIN PEPTIDE_C___C___C___C___C___C___C___C___C___C___C___>
```

FIG. 11C

```
         910       920       930       940       950       960       970       980       990
     *    *    *    *    *    *    *    *    *    *    *    *    *    *    *    *    *    *
GAG AGT TAT GCC GAA CGC TTT AAA AAA TTA GGC TAT GAC GGA GAT AAT TTA TTA GCA GAA TAT CAG CGG GGA ACA GGG ACT ATT GAT GCA
CTC TCA ATA CGG CTT GCG AAA TTT TTT AAT CCG ATA CTG CCT CTA TTA AAT AAT CGT CTT ATA GTC GCC CCT TGT CCC TGA TAA CTA CGT
Glu Ser Tyr Ala Glu Arg Phe Lys Lys Leu Gly Tyr Asp Gly Asp Asn Leu Leu Ala Glu Tyr Gln Arg Gly Thr Gly Thr Ile Asp Ala>
___C___C___C___C___C___C___C___C___C___C____RECOMBINANT LEUKOTOXIN PEPTIDE_C___C___C___C___C___C___C___C___C___C___>

        1000      1010      1020      1030      1040      1050      1060      1070      1080
     *    *    *    *    *    *    *    *    *    *    *    *    *    *    *    *    *    *
TCG GTT ACT GCA ATT AAT ACC GCA TTG GCC GCT ATT GCT GGT GGT GTG TCT GCT GCT GCA GCC GGC TCG GTT ATT GCT TCA CCG ATT GCC
AGC CAA TGA CGT TAA TTA TGG CGT AAC CGG CGA TAA CGA CCA CCA CAC AGA CGA CGA CGT CGG CCG AGC CAA TAA CGA AGT GGC TAA CGG
Ser Val Thr Ala Ile Asn Thr Ala Leu Ala Ala Ile Ala Gly Gly Val Ser Ala Ala Ala Ala Gly Ser Val Ile Ala Ser Pro Ile Ala>
___C___C___C___C___C___C___C___C___C___C____RECOMBINANT LEUKOTOXIN PEPTIDE_C___C___C___C___C___C___C___C___C___C___>

        1090      1100      1110      1120      1130      1140      1150      1160      1170
     *    *    *    *    *    *    *    *    *    *    *    *    *    *    *    *    *    *
TTA TTA GTA TCT GGG ATT ACC GGT GTA ATT TCT ACG ATT CTG CAA TAT TCT AAA CAA GCA ATG TTT GAG CAC GTT GCA AAT AAA ATT CAT
AAT AAT CAT AGA CCC TAA TGG CCA CAT TAA AGA TGC TAA GAC GTT ATA AGA TTT GTT CGT TAC AAA CTC GTG CAA CGT TTA TTT TAA GTA
Leu Leu Val Ser Gly Ile Thr Gly Val Ile Ser Thr Ile Leu Gln Tyr Ser Lys Gln Ala Met Phe Glu His Val Ala Asn Lys Ile His>
___C___C___C___C___C___C___C___C___C___C____RECOMBINANT LEUKOTOXIN PEPTIDE_C___C___C___C___C___C___C___C___C___C___>

        1180      1190      1200      1210      1220      1230      1240      1250      1260
     *    *    *    *    *    *    *    *    *    *    *    *    *    *    *    *    *    *
AAC AAA ATT GTA GAA TGG GAA AAA AAT AAT CAC GGT AAG AAC TAC TTT GAA AAT GGT TAC GAT GCC CGT TAT CTT GCG AAT TTA CAA GAT
TTG TTT TAA CAT CTT ACC CTT TTT TTA TTA GTG CCA TTC TTG ATG AAA CTT TTA CCA ATG CTA CGG GCA ATA GAA CGC TTA AAT GTT CTA
Asn Lys Ile Val Glu Trp Glu Lys Asn Asn His Gly Lys Asn Tyr Phe Glu Asn Gly Tyr Asp Ala Arg Tyr Leu Ala Asn Leu Gln Asp>
___C___C___C___C___C___C___C___C___C___C____RECOMBINANT LEUKOTOXIN PEPTIDE_C___C___C___C___C___C___C___C___C___C___>
```

FIG. 11D

```
         1270        1280        1290        1300        1310        1320        1330        1340        1350
     *     *     *     *     *     *     *     *     *     *     *     *     *     *     *     *     *     *
AAT ATG AAA TTC TTA CTG AAC TTA AAC AAA GAG TTA CAG GCA GAA CGT GTC ATC GCT ATT ACT CAG CAG CAA TGG GAT AAC AAC ATT GGT
TTA TAC TTT AAG AAT GAC TTG AAT TTG TTT CTC AAT GTC CGT CTT GCA CAG TAG CGA TAA TGA GTC GTC GTT ACC CTA TTG TTG TAA CCA
Asn Met Lys Phe Leu Leu Asn Leu Asn Lys Glu Leu Gln Ala Glu Arg Val Ile Ala Ile Thr Gln Gln Gln Trp Asp Asn Asn Ile Gly>
___C___C___C___C___C___C___C___C___C___C____RECOMBINANT LEUKOTOXIN PEPTIDE_C___C___C___C___C___C___C___C___C___C___C___>

         1360        1370        1380        1390        1400        1410        1420        1430        1440
     *     *     *     *     *     *     *     *     *     *     *     *     *     *     *     *     *     *
GAT TTA GCT GGT ATT AGC CGT TTA GGT GAA AAA GTC CTT AGT GGT AAA GCC TAT GTG GAT GCG TTT GAA GAA GGC AAA CAC ATT AAA GCC
CTA AAT CGA CCA TAA TCG GCA AAT CCA CTT TTT CAG GAA TCA CCA TTT CGG ATA CAC CTA CGC AAA CTT CTT CCG TTT GTG TAA TTT CGG
Asp Leu Ala Gly Ile Ser Arg Leu Gly Glu Lys Val Leu Ser Gly Lys Ala Tyr Val Asp Ala Phe Glu Glu Gly Lys His Ile Lys Ala>
___C___C___C___C___C___C___C___C___C___C____RECOMBINANT LEUKOTOXIN PEPTIDE_C___C___C___C___C___C___C___C___C___C___C___>

         1450        1460        1470        1480        1490        1500        1510        1520        1530
     *     *     *     *     *     *     *     *     *     *     *     *     *     *     *     *     *     *
GAT AAA TTA GTA CAG TTG GAT TCG GCA AAC GGT ATT ATT GAT GTG AGT AAT TCG GGT AAA GCG AAA ACT CAG CAT ATC TTA TTC AGA ACG
CTA TTT AAT CAT GTC AAC CTA AGC CGT TTG CCA TAA TAA CTA CAC TCA TTA AGC CCA TTT CGC TTT TGA GTC GTA TAG AAT AAG TCT TGC
Asp Lys Leu Val Gln Leu Asp Ser Ala Asn Gly Ile Ile Asp Val Ser Asn Ser Gly Lys Ala Lys Thr Gln His Ile Leu Phe Arg Thr>
___C___C___C___C___C___C___C___C___C___C____RECOMBINANT LEUKOTOXIN PEPTIDE_C___C___C___C___C___C___C___C___C___C___C___>
```

FIG. 11E

```
     .  1540  .  1550  .  1560  .  1570  .  1580  .  1590  .  1600  .  1610  .  1620
CCA TTA TTG ACG CCG GGA ACA GAG CAT CGT GAA CGC GTA CAA ACA GGT AAA TAT GAA TAT ATT ACC AAG CTC AAT ATT AAC CGT GTA GAT
GGT AAT AAC TGC GGC CCT TGT CTC GTA GCA CTT GCG CAT GTT TGT CCA TTT ATA CTT ATA TAA TGG TTC GAG TTA TAA TTG GCA CAT CTA
Pro Leu Leu Thr Pro Gly Thr Glu His Arg Glu Arg Val Gln Thr Gly Lys Tyr Glu Tyr Ile Thr Lys Leu Asn Ile Asn Arg Val Asp>
___C___C___C___C___C___C___C___C___C___C____RECOMBINANT LEUKOTOXIN PEPTIDE_C___C___C___C___C___C___C___C___C___C___C___>

     .  1630  .  1640  .  1650  .  1660  .  1670  .  1680  .  1690  .  1700  .  1710
AGC TGG AAA ATT ACA GAT GGT GCA GCA AGT TCT ACC TTT GAT TTA ACT AAC GTT GTT CAG CGT ATT GGT ATT GAA TTA GAC AAT GCT GGA
TCG ACC TTT TAA TGT CTA CCA CGT CGT TCA AGA TGG AAA CTA AAT TGA TTG CAA CAA GTC GCA TAA CCA TAA CTT AAT CTG TTA CGA CCT
Ser Trp Lys Ile Thr Asp Gly Ala Ala Ser Ser Thr Phe Asp Leu Thr Asn Val Val Gln Arg Ile Gly Ile Glu Leu Asp Asn Ala Gly>
___C___C___C___C___C___C___C___C___C___C____RECOMBINANT LEUKOTOXIN PEPTIDE_C___C___C___C___C___C___C___C___C___C___C___>

     .  1720  .  1730  .  1740  .  1750  .  1760  .  1770  .  1780  .  1790  .  1800
AAT GTA ACT AAA ACC AAA GAA ACA AAA ATT ATT GCC AAA CTT GGT GAA GGT GAT GAC AAC GTA TTT GTT GGT TCT GGT ACG ACG GAA ATT
TTA CAT TGA TTT TGG TTT CTT TGT TTT TAA TAA CGG TTT GAA CCA CTT CCA CTA CTG TTG CAT AAA CAA CCA AGA CCA TGC TGC CTT TAA
Asn Val Thr Lys Thr Lys Glu Thr Lys Ile Ile Ala Lys Leu Gly Glu Gly Asp Asp Asn Val Phe Val Gly Ser Gly Thr Thr Glu Ile>
___C___C___C___C___C___C___C___C___C___C____RECOMBINANT LEUKOTOXIN PEPTIDE_C___C___C___C___C___C___C___C___C___C___C___>

     .  1810  .  1820  .  1830  .  1840  .  1850  .  1860  .  1870  .  1880  .  1890
GAT GGC GGT GAA GGT TAC GAC CGA GTT CAC TAT AGC CGT GGA AAC TAT GGT GCT TTA ACT ATT GAT GCA ACC AAA GAG ACC GAG CAA GGT
CTA CCG CCA CTT CCA ATG CTG GCT CAA GTG ATA TCG GCA CCT TTG ATA CCA CGA AAT TGA TAA CTA CGT TGG TTT CTC TGG CTC GTT CCA
Asp Gly Gly Glu Gly Tyr Asp Arg Val His Tyr Ser Arg Gly Asn Tyr Gly Ala Leu Thr Ile Asp Ala Thr Lys Glu Thr Glu Gln Gly>
___C___C___C___C___C___C___C___C___C___C____RECOMBINANT LEUKOTOXIN PEPTIDE_C___C___C___C___C___C___C___C___C___C___C___>
```

FIG. 11F

```
          .  1900    .  1910    .  1920    .  1930    .  1940    .  1950    .  1960    .  1970    .  1980
AGT TAT ACC GTA AAT CGT TTC GTA GAA ACC GGT AAA GCA CTA CAC GAA GTG ACT TCA ACC CAT ACC GCA TTA GTG GGC AAC CGT GAA GAA
TCA ATA TGG CAT TTA GCA AAG CAT CTT TGG CCA TTT CGT GAT GTG CTT CAC TGA AGT TGG GTA TGG CGT AAT CAC CCG TTG GCA CTT CTT
Ser Tyr Thr Val Asn Arg Phe Val Glu Thr Gly Lys Ala Leu His Glu Val Thr Ser Thr His Thr Ala Leu Val Gly Asn Arg Glu Glu>
___C___C___C___C___C___C___C___C___C___C____RECOMBINANT LEUKOTOXIN PEPTIDE_C___C___C___C___C___C___C___C___C___C___C___>

          .  1990    .  2000    .  2010    .  2020    .  2030    .  2040    .  2050    .  2060    .  2070
AAA ATA GAA TAT CGT CAT AGC AAT AAC CAG CAC CAT GCC GGT TAT TAC ACC AAA GAT ACC TTG AAA GCT GTT GAA GAA ATT ATC GGT ACA
TTT TAT CTT ATA GCA GTA TCG TTA TTG GTC GTG GTA CGG CCA ATA ATG TGG TTT CTA TGG AAC TTT CGA CAA CTT CTT TAA TAG CCA TGT
Lys Ile Glu Tyr Arg His Ser Asn Asn Gln His His Ala Gly Tyr Tyr Thr Lys Asp Thr Leu Lys Ala Val Glu Glu Ile Ile Gly Thr>
___C___C___C___C___C___C___C___C___C___C____RECOMBINANT LEUKOTOXIN PEPTIDE_C___C___C___C___C___C___C___C___C___C___C___>

          .  2080    .  2090    .  2100    .  2110    .  2120    .  2130    .  2140    .  2150    .  2160
TCA CAT AAC GAT ATC TTT AAA GGT AGT AAG TTC AAT GAT GCC TTT AAC GGT GGT GAT GGT GTC GAT ACT ATT GAC GGT AAC GAC GGC AAT
AGT GTA TTG CTA TAG AAA TTT CCA TCA TTC AAG TTA CTA CGG AAA TTG CCA CCA CTA CCA CAG CTA TGA TAA CTG CCA TTG CTG CCG TTA
Ser His Asn Asp Ile Phe Lys Gly Ser Lys Phe Asn Asp Ala Phe Asn Gly Gly Asp Gly Val Asp Thr Ile Asp Gly Asn Asp Gly Asn>
___C___C___C___C___C___C___C___C___C___C____RECOMBINANT LEUKOTOXIN PEPTIDE_C___C___C___C___C___C___C___C___C___C___C___>
```

FIG. 11G

```
      .  2170   .  2180   .  2190   .  2200   .  2210   .  2220   .  2230   .  2240   .  2250
GAC CGC TTA TTT GGT GGT AAA GGC GAT GAT ATT CTC GAT GGT GGA AAT GGT GAT GAT TTT ATC GAT GGC GGT AAA GGC AAC GAC CTA TTA
CTG GCG AAT AAA CCA CCA TTT CCG CTA CTA TAA GAG CTA CCA CCT TTA CCA CTA CTA AAA TAG CTA CCG CCA TTT CCG TTG CTG GAT AAT
Asp Arg Leu Phe Gly Gly Lys Gly Asp Asp Ile Leu Asp Gly Gly Asn Gly Asp Asp Phe Ile Asp Gly Gly Lys Gly Asn Asp Leu Leu>
___C___C___C___C___C___C___C___C___C___C____RECOMBINANT LEUKOTOXIN PEPTIDE_C___C___C___C___C___C___C___C___C___C___C___>

      .  2260   .  2270   .  2280   .  2290   .  2300   .  2310   .  2320   .  2330   .  2340
CAC GGT GGC AAG GGC GAT GAT ATT TTC GTT CAC CGT AAA GGC GAT GGT AAT GAT ATT ATT ACC GAT TCT GAC GGC AAT GAT AAA TTA TCA
GTG CCA CCG TTC CCG CTA CTA TAA AAG CAA GTG GCA TTT CCG CTA CCA TTA CTA TAA TAA TGG CTA AGA CTG CCG TTA CTA TTT AAT AGT
His Gly Gly Lys Gly Asp Asp Ile Phe Val His Arg Lys Gly Asp Gly Asn Asp Ile Ile Thr Asp Ser Asp Gly Asn Asp Lys Leu Ser>
___C___C___C___C___C___C___C___C___C___C____RECOMBINANT LEUKOTOXIN PEPTIDE_C___C___C___C___C___C___C___C___C___C___C___>

      .  2350   .  2360   .  2370   .  2380   .  2390   .  2400   .  2410   .  2420   .  2430
TTC TCT GAT TCG AAC TTA AAA GAT TTA ACA TTT GAA AAA GTT AAA CAT AAT CTT GTC ATC ACG AAT AGC AAA AAA GAG AAA GTG ACC ATT
AAG AGA CTA AGC TTG AAT TTT CTA AAT TGT AAA CTT TTT CAA TTT GTA TTA GAA CAG TAG TGC TTA TCG TTT TTT CTC TTT CAC TGG TAA
Phe Ser Asp Ser Asn Leu Lys Asp Leu Thr Phe Glu Lys Val Lys His Asn Leu Val Ile Thr Asn Ser Lys Lys Glu Lys Val Thr Ile>
___C___C___C___C___C___C___C___C___C___C____RECOMBINANT LEUKOTOXIN PEPTIDE_C___C___C___C___C___C___C___C___C___C___C___>

      .  2440   .  2450   .  2460   .  2470   .  2480   .  2490   .  2500   .  2510   .  2520
CAA AAC TGG TTC CGA GAG GCT GAT TTT GCT AAA GAA GTG CCT AAT TAT AAA GCA ACT AAA GAT GAG AAA ATC GAA GAA ATC ATC GGT CAA
GTT TTG ACC AAG GCT CTC CGA CTA AAA CGA TTT CTT CAC GGA TTA ATA TTT CGT TGA TTT CTA CTC TTT TAG CTT CTT TAG TAG CCA GTT
Gln Asn Trp Phe Arg Glu Ala Asp Phe Ala Lys Glu Val Pro Asn Tyr Lys Ala Thr Lys Asp Glu Lys Ile Glu Glu Ile Ile Gly Gln>
___C___C___C___C___C___C___C___C___C___C____RECOMBINANT LEUKOTOXIN PEPTIDE_C___C___C___C___C___C___C___C___C___C___C___>
```

FIG. 11H

```
          2530      2540      2550      2560      2570      2580      2590      2600      2610
AAT GGC GAG CGG ATC ACC TCA AAG CAA GTT GAT GAT CTT ATC GCA AAA GGT AAC GGC AAA ATT ACC CAA GAT GAG CTA TCA AAA GTT GTT
TTA CCG CTC GCC TAG TGG AGT TTC GTT CAA CTA CTA GAA TAG CGT TTT CCA TTG CCG TTT TAA TGG GTT CTA CTC GAT AGT TTT CAA CAA
Asn Gly Glu Arg Ile Thr Ser Lys Gln Val Asp Asp Leu Ile Ala Lys Gly Asn Gly Lys Ile Thr Gln Asp Glu Leu Ser Lys Val Val>
___C___C___C___C___C___C___C___C___C___C____RECOMBINANT LEUKOTOXIN PEPTIDE_C___C___C___C___C___C___C___C___C___C___C___>

          2620      2630      2640      2650      2660      2670      2680      2690      2700
GAT AAC TAT GAA TTG CTC AAA CAT AGC AAA AAT GTG ACA AAC AGC TTA GAT AAG TTA ATC TCA TCT GTA AGT GCA TTT ACC TCG TCT AAT
CTA TTG ATA CTT AAC GAG TTT GTA TCG TTT TTA CAC TGT TTG TCG AAT CTA TTC AAT TAG AGT AGA CAT TCA CGT AAA TGG AGC AGA TTA
Asp Asn Tyr Glu Leu Leu Lys His Ser Lys Asn Val Thr Asn Ser Leu Asp Lys Leu Ile Ser Ser Val Ser Ala Phe Thr Ser Ser Asn>
___C___C___C___C___C___C___C___C___C___C____RECOMBINANT LEUKOTOXIN PEPTIDE_C___C___C___C___C___C___C___C___C___C___C___>

          2710      2720      2730      2740      2750      2760      2770      2780      2790
GAT TCG AGA AAT GTA TTA GTG GCT CCA ACT TCA ATG TTG GAT CAA AGT TTA TCT TCT CTT CAA TTT GCT AGG GGA TCC TAG CTAGCTAGCCATG
CTA AGC TCT TTA CAT AAT CAC CGA GGT TGA AGT TAC AAC CTA GTT TCA AAT AGA AGA GAA GTT AAA CGA TCC CCT AGG ATC GATCGATCGGTAC
Asp Ser Arg Asn Val Leu Val Ala Pro Thr Ser Met Leu Asp Gln Ser Leu Ser Ser Leu Gln Phe Ala Arg Gly Ser End>
___C___C___C___C___C___C___C___C___C--RECOMBINANT LEUKOTOXIN PEPTIDE---C___C___C___C___C___C___C___C___C___>
                                                                                         _b___VECTOR SEQUENCE_______>
```

FIG. 11I

SEQUENCE LISTING

```
<160> NUMBER OF SEQ ID NOS: 38

<210> SEQ ID NO 1
<211> LENGTH: 256
<212> TYPE: PRT
<213> ORGANISM: Sheep

<400> SEQUENCE: 1

Met Val Lys Ser His Ile Gly Ser Trp Ile Leu Val Leu Phe Val Ala
1               5                   10                  15

Met Trp Ser Asp Val Gly Leu Cys Lys Lys Arg Pro Lys Pro Gly Gly
            20                  25                  30

Gly Trp Asn Thr Gly Gly Ser Arg Tyr Pro Gly Gln Gly Ser Pro Gly
        35                  40                  45

Gly Asn Arg Tyr Pro Pro Gln Gly Gly Gly Gly Trp Gly Gln Pro His
    50                  55                  60

Gly Gly Gly Trp Gly Gln Pro His Gly Gly Gly Trp Gly Gln Pro His
65                  70                  75                  80

Gly Gly Gly Trp Gly Gln Pro His Gly Gly Gly Gly Trp Gly Gln Gly
                85                  90                  95

Gly Ser His Ser Gln Trp Asn Lys Pro Ser Lys Pro Lys Thr Asn Met
            100                 105                 110

Lys His Val Ala Gly Ala Ala Ala Ala Gly Ala Val Val Gly Gly Leu
```

-continued

```
        115                 120                 125

Gly Gly Tyr Met Leu Gly Ser Ala Met Ser Arg Pro Leu Ile His Phe
    130                 135                 140

Gly Asn Asp Tyr Glu Asp Arg Tyr Tyr Arg Glu Asn Met Tyr Arg Tyr
145                 150                 155                 160

Pro Asn Gln Val Tyr Tyr Arg Pro Val Asp Gln Tyr Ser Asn Gln Asn
                165                 170                 175

Asn Phe Val His Asp Cys Val Asn Ile Thr Val Lys Gln His Thr Val
            180                 185                 190

Thr Thr Thr Thr Lys Gly Glu Asn Phe Thr Glu Thr Asp Ile Lys Ile
        195                 200                 205

Met Glu Arg Val Val Glu Gln Met Cys Ile Thr Gln Tyr Gln Arg Glu
    210                 215                 220

Ser Gln Ala Tyr Tyr Gln Arg Gly Ala Ser Val Ile Leu Phe Ser Ser
225                 230                 235                 240

Pro Pro Val Ile Leu Leu Ile Ser Phe Leu Ile Phe Leu Ile Val Gly
                245                 250                 255


<210> SEQ ID NO 2
<211> LENGTH: 264
<212> TYPE: PRT
<213> ORGANISM: Bovine
<220> FEATURE:
<221> NAME/KEY: misc_feature
<222> LOCATION: (154)..(154)
<223> OTHER INFORMATION: Xaa can be any naturally occurring amino acid

<400> SEQUENCE: 2

Met Val Lys Ser His Ile Gly Ser Trp Ile Leu Val Leu Phe Val Ala
1               5                   10                  15

Met Trp Ser Asp Val Gly Leu Cys Lys Lys Arg Pro Lys Pro Gly Gly
            20                  25                  30

Gly Trp Asn Thr Gly Gly Ser Arg Tyr Pro Gly Gln Gly Ser Pro Gly
        35                  40                  45

Gly Asn Arg Tyr Pro Pro Gln Gly Gly Gly Gly Trp Gly Gln Pro His
    50                  55                  60

Gly Gly Gly Trp Gly Gln Pro His Gly Gly Gly Trp Gly Gln Pro His
65                  70                  75                  80

Gly Gly Gly Trp Gly Gln Pro His Gly Gly Gly Trp Gly Gln Pro His
                85                  90                  95

Gly Gly Gly Gly Trp Gly Gln Gly Gly Thr His Gly Gln Trp Asn Lys
            100                 105                 110

Pro Ser Lys Pro Lys Thr Asn Met Lys His Val Ala Gly Ala Ala Ala
        115                 120                 125

Ala Gly Ala Val Val Gly Gly Leu Gly Gly Tyr Met Leu Gly Ser Ala
    130                 135                 140

Met Ser Arg Pro Leu Ile His Phe Gly Xaa Asp Tyr Glu Asp Arg Tyr
145                 150                 155                 160

Tyr Arg Glu Asn Met His Arg Tyr Pro Asn Gln Val Tyr Tyr Arg Pro
                165                 170                 175

Val Asp Gln Tyr Ser Asn Gln Asn Asn Phe Val His Asp Cys Val Asn
            180                 185                 190

Ile Thr Val Lys Glu His Thr Val Thr Thr Thr Thr Lys Gly Glu Asn
        195                 200                 205

Phe Thr Glu Thr Asp Ile Lys Met Met Glu Arg Val Val Glu Gln Met
    210                 215                 220
```

```
Cys Ile Thr Gln Tyr Gln Arg Glu Ser Gln Ala Tyr Tyr Gln Arg Gly
225                 230                 235                 240

Ala Ser Val Ile Leu Phe Ser Ser Pro Pro Val Ile Leu Leu Ile Ser
                245                 250                 255

Phe Leu Ile Phe Leu Ile Val Gly
            260


<210> SEQ ID NO 3
<211> LENGTH: 253
<212> TYPE: PRT
<213> ORGANISM: Human

<400> SEQUENCE: 3

Met Ala Asn Leu Gly Cys Trp Met Leu Val Leu Phe Val Ala Thr Trp
1               5                   10                  15

Ser Asp Leu Gly Leu Cys Lys Lys Arg Pro Lys Pro Gly Gly Trp Asn
            20                  25                  30

Thr Gly Gly Ser Arg Tyr Pro Gly Gln Gly Ser Pro Gly Gly Asn Arg
        35                  40                  45

Tyr Pro Pro Gln Gly Gly Gly Gly Trp Gly Gln Pro His Gly Gly Gly
    50                  55                  60

Trp Gly Gln Pro His Gly Gly Gly Trp Gly Gln Pro His Gly Gly Gly
65                  70                  75                  80

Trp Gly Gln Pro His Gly Gly Gly Trp Gly Gln Gly Gly Gly Thr His
                85                  90                  95

Ser Gln Trp Asn Lys Pro Ser Lys Pro Lys Thr Asn Met Lys His Met
            100                 105                 110

Ala Gly Ala Ala Ala Ala Gly Ala Val Val Gly Gly Leu Gly Gly Tyr
        115                 120                 125

Val Leu Gly Ser Ala Met Ser Arg Pro Ile Ile His Phe Gly Ser Asp
    130                 135                 140

Tyr Glu Asp Arg Tyr Tyr Arg Glu Asn Met His Arg Tyr Pro Asn Gln
145                 150                 155                 160

Val Tyr Tyr Arg Pro Met Asp Glu Tyr Ser Asn Gln Asn Asn Phe Val
                165                 170                 175

His Asp Cys Val Asn Ile Thr Ile Lys Gln His Thr Val Thr Thr Thr
            180                 185                 190

Thr Lys Gly Glu Asn Phe Thr Glu Thr Asp Val Lys Met Met Glu Arg
        195                 200                 205

Val Val Glu Gln Met Cys Ile Thr Gln Tyr Glu Arg Glu Ser Gln Ala
    210                 215                 220

Tyr Tyr Gln Arg Gly Ser Ser Met Val Leu Phe Ser Ser Pro Pro Val
225                 230                 235                 240

Ile Leu Leu Ile Ser Phe Leu Ile Phe Leu Ile Val Gly
                245                 250


<210> SEQ ID NO 4
<211> LENGTH: 254
<212> TYPE: PRT
<213> ORGANISM: Mouse

<400> SEQUENCE: 4

Met Ala Asn Leu Gly Tyr Trp Leu Leu Ala Leu Phe Val Thr Met Trp
1               5                   10                  15

Thr Asp Val Gly Leu Cys Lys Lys Arg Pro Lys Pro Gly Gly Trp Asn
            20                  25                  30
```

```
Thr Gly Gly Ser Arg Tyr Pro Gly Gln Gly Ser Pro Gly Gly Asn Arg
        35                  40                  45

Tyr Pro Pro Gln Gly Gly Thr Trp Gly Gln Pro His Gly Gly Gly Trp
    50                  55                  60

Gly Gln Pro His Gly Gly Ser Trp Gly Gln Pro His Gly Gly Ser Trp
65                  70                  75                  80

Gly Gln Pro His Gly Gly Gly Trp Gly Gln Gly Gly Gly Thr His Asn
                85                  90                  95

Gln Trp Asn Lys Pro Ser Lys Pro Lys Thr Asn Leu Lys His Val Ala
            100                 105                 110

Gly Ala Ala Ala Ala Gly Ala Val Val Gly Gly Leu Gly Gly Tyr Met
        115                 120                 125

Leu Gly Ser Ala Met Ser Arg Pro Met Ile His Phe Gly Asn Asp Trp
    130                 135                 140

Glu Asp Arg Tyr Tyr Arg Glu Asn Met Tyr Arg Tyr Pro Asn Gln Val
145                 150                 155                 160

Tyr Tyr Arg Pro Val Asp Gln Tyr Ser Asn Gln Asn Asn Phe Val His
                165                 170                 175

Asp Cys Val Asn Ile Thr Ile Lys Gln His Thr Val Thr Thr Thr Thr
            180                 185                 190

Lys Gly Glu Asn Phe Thr Glu Thr Asp Val Lys Met Met Glu Arg Val
        195                 200                 205

Val Glu Gln Met Cys Val Thr Gln Tyr Gln Lys Glu Ser Gln Ala Tyr
    210                 215                 220

Tyr Asp Gly Arg Arg Ser Ser Ser Thr Val Leu Phe Ser Ser Pro Pro
225                 230                 235                 240

Val Ile Leu Leu Ile Ser Phe Leu Ile Phe Leu Ile Val Gly
                245                 250


<210> SEQ ID NO 5
<211> LENGTH: 256
<212> TYPE: PRT
<213> ORGANISM: Elk

<400> SEQUENCE: 5

Met Val Lys Ser His Ile Gly Ser Trp Ile Leu Val Leu Phe Val Ala
1               5                   10                  15

Met Trp Ser Asp Val Gly Leu Cys Lys Lys Arg Pro Lys Pro Gly Gly
            20                  25                  30

Gly Trp Asn Thr Gly Gly Ser Arg Tyr Pro Gly Gln Gly Ser Pro Gly
        35                  40                  45

Gly Asn Arg Tyr Pro Pro Gln Gly Gly Gly Gly Trp Gly Gln Pro His
    50                  55                  60

Gly Gly Gly Trp Gly Gln Pro His Gly Gly Gly Trp Gly Gln Pro His
65                  70                  75                  80

Gly Gly Gly Trp Gly Gln Pro His Gly Gly Gly Gly Trp Gly Gln Gly
                85                  90                  95

Gly Thr His Ser Gln Trp Asn Lys Pro Ser Lys Pro Lys Thr Asn Met
            100                 105                 110

Lys His Val Ala Gly Ala Ala Ala Ala Gly Ala Val Val Gly Gly Leu
        115                 120                 125

Gly Gly Tyr Met Leu Gly Ser Ala Met Ser Arg Pro Leu Ile His Phe
    130                 135                 140

Gly Asn Asp Tyr Glu Asp Arg Tyr Tyr Arg Glu Asn Met Tyr Arg Tyr
```

```
145                 150                 155                 160

Pro Asn Gln Val Tyr Tyr Arg Pro Val Asp Gln Tyr Asn Asn Gln Asn
                165                 170                 175

Thr Phe Val His Asp Cys Val Asn Ile Thr Val Lys Gln His Thr Val
            180                 185                 190

Thr Thr Thr Thr Lys Gly Glu Asn Phe Thr Glu Thr Asp Ile Lys Met
        195                 200                 205

Met Glu Arg Val Val Glu Gln Met Cys Ile Thr Gln Tyr Gln Arg Glu
    210                 215                 220

Ser Glu Ala Tyr Tyr Gln Arg Gly Ala Ser Val Ile Leu Phe Ser Ser
225                 230                 235                 240

Pro Pro Val Ile Leu Leu Ile Ser Phe Leu Ile Phe Leu Ile Val Gly
                245                 250                 255


<210> SEQ ID NO 6
<211> LENGTH: 2794
<212> TYPE: DNA
<213> ORGANISM: Pasteurella haemolytica
<220> FEATURE:
<221> NAME/KEY: misc_feature
<223> OTHER INFORMATION: DNA Sequence shown in Figure 11
<220> FEATURE:
<221> NAME/KEY: CDS
<222> LOCATION: (1)..(2778)

<400> SEQUENCE: 6

atg gct act gtt ata gat cta agc ttc cca aaa act ggg gca aaa aaa       48
Met Ala Thr Val Ile Asp Leu Ser Phe Pro Lys Thr Gly Ala Lys Lys
1               5                   10                  15

att atc ctc tat att ccc caa aat tac caa tat gat act gaa caa ggt       96
Ile Ile Leu Tyr Ile Pro Gln Asn Tyr Gln Tyr Asp Thr Glu Gln Gly
            20                  25                  30

aat ggt tta cag gat tta gtc aaa gcg gcc gaa gag ttg ggg att gag      144
Asn Gly Leu Gln Asp Leu Val Lys Ala Ala Glu Glu Leu Gly Ile Glu
        35                  40                  45

gta caa aga gaa gaa cgc aat aat att gca aca gct caa acc agt tta      192
Val Gln Arg Glu Glu Arg Asn Asn Ile Ala Thr Ala Gln Thr Ser Leu
    50                  55                  60

ggc acg att caa acc gct att ggc tta act gag cgt ggc att gtg tta      240
Gly Thr Ile Gln Thr Ala Ile Gly Leu Thr Glu Arg Gly Ile Val Leu
65                  70                  75                  80

tcc gct cca caa att gat aaa ttg cta cag aaa act aaa gca ggc caa      288
Ser Ala Pro Gln Ile Asp Lys Leu Leu Gln Lys Thr Lys Ala Gly Gln
                85                  90                  95

gca tta ggt tct gcc gaa agc att gta caa aat gca aat aaa gcc aaa      336
Ala Leu Gly Ser Ala Glu Ser Ile Val Gln Asn Ala Asn Lys Ala Lys
            100                 105                 110

act gta tta tct ggc att caa tct att tta ggc tca gta ttg gct gga      384
Thr Val Leu Ser Gly Ile Gln Ser Ile Leu Gly Ser Val Leu Ala Gly
        115                 120                 125

atg gat tta gat gag gcc tta cag aat aac agc aac caa cat gct ctt      432
Met Asp Leu Asp Glu Ala Leu Gln Asn Asn Ser Asn Gln His Ala Leu
    130                 135                 140

gct aaa gct ggc ttg gag cta aca aat tca tta att gaa aat att gct      480
Ala Lys Ala Gly Leu Glu Leu Thr Asn Ser Leu Ile Glu Asn Ile Ala
145                 150                 155                 160

aat tca gta aaa aca ctt gac gaa ttt ggt gag caa att agt caa ttt      528
Asn Ser Val Lys Thr Leu Asp Glu Phe Gly Glu Gln Ile Ser Gln Phe
                165                 170                 175

ggt tca aaa cta caa aat atc aaa ggc tta ggg act tta gga gac aaa      576
```

```
Gly Ser Lys Leu Gln Asn Ile Lys Gly Leu Gly Thr Leu Gly Asp Lys
            180                 185                 190

ctc aaa aat atc ggt gga ctt gat aaa gct ggc ctt ggt tta gat gtt      624
Leu Lys Asn Ile Gly Gly Leu Asp Lys Ala Gly Leu Gly Leu Asp Val
        195                 200                 205

atc tca ggg cta tta tcg ggc gca aca gct gca ctt gta ctt gca gat      672
Ile Ser Gly Leu Leu Ser Gly Ala Thr Ala Ala Leu Val Leu Ala Asp
    210                 215                 220

aaa aat gct tca aca gct aaa aaa gtg ggt gcg ggt ttt gaa ttg gca      720
Lys Asn Ala Ser Thr Ala Lys Lys Val Gly Ala Gly Phe Glu Leu Ala
225                 230                 235                 240

aac caa gtt gtt ggt aat att acc aaa gcc gtt tct tct tac att tta      768
Asn Gln Val Val Gly Asn Ile Thr Lys Ala Val Ser Ser Tyr Ile Leu
                245                 250                 255

gcc caa cgt gtt gca gca ggt tta tct tca act ggg cct gtg gct gct      816
Ala Gln Arg Val Ala Ala Gly Leu Ser Ser Thr Gly Pro Val Ala Ala
            260                 265                 270

tta att gct tct act gtt tct ctt gcg att agc cca tta gca ttt gcc      864
Leu Ile Ala Ser Thr Val Ser Leu Ala Ile Ser Pro Leu Ala Phe Ala
        275                 280                 285

ggt att gcc gat aaa ttt aat cat gca aaa agt tta gag agt tat gcc      912
Gly Ile Ala Asp Lys Phe Asn His Ala Lys Ser Leu Glu Ser Tyr Ala
    290                 295                 300

gaa cgc ttt aaa aaa tta ggc tat gac gga gat aat tta tta gca gaa      960
Glu Arg Phe Lys Lys Leu Gly Tyr Asp Gly Asp Asn Leu Leu Ala Glu
305                 310                 315                 320

tat cag cgg gga aca ggg act att gat gca tcg gtt act gca att aat     1008
Tyr Gln Arg Gly Thr Gly Thr Ile Asp Ala Ser Val Thr Ala Ile Asn
                325                 330                 335

acc gca ttg gcc gct att gct ggt ggt gtg tct gct gct gca gcc ggc     1056
Thr Ala Leu Ala Ala Ile Ala Gly Gly Val Ser Ala Ala Ala Ala Gly
            340                 345                 350

tcg gtt att gct tca ccg att gcc tta tta gta tct ggg att acc ggt     1104
Ser Val Ile Ala Ser Pro Ile Ala Leu Leu Val Ser Gly Ile Thr Gly
        355                 360                 365

gta att tct acg att ctg caa tat tct aaa caa gca atg ttt gag cac     1152
Val Ile Ser Thr Ile Leu Gln Tyr Ser Lys Gln Ala Met Phe Glu His
    370                 375                 380

gtt gca aat aaa att cat aac aaa att gta gaa tgg gaa aaa aat aat     1200
Val Ala Asn Lys Ile His Asn Lys Ile Val Glu Trp Glu Lys Asn Asn
385                 390                 395                 400

cac ggt aag aac tac ttt gaa aat ggt tac gat gcc cgt tat ctt gcg     1248
His Gly Lys Asn Tyr Phe Glu Asn Gly Tyr Asp Ala Arg Tyr Leu Ala
                405                 410                 415

aat tta caa gat aat atg aaa ttc tta ctg aac tta aac aaa gag tta     1296
Asn Leu Gln Asp Asn Met Lys Phe Leu Leu Asn Leu Asn Lys Glu Leu
            420                 425                 430

cag gca gaa cgt gtc atc gct att act cag cag caa tgg gat aac aac     1344
Gln Ala Glu Arg Val Ile Ala Ile Thr Gln Gln Gln Trp Asp Asn Asn
        435                 440                 445

att ggt gat tta gct ggt att agc cgt tta ggt gaa aaa gtc ctt agt     1392
Ile Gly Asp Leu Ala Gly Ile Ser Arg Leu Gly Glu Lys Val Leu Ser
    450                 455                 460

ggt aaa gcc tat gtg gat gcg ttt gaa gaa ggc aaa cac att aaa gcc     1440
Gly Lys Ala Tyr Val Asp Ala Phe Glu Glu Gly Lys His Ile Lys Ala
465                 470                 475                 480

gat aaa tta gta cag ttg gat tcg gca aac ggt att att gat gtg agt     1488
Asp Lys Leu Val Gln Leu Asp Ser Ala Asn Gly Ile Ile Asp Val Ser
                485                 490                 495
```

```
aat tcg ggt aaa gcg aaa act cag cat atc tta ttc aga acg cca tta      1536
Asn Ser Gly Lys Ala Lys Thr Gln His Ile Leu Phe Arg Thr Pro Leu
            500                 505                 510

ttg acg ccg gga aca gag cat cgt gaa cgc gta caa aca ggt aaa tat      1584
Leu Thr Pro Gly Thr Glu His Arg Glu Arg Val Gln Thr Gly Lys Tyr
        515                 520                 525

gaa tat att acc aag ctc aat att aac cgt gta gat agc tgg aaa att      1632
Glu Tyr Ile Thr Lys Leu Asn Ile Asn Arg Val Asp Ser Trp Lys Ile
    530                 535                 540

aca gat ggt gca gca agt tct acc ttt gat tta act aac gtt gtt cag      1680
Thr Asp Gly Ala Ala Ser Ser Thr Phe Asp Leu Thr Asn Val Val Gln
545                 550                 555                 560

cgt att ggt att gaa tta gac aat gct gga aat gta act aaa acc aaa      1728
Arg Ile Gly Ile Glu Leu Asp Asn Ala Gly Asn Val Thr Lys Thr Lys
                565                 570                 575

gaa aca aaa att att gcc aaa ctt ggt gaa ggt gat gac aac gta ttt      1776
Glu Thr Lys Ile Ile Ala Lys Leu Gly Glu Gly Asp Asp Asn Val Phe
            580                 585                 590

gtt ggt tct ggt acg acg gaa att gat ggc ggt gaa ggt tac gac cga      1824
Val Gly Ser Gly Thr Thr Glu Ile Asp Gly Gly Glu Gly Tyr Asp Arg
        595                 600                 605

gtt cac tat agc cgt gga aac tat ggt gct tta act att gat gca acc      1872
Val His Tyr Ser Arg Gly Asn Tyr Gly Ala Leu Thr Ile Asp Ala Thr
    610                 615                 620

aaa gag acc gag caa ggt agt tat acc gta aat cgt ttc gta gaa acc      1920
Lys Glu Thr Glu Gln Gly Ser Tyr Thr Val Asn Arg Phe Val Glu Thr
625                 630                 635                 640

ggt aaa gca cta cac gaa gtg act tca acc cat acc gca tta gtg ggc      1968
Gly Lys Ala Leu His Glu Val Thr Ser Thr His Thr Ala Leu Val Gly
                645                 650                 655

aac cgt gaa gaa aaa ata gaa tat cgt cat agc aat aac cag cac cat      2016
Asn Arg Glu Glu Lys Ile Glu Tyr Arg His Ser Asn Asn Gln His His
            660                 665                 670

gcc ggt tat tac acc aaa gat acc ttg aaa gct gtt gaa gaa att atc      2064
Ala Gly Tyr Tyr Thr Lys Asp Thr Leu Lys Ala Val Glu Glu Ile Ile
        675                 680                 685

ggt aca tca cat aac gat atc ttt aaa ggt agt aag ttc aat gat gcc      2112
Gly Thr Ser His Asn Asp Ile Phe Lys Gly Ser Lys Phe Asn Asp Ala
    690                 695                 700

ttt aac ggt ggt gat ggt gtc gat act att gac ggt aac gac ggc aat      2160
Phe Asn Gly Gly Asp Gly Val Asp Thr Ile Asp Gly Asn Asp Gly Asn
705                 710                 715                 720

gac cgc tta ttt ggt ggt aaa ggc gat gat att ctc gat ggt gga aat      2208
Asp Arg Leu Phe Gly Gly Lys Gly Asp Asp Ile Leu Asp Gly Gly Asn
                725                 730                 735

ggt gat gat ttt atc gat ggc ggt aaa ggc aac gac cta tta cac ggt      2256
Gly Asp Asp Phe Ile Asp Gly Gly Lys Gly Asn Asp Leu Leu His Gly
            740                 745                 750

ggc aag ggc gat gat att ttc gtt cac cgt aaa ggc gat ggt aat gat      2304
Gly Lys Gly Asp Asp Ile Phe Val His Arg Lys Gly Asp Gly Asn Asp
        755                 760                 765

att att acc gat tct gac ggc aat gat aaa tta tca ttc tct gat tcg      2352
Ile Ile Thr Asp Ser Asp Gly Asn Asp Lys Leu Ser Phe Ser Asp Ser
    770                 775                 780

aac tta aaa gat tta aca ttt gaa aaa gtt aaa cat aat ctt gtc atc      2400
Asn Leu Lys Asp Leu Thr Phe Glu Lys Val Lys His Asn Leu Val Ile
785                 790                 795                 800

acg aat agc aaa aaa gag aaa gtg acc att caa aac tgg ttc cga gag      2448
Thr Asn Ser Lys Lys Glu Lys Val Thr Ile Gln Asn Trp Phe Arg Glu
                805                 810                 815
```

```
gct gat ttt gct aaa gaa gtg cct aat tat aaa gca act aaa gat gag      2496
Ala Asp Phe Ala Lys Glu Val Pro Asn Tyr Lys Ala Thr Lys Asp Glu
            820                 825                 830

aaa atc gaa gaa atc atc ggt caa aat ggc gag cgg atc acc tca aag      2544
Lys Ile Glu Glu Ile Ile Gly Gln Asn Gly Glu Arg Ile Thr Ser Lys
        835                 840                 845

caa gtt gat gat ctt atc gca aaa ggt aac ggc aaa att acc caa gat      2592
Gln Val Asp Asp Leu Ile Ala Lys Gly Asn Gly Lys Ile Thr Gln Asp
    850                 855                 860

gag cta tca aaa gtt gtt gat aac tat gaa ttg ctc aaa cat agc aaa      2640
Glu Leu Ser Lys Val Val Asp Asn Tyr Glu Leu Leu Lys His Ser Lys
865                 870                 875                 880

aat gtg aca aac agc tta gat aag tta atc tca tct gta agt gca ttt      2688
Asn Val Thr Asn Ser Leu Asp Lys Leu Ile Ser Ser Val Ser Ala Phe
                885                 890                 895

acc tcg tct aat gat tcg aga aat gta tta gtg gct cca act tca atg      2736
Thr Ser Ser Asn Asp Ser Arg Asn Val Leu Val Ala Pro Thr Ser Met
            900                 905                 910

ttg gat caa agt tta tct tct ctt caa ttt gct agg gga tcc              2778
Leu Asp Gln Ser Leu Ser Ser Leu Gln Phe Ala Arg Gly Ser
        915                 920                 925

tagctagcta gccatg                                                    2794


<210> SEQ ID NO 7
<211> LENGTH: 926
<212> TYPE: PRT
<213> ORGANISM: Pasteurella haemolytica

<400> SEQUENCE: 7

Met Ala Thr Val Ile Asp Leu Ser Phe Pro Lys Thr Gly Ala Lys Lys
1               5                   10                  15

Ile Ile Leu Tyr Ile Pro Gln Asn Tyr Gln Tyr Asp Thr Glu Gln Gly
            20                  25                  30

Asn Gly Leu Gln Asp Leu Val Lys Ala Ala Glu Glu Leu Gly Ile Glu
        35                  40                  45

Val Gln Arg Glu Glu Arg Asn Asn Ile Ala Thr Ala Gln Thr Ser Leu
    50                  55                  60

Gly Thr Ile Gln Thr Ala Ile Gly Leu Thr Glu Arg Gly Ile Val Leu
65                  70                  75                  80

Ser Ala Pro Gln Ile Asp Lys Leu Leu Gln Lys Thr Lys Ala Gly Gln
                85                  90                  95

Ala Leu Gly Ser Ala Glu Ser Ile Val Gln Asn Ala Asn Lys Ala Lys
            100                 105                 110

Thr Val Leu Ser Gly Ile Gln Ser Ile Leu Gly Ser Val Leu Ala Gly
        115                 120                 125

Met Asp Leu Asp Glu Ala Leu Gln Asn Asn Ser Asn Gln His Ala Leu
    130                 135                 140

Ala Lys Ala Gly Leu Glu Leu Thr Asn Ser Leu Ile Glu Asn Ile Ala
145                 150                 155                 160

Asn Ser Val Lys Thr Leu Asp Glu Phe Gly Glu Gln Ile Ser Gln Phe
                165                 170                 175

Gly Ser Lys Leu Gln Asn Ile Lys Gly Leu Gly Thr Leu Gly Asp Lys
            180                 185                 190

Leu Lys Asn Ile Gly Gly Leu Asp Lys Ala Gly Leu Gly Leu Asp Val
        195                 200                 205

Ile Ser Gly Leu Leu Ser Gly Ala Thr Ala Ala Leu Val Leu Ala Asp
```

```
    210                 215                 220

Lys Asn Ala Ser Thr Ala Lys Lys Val Gly Ala Gly Phe Glu Leu Ala
225                 230                 235                 240

Asn Gln Val Val Gly Asn Ile Thr Lys Ala Val Ser Ser Tyr Ile Leu
                245                 250                 255

Ala Gln Arg Val Ala Ala Gly Leu Ser Ser Thr Gly Pro Val Ala Ala
            260                 265                 270

Leu Ile Ala Ser Thr Val Ser Leu Ala Ile Ser Pro Leu Ala Phe Ala
        275                 280                 285

Gly Ile Ala Asp Lys Phe Asn His Ala Lys Ser Leu Glu Ser Tyr Ala
    290                 295                 300

Glu Arg Phe Lys Lys Leu Gly Tyr Asp Gly Asp Asn Leu Leu Ala Glu
305                 310                 315                 320

Tyr Gln Arg Gly Thr Gly Thr Ile Asp Ala Ser Val Thr Ala Ile Asn
                325                 330                 335

Thr Ala Leu Ala Ala Ile Ala Gly Gly Val Ser Ala Ala Ala Ala Gly
            340                 345                 350

Ser Val Ile Ala Ser Pro Ile Ala Leu Leu Val Ser Gly Ile Thr Gly
        355                 360                 365

Val Ile Ser Thr Ile Leu Gln Tyr Ser Lys Gln Ala Met Phe Glu His
    370                 375                 380

Val Ala Asn Lys Ile His Asn Lys Ile Val Glu Trp Glu Lys Asn Asn
385                 390                 395                 400

His Gly Lys Asn Tyr Phe Glu Asn Gly Tyr Asp Ala Arg Tyr Leu Ala
                405                 410                 415

Asn Leu Gln Asp Asn Met Lys Phe Leu Leu Asn Leu Asn Lys Glu Leu
            420                 425                 430

Gln Ala Glu Arg Val Ile Ala Ile Thr Gln Gln Gln Trp Asp Asn Asn
        435                 440                 445

Ile Gly Asp Leu Ala Gly Ile Ser Arg Leu Gly Glu Lys Val Leu Ser
    450                 455                 460

Gly Lys Ala Tyr Val Asp Ala Phe Glu Glu Gly Lys His Ile Lys Ala
465                 470                 475                 480

Asp Lys Leu Val Gln Leu Asp Ser Ala Asn Gly Ile Ile Asp Val Ser
                485                 490                 495

Asn Ser Gly Lys Ala Lys Thr Gln His Ile Leu Phe Arg Thr Pro Leu
            500                 505                 510

Leu Thr Pro Gly Thr Glu His Arg Glu Arg Val Gln Thr Gly Lys Tyr
        515                 520                 525

Glu Tyr Ile Thr Lys Leu Asn Ile Asn Arg Val Asp Ser Trp Lys Ile
    530                 535                 540

Thr Asp Gly Ala Ala Ser Ser Thr Phe Asp Leu Thr Asn Val Val Gln
545                 550                 555                 560

Arg Ile Gly Ile Glu Leu Asp Asn Ala Gly Asn Val Thr Lys Thr Lys
                565                 570                 575

Glu Thr Lys Ile Ile Ala Lys Leu Gly Glu Gly Asp Asp Asn Val Phe
            580                 585                 590

Val Gly Ser Gly Thr Thr Glu Ile Asp Gly Gly Glu Gly Tyr Asp Arg
        595                 600                 605

Val His Tyr Ser Arg Gly Asn Tyr Gly Ala Leu Thr Ile Asp Ala Thr
    610                 615                 620

Lys Glu Thr Glu Gln Gly Ser Tyr Thr Val Asn Arg Phe Val Glu Thr
625                 630                 635                 640
```

```
Gly Lys Ala Leu His Glu Val Thr Ser Thr His Thr Ala Leu Val Gly
                645                 650                 655

Asn Arg Glu Glu Lys Ile Glu Tyr Arg His Ser Asn Asn Gln His His
            660                 665                 670

Ala Gly Tyr Tyr Thr Lys Asp Thr Leu Lys Ala Val Glu Glu Ile Ile
        675                 680                 685

Gly Thr Ser His Asn Asp Ile Phe Lys Gly Ser Lys Phe Asn Asp Ala
    690                 695                 700

Phe Asn Gly Gly Asp Gly Val Asp Thr Ile Asp Gly Asn Asp Gly Asn
705                 710                 715                 720

Asp Arg Leu Phe Gly Gly Lys Gly Asp Asp Ile Leu Asp Gly Gly Asn
                725                 730                 735

Gly Asp Asp Phe Ile Asp Gly Gly Lys Gly Asn Asp Leu Leu His Gly
            740                 745                 750

Gly Lys Gly Asp Asp Ile Phe Val His Arg Lys Gly Asp Gly Asn Asp
        755                 760                 765

Ile Ile Thr Asp Ser Asp Gly Asn Asp Lys Leu Ser Phe Ser Asp Ser
    770                 775                 780

Asn Leu Lys Asp Leu Thr Phe Glu Lys Val Lys His Asn Leu Val Ile
785                 790                 795                 800

Thr Asn Ser Lys Lys Glu Lys Val Thr Ile Gln Asn Trp Phe Arg Glu
                805                 810                 815

Ala Asp Phe Ala Lys Glu Val Pro Asn Tyr Lys Ala Thr Lys Asp Glu
            820                 825                 830

Lys Ile Glu Glu Ile Ile Gly Gln Asn Gly Glu Arg Ile Thr Ser Lys
        835                 840                 845

Gln Val Asp Asp Leu Ile Ala Lys Gly Asn Gly Lys Ile Thr Gln Asp
    850                 855                 860

Glu Leu Ser Lys Val Val Asp Asn Tyr Glu Leu Leu Lys His Ser Lys
865                 870                 875                 880

Asn Val Thr Asn Ser Leu Asp Lys Leu Ile Ser Ser Val Ser Ala Phe
                885                 890                 895

Thr Ser Ser Asn Asp Ser Arg Asn Val Leu Val Ala Pro Thr Ser Met
            900                 905                 910

Leu Asp Gln Ser Leu Ser Ser Leu Gln Phe Ala Arg Gly Ser
        915                 920                 925


<210> SEQ ID NO 8
<211> LENGTH: 4
<212> TYPE: PRT
<213> ORGANISM: Artificial Sequence
<220> FEATURE:
<223> OTHER INFORMATION: Synthetic peptide

<400> SEQUENCE: 8

Tyr Tyr Arg Pro
1


<210> SEQ ID NO 9
<211> LENGTH: 4
<212> TYPE: PRT
<213> ORGANISM: Artificial Sequence
<220> FEATURE:
<223> OTHER INFORMATION: Synthetic peptide

<400> SEQUENCE: 9

Val Tyr Tyr Arg
```

1

<210> SEQ ID NO 10
<211> LENGTH: 5
<212> TYPE: PRT
<213> ORGANISM: Artificial Sequence
<220> FEATURE:
<223> OTHER INFORMATION: Synthetic peptide

<400> SEQUENCE: 10

Val Tyr Tyr Arg Pro
1               5

<210> SEQ ID NO 11
<211> LENGTH: 5
<212> TYPE: PRT
<213> ORGANISM: Artificial Sequence
<220> FEATURE:
<223> OTHER INFORMATION: Synthetic peptide

<400> SEQUENCE: 11

Gln Val Tyr Tyr Arg
1               5

<210> SEQ ID NO 12
<211> LENGTH: 6
<212> TYPE: PRT
<213> ORGANISM: Artificial Sequence
<220> FEATURE:
<223> OTHER INFORMATION: Synthetic peptide

<400> SEQUENCE: 12

Gln Val Tyr Tyr Arg Pro
1               5

<210> SEQ ID NO 13
<211> LENGTH: 7
<212> TYPE: PRT
<213> ORGANISM: Artificial Sequence
<220> FEATURE:
<223> OTHER INFORMATION: Synthetic peptide

<400> SEQUENCE: 13

Gln Val Tyr Tyr Arg Pro Val
1               5

<210> SEQ ID NO 14
<211> LENGTH: 6
<212> TYPE: PRT
<213> ORGANISM: Artificial Sequence
<220> FEATURE:
<223> OTHER INFORMATION: Synthetic peptide

<400> SEQUENCE: 14

Asn Gln Val Tyr Tyr Arg
1               5

<210> SEQ ID NO 15
<211> LENGTH: 7
<212> TYPE: PRT
<213> ORGANISM: Artificial Sequence
<220> FEATURE:
<223> OTHER INFORMATION: Synthetic peptide

<400> SEQUENCE: 15

Asn Gln Val Tyr Tyr Arg Pro
1               5

```
<210> SEQ ID NO 16
<211> LENGTH: 8
<212> TYPE: PRT
<213> ORGANISM: Artificial Sequence
<220> FEATURE:
<223> OTHER INFORMATION: Synthetic peptide

<400> SEQUENCE: 16

Asn Gln Val Tyr Tyr Arg Pro Val
1               5


<210> SEQ ID NO 17
<211> LENGTH: 8
<212> TYPE: PRT
<213> ORGANISM: Artificial Sequence
<220> FEATURE:
<223> OTHER INFORMATION: Synthetic peptide

<400> SEQUENCE: 17

Pro Asn Gln Val Tyr Tyr Arg Pro
1               5


<210> SEQ ID NO 18
<211> LENGTH: 9
<212> TYPE: PRT
<213> ORGANISM: Artificial Sequence
<220> FEATURE:
<223> OTHER INFORMATION: Synthetic peptide

<400> SEQUENCE: 18

Pro Asn Gln Val Tyr Tyr Arg Pro Val
1               5


<210> SEQ ID NO 19
<211> LENGTH: 5
<212> TYPE: PRT
<213> ORGANISM: Artificial Sequence
<220> FEATURE:
<223> OTHER INFORMATION: Synthetic peptide

<400> SEQUENCE: 19

Tyr Tyr Arg Pro Met
1               5


<210> SEQ ID NO 20
<211> LENGTH: 5
<212> TYPE: PRT
<213> ORGANISM: Artificial Sequence
<220> FEATURE:
<223> OTHER INFORMATION: Synthetic peptide

<400> SEQUENCE: 20

Tyr Tyr Arg Pro Val
1               5


<210> SEQ ID NO 21
<211> LENGTH: 6
<212> TYPE: PRT
<213> ORGANISM: Artificial Sequence
<220> FEATURE:
<223> OTHER INFORMATION: Synthetic peptide

<400> SEQUENCE: 21

Val Tyr Tyr Arg Pro Met
1               5
```

<210> SEQ ID NO 22
<211> LENGTH: 6
<212> TYPE: PRT
<213> ORGANISM: Artificial Sequence
<220> FEATURE:
<223> OTHER INFORMATION: Synthetic peptide

<400> SEQUENCE: 22

Val Tyr Tyr Arg Pro Val
1 5

<210> SEQ ID NO 23
<211> LENGTH: 7
<212> TYPE: PRT
<213> ORGANISM: Artificial Sequence
<220> FEATURE:
<223> OTHER INFORMATION: Synthetic peptide

<400> SEQUENCE: 23

Gln Val Tyr Tyr Arg Pro Met
1 5

<210> SEQ ID NO 24
<211> LENGTH: 8
<212> TYPE: PRT
<213> ORGANISM: Artificial Sequence
<220> FEATURE:
<223> OTHER INFORMATION: Synthetic peptide

<400> SEQUENCE: 24

Asn Gln Val Tyr Tyr Arg Pro Met
1 5

<210> SEQ ID NO 25
<211> LENGTH: 24
<212> TYPE: PRT
<213> ORGANISM: Artificial Sequence
<220> FEATURE:
<223> OTHER INFORMATION: Synthetic peptide

<400> SEQUENCE: 25

Tyr Tyr Arg Tyr Tyr Arg Tyr Tyr Arg Tyr Tyr Arg Tyr Tyr Arg Tyr
1 5 10 15

Tyr Arg Tyr Tyr Arg Tyr Tyr Arg
20

<210> SEQ ID NO 26
<211> LENGTH: 36
<212> TYPE: PRT
<213> ORGANISM: Artificial Sequence
<220> FEATURE:
<223> OTHER INFORMATION: Synthetic peptide

<400> SEQUENCE: 26

Tyr Tyr Arg Arg Tyr Tyr Arg Tyr Tyr Tyr Tyr Arg Arg Tyr Tyr Arg
1 5 10 15

Tyr Tyr Tyr Tyr Arg Arg Tyr Tyr Arg Tyr Tyr Tyr Tyr Arg Arg Tyr
20 25 30

Tyr Arg Tyr Tyr
35

<210> SEQ ID NO 27
<211> LENGTH: 40
<212> TYPE: PRT
<213> ORGANISM: Artificial Sequence
<220> FEATURE:
<223> OTHER INFORMATION: Synthetic peptide

<400> SEQUENCE: 27

Val Tyr Tyr Arg Pro Val Tyr Tyr Arg Pro Val Tyr Tyr Arg Pro Val
1               5                   10                  15

Tyr Tyr Arg Pro Val Tyr Tyr Arg Pro Val Tyr Tyr Arg Pro Val Tyr
            20                  25                  30

Tyr Arg Pro Val Tyr Tyr Arg Pro
        35                  40

<210> SEQ ID NO 28
<211> LENGTH: 60
<212> TYPE: PRT
<213> ORGANISM: Artificial Sequence
<220> FEATURE:
<223> OTHER INFORMATION: Synthetic peptide

<400> SEQUENCE: 28

Val Tyr Tyr Arg Pro Pro Arg Tyr Tyr Val Pro Arg Tyr Tyr Val Val
1               5                   10                  15

Tyr Tyr Arg Pro Pro Arg Tyr Tyr Val Pro Arg Tyr Tyr Val Val Tyr
            20                  25                  30

Tyr Arg Pro Pro Arg Tyr Tyr Val Pro Arg Tyr Tyr Val Val Tyr Tyr
        35                  40                  45

Arg Pro Pro Arg Tyr Tyr Val Pro Arg Tyr Tyr Val
    50                  55                  60

<210> SEQ ID NO 29
<211> LENGTH: 56
<212> TYPE: PRT
<213> ORGANISM: Artificial Sequence
<220> FEATURE:
<223> OTHER INFORMATION: Synthetic peptide

<400> SEQUENCE: 29

Gln Val Tyr Tyr Arg Pro Val Gln Val Tyr Tyr Arg Pro Val Gln Val
1               5                   10                  15

Tyr Tyr Arg Pro Val Gln Val Tyr Tyr Arg Pro Val Gln Val Tyr Tyr
            20                  25                  30

Arg Pro Val Gln Val Tyr Tyr Arg Pro Val Gln Val Tyr Tyr Arg Pro
        35                  40                  45

Val Gln Val Tyr Tyr Arg Pro Val
    50                  55

<210> SEQ ID NO 30
<211> LENGTH: 84
<212> TYPE: PRT
<213> ORGANISM: Artificial Sequence
<220> FEATURE:
<223> OTHER INFORMATION: Synthetic peptide

<400> SEQUENCE: 30

Gln Val Tyr Tyr Arg Pro Val Val Pro Arg Tyr Tyr Val Gln Val Pro
1               5                   10                  15

Arg Tyr Tyr Val Gln Gln Val Tyr Tyr Arg Pro Val Val Pro Arg Tyr
            20                  25                  30

Tyr Val Gln Val Pro Arg Tyr Tyr Val Gln Gln Val Tyr Tyr Arg Pro
        35                  40                  45

Val Val Pro Arg Tyr Tyr Val Gln Val Pro Arg Tyr Tyr Val Gln Gln
    50                  55                  60

```
Val Tyr Tyr Arg Pro Val Val Pro Arg Tyr Tyr Val Gln Val Pro Arg
65                  70                  75                  80

Tyr Tyr Val Gln


<210> SEQ ID NO 31
<211> LENGTH: 56
<212> TYPE: PRT
<213> ORGANISM: Artificial Sequence
<220> FEATURE:
<223> OTHER INFORMATION: Synthetic peptide

<400> SEQUENCE: 31

Asn Gln Val Tyr Tyr Arg Pro Asn Gln Val Tyr Tyr Arg Pro Asn Gln
1               5                   10                  15

Val Tyr Tyr Arg Pro Asn Gln Val Tyr Tyr Arg Pro Asn Gln Val Tyr
            20                  25                  30

Tyr Arg Pro Asn Gln Val Tyr Tyr Arg Pro Asn Gln Val Tyr Tyr Arg
        35                  40                  45

Pro Asn Gln Val Tyr Tyr Arg Pro
    50                  55


<210> SEQ ID NO 32
<211> LENGTH: 84
<212> TYPE: PRT
<213> ORGANISM: Artificial Sequence
<220> FEATURE:
<223> OTHER INFORMATION: Synthetic peptide

<400> SEQUENCE: 32

Asn Gln Val Tyr Tyr Arg Pro Pro Arg Tyr Tyr Val Gln Asn Pro Arg
1               5                   10                  15

Tyr Tyr Val Gln Asn Asn Gln Val Tyr Tyr Arg Pro Pro Arg Tyr Tyr
            20                  25                  30

Val Gln Asn Pro Arg Tyr Tyr Val Gln Asn Asn Gln Val Tyr Tyr Arg
        35                  40                  45

Pro Pro Arg Tyr Tyr Val Gln Asn Pro Arg Tyr Tyr Val Gln Asn Asn
    50                  55                  60

Gln Val Tyr Tyr Arg Pro Pro Arg Tyr Tyr Val Gln Asn Pro Arg Tyr
65                  70                  75                  80

Tyr Val Gln Asn


<210> SEQ ID NO 33
<211> LENGTH: 256
<212> TYPE: PRT
<213> ORGANISM: Mule Deer

<400> SEQUENCE: 33

Met Val Lys Ser His Ile Gly Ser Trp Ile Leu Val Leu Phe Val Ala
1               5                   10                  15

Met Trp Ser Asp Val Gly Leu Cys Lys Lys Arg Pro Lys Pro Gly Gly
            20                  25                  30

Gly Trp Asn Thr Gly Gly Ser Arg Tyr Pro Gly Gln Gly Ser Pro Gly
        35                  40                  45

Gly Asn Arg Tyr Pro Pro Gln Gly Gly Gly Gly Trp Gly Gln Pro His
    50                  55                  60

Gly Gly Gly Trp Gly Gln Pro His Gly Gly Gly Trp Gly Gln Pro His
65                  70                  75                  80

Gly Gly Gly Trp Gly Gln Pro His Gly Gly Gly Gly Trp Gly Gln Gly
```

```
                85                  90                  95

Gly Thr His Ser Gln Trp Asn Lys Pro Ser Lys Pro Lys Thr Asn Met
            100                 105                 110

Lys His Val Ala Gly Ala Ala Ala Ala Gly Ala Val Val Gly Gly Leu
        115                 120                 125

Gly Gly Tyr Met Leu Gly Ser Ala Met Ser Arg Pro Leu Ile His Phe
    130                 135                 140

Gly Asn Asp Tyr Glu Asp Arg Tyr Tyr Arg Glu Asn Met Tyr Arg Tyr
145                 150                 155                 160

Pro Asn Gln Val Tyr Tyr Arg Pro Val Asp Gln Tyr Asn Asn Gln Asn
                165                 170                 175

Thr Phe Val His Asp Cys Val Asn Ile Thr Val Lys Gln His Thr Val
            180                 185                 190

Thr Thr Thr Thr Lys Gly Glu Asn Phe Thr Glu Thr Asp Ile Lys Met
        195                 200                 205

Met Glu Arg Val Val Glu Gln Met Cys Ile Thr Gln Tyr Gln Arg Glu
    210                 215                 220

Ser Gln Ala Tyr Tyr Gln Arg Gly Ala Ser Val Ile Leu Phe Ser Ser
225                 230                 235                 240

Pro Pro Val Ile Leu Leu Ile Ser Phe Leu Ile Phe Leu Ile Val Gly
                245                 250                 255


<210> SEQ ID NO 34
<211> LENGTH: 256
<212> TYPE: PRT
<213> ORGANISM: Whitetail Deer

<400> SEQUENCE: 34

Met Val Lys Ser His Ile Gly Ser Trp Ile Leu Val Leu Phe Val Ala
1               5                   10                  15

Met Trp Ser Asp Val Gly Leu Cys Lys Lys Arg Pro Lys Pro Gly Gly
            20                  25                  30

Gly Trp Asn Thr Gly Gly Ser Arg Tyr Pro Gly Gln Gly Ser Pro Gly
        35                  40                  45

Gly Asn Arg Tyr Pro Pro Gln Gly Gly Gly Gly Trp Gly Gln Pro His
    50                  55                  60

Gly Gly Gly Trp Gly Gln Pro His Gly Gly Gly Trp Gly Gln Pro His
65                  70                  75                  80

Gly Gly Gly Trp Gly Gln Pro His Gly Gly Gly Gly Trp Gly Gln Gly
                85                  90                  95

Gly Thr His Ser Gln Trp Asn Lys Pro Ser Lys Pro Lys Thr Asn Met
            100                 105                 110

Lys His Val Ala Gly Ala Ala Ala Ala Gly Ala Val Val Gly Gly Leu
        115                 120                 125

Gly Gly Tyr Met Leu Gly Ser Ala Met Ser Arg Pro Leu Ile His Phe
    130                 135                 140

Gly Asn Asp Tyr Glu Asp Arg Tyr Tyr Arg Glu Asn Met Tyr Arg Tyr
145                 150                 155                 160

Pro Asn Gln Val Tyr Tyr Arg Pro Val Asp Gln Tyr Asn Asn Gln Asn
                165                 170                 175

Thr Phe Val His Asp Cys Val Asn Ile Thr Val Lys Gln His Thr Val
            180                 185                 190

Thr Thr Thr Thr Lys Gly Glu Asn Phe Thr Glu Thr Asp Ile Lys Met
        195                 200                 205
```

```
Met Glu Arg Val Val Glu Gln Met Cys Ile Thr Gln Tyr Gln Arg Glu
    210                 215                 220

Ser Gln Ala Tyr Tyr Gln Arg Gly Ala Ser Val Ile Leu Phe Ser Ser
225                 230                 235                 240

Pro Pro Val Ile Leu Leu Ile Ser Phe Leu Ile Phe Leu Ile Val Gly
                245                 250                 255


<210> SEQ ID NO 35
<211> LENGTH: 14
<212> TYPE: PRT
<213> ORGANISM: Artificial Sequence
<220> FEATURE:
<223> OTHER INFORMATION: Synthetic peptide

<400> SEQUENCE: 35

Gln Val Tyr Tyr Arg Pro Val Asp Gln Tyr Ser Asn Gln Asn
1               5                   10


<210> SEQ ID NO 36
<211> LENGTH: 168
<212> TYPE: PRT
<213> ORGANISM: Artificial Sequence
<220> FEATURE:
<223> OTHER INFORMATION: Synthetic peptide

<400> SEQUENCE: 36

Gln Val Tyr Tyr Arg Pro Val Asp Gln Tyr Ser Asn Gln Asn Asn Gln
1               5                   10                  15

Asn Ser Tyr Gln Asp Val Pro Arg Tyr Tyr Val Gln Asn Gln Asn Ser
            20                  25                  30

Tyr Gln Asp Val Pro Arg Tyr Tyr Val Gln Gln Val Tyr Tyr Arg Pro
        35                  40                  45

Val Asp Gln Tyr Ser Asn Gln Asn Asn Gln Asn Ser Tyr Gln Asp Val
    50                  55                  60

Pro Arg Tyr Tyr Val Gln Asn Gln Asn Ser Tyr Gln Asp Val Pro Arg
65                  70                  75                  80

Tyr Tyr Val Gln Gln Val Tyr Tyr Arg Pro Val Asp Gln Tyr Ser Asn
                85                  90                  95

Gln Asn Asn Gln Asn Ser Tyr Gln Asp Val Pro Arg Tyr Tyr Val Gln
            100                 105                 110

Asn Gln Asn Ser Tyr Gln Asp Val Pro Arg Tyr Tyr Val Gln Gln Val
        115                 120                 125

Tyr Tyr Arg Pro Val Asp Gln Tyr Ser Asn Gln Asn Asn Gln Asn Ser
    130                 135                 140

Tyr Gln Asp Val Pro Arg Tyr Tyr Val Gln Asn Gln Asn Ser Tyr Gln
145                 150                 155                 160

Asp Val Pro Arg Tyr Tyr Val Gln
                165


<210> SEQ ID NO 37
<211> LENGTH: 2794
<212> TYPE: DNA
<213> ORGANISM: Pasteurella haemolytica
<220> FEATURE:
<221> NAME/KEY: misc_feature
<223> OTHER INFORMATION: Reverse complement of SEQ ID NO: 6, shown in
      Fig. 11

<400> SEQUENCE: 37

catggctagc tagctaggat cccctagcaa attgaagaga agataaactt tgatccaaca      60
```

```
ttgaagttgg agccactaat acatttctcg aatcattaga cgaggtaaat gcacttacag    120
atgagattaa cttatctaag ctgtttgtca catttttgct atgtttgagc aattcatagt    180
tatcaacaac ttttgatagc tcatcttggg taattttgcc gttacctttt gcgataagat    240
catcaacttg ctttgaggtg atccgctcgc cattttgacc gatgatttct tcgattttct    300
catctttagt tgctttataa ttaggcactt ctttagcaaa atcagcctct cggaaccagt    360
tttgaatggt cactttctct tttttgctat tcgtgatgac aagattatgt ttaacttttt    420
caaatgttaa atcttttaag ttcgaatcag agaatgataa tttatcattg ccgtcagaat    480
cggtaataat atcattacca tcgcctttac ggtgaacgaa aatatcatcg cccttgccac    540
cgtgtaatag gtcgttgcct ttaccgccat cgataaaatc atcaccattt ccaccatcga    600
gaatatcatc gcctttacca ccaaataagc ggtcattgcc gtcgttaccg tcaatagtat    660
cgacaccatc accaccgtta aaggcatcat tgaacttact acctttaaag atatcgttat    720
gtgatgtacc gataatttct tcaacagctt tcaaggtatc tttggtgtaa taaccggcat    780
ggtgctggtt attgctatga cgatattcta ttttttcttc acggttgccc actaatgcgg    840
tatgggttga agtcacttcg tgtagtgctt taccggtttc tacgaaacga tttacggtat    900
aactaccttg ctcggtctct ttggttgcat caatagttaa agcaccatag tttccacggc    960
tatagtgaac tcggtcgtaa ccttcaccgc catcaatttc cgtcgtacca gaaccaacaa   1020
atacgttgtc atcaccttca ccaagtttgg caataatttt tgtttctttg gttttagtta   1080
catttccagc attgtctaat tcaataccaa tacgctgaac aacgttagtt aaatcaaagg   1140
tagaacttgc tgcaccatct gtaattttcc agctatctac acggttaata ttgagcttgg   1200
taatatattc atatttacct gtttgtacgc gttcacgatg ctctgttccc ggcgtcaata   1260
atggcgttct gaataagata tgctgagttt tcgctttacc cgaattactc acatcaataa   1320
taccgtttgc cgaatccaac tgtactaatt tatcggcttt aatgtgtttg ccttcttcaa   1380
acgcatccac ataggcttta ccactaagga ctttttcacc taaacggcta ataccagcta   1440
aatcaccaat gttgttatcc cattgctgct gagtaatagc gatgacacgt tctgcctgta   1500
actctttgtt taagttcagt aagaatttca tattatcttg taaattcgca agataacggg   1560
catcgtaacc attttcaaag tagttcttac cgtgattatt tttttcccat tctacaattt   1620
tgttatgaat tttatttgca acgtgctcaa acattgcttg tttagaatat tgcagaatcg   1680
tagaaattac accggtaatc ccagatacta ataaggcaat cggtgaagca ataaccgagc   1740
cggctgcagc agcagacaca ccaccagcaa tagcggccaa tgcggtatta attgcagtaa   1800
ccgatgcatc aatagtccct gttccccgct gatattctgc taataaatta tctccgtcat   1860
agcctaattt tttaaagcgt tcggcataac tctctaaact ttttgcatga ttaaatttat   1920
cggcaatacc ggcaaatgct aatgggctaa tcgcaagaga aacagtagaa gcaattaaag   1980
cagccacagg cccagttgaa gataaacctg ctgcaacacg ttgggctaaa atgtaagaag   2040
aaacggcttt ggtaatatta ccaacaactt ggtttgccaa ttcaaaaccc gcacccactt   2100
ttttagctgt tgaagcattt ttatctgcaa gtacaagtgc agctgttgcg cccgataata   2160
gccctgagat aacatctaaa ccaaggccag ctttatcaag tccaccgata tttttgagtt   2220
tgtctcctaa agtccctaag cctttgatat tttgtagttt tgaaccaaat tgactaattt   2280
gctcaccaaa ttcgtcaagt gtttttactg aattagcaat attttcaatt aatgaatttg   2340
ttagctccaa gccagcttta gcaagagcat gttggttgct gttattctgt aaggcctcat   2400
ctaaatccat tccagccaat actgagccta aaatagattg aatgccagat aatacagttt   2460
```

```
tggctttatt tgcattttgt acaatgcttt cggcagaacc taatgcttgg cctgctttag   2520

ttttctgtag caatttatca atttgtggag cggataacac aatgccacgc tcagttaagc   2580

caatagcggt ttgaatcgtg cctaaactgg tttgagctgt tgcaatatta ttgcgttctt   2640

ctctttgtac ctcaatcccc aactcttcgg ccgctttgac taaatcctgt aaaccattac   2700

cttgttcagt atcatattgg taattttggg gaatatagag gataattttt tttgccccag   2760

tttttgggaa gcttagatct ataacagtag ccat                               2794


<210> SEQ ID NO 38
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(6)
<223> OTHER INFORMATION: Any Xaa is Lys, Asp, Val or Asn

<400> SEQUENCE: 38

Gly Gly Xaa Gly Xaa Asp
1               5
```

PRION EPITOPES AND METHODS OF USE THEREOF

CROSS-REFERENCE TO RELATED APPLICATION

This application claims the benefit under 35 U.S.C. §119 (e)(1) to U.S. Provisional Application No. 61/125,507, filed Apr. 25, 2008, which application is incorporated herein by reference in its entirety.

TECHNICAL FIELD

The present invention pertains generally to prion diseases and immunogenic compositions and methods for treating, preventing and diagnosing prion infection. In particular, the invention relates to particular prion epitopes that display enhanced immunogenicity, and uses thereof.

BACKGROUND

Prion diseases represent a category of neurodegenerative disorders. Prion diseases of humans and domestic animals include Creutzfeldt-Jakob disease (CJD) in humans, scrapie in sheep and goats, bovine spongiform encephalopathy (BSE) in cattle, chronic wasting disease in deer and elk, transmissible encephalopathy in mink, and spongiform encephalopathy in domestic and feral cats (Silveira et al., Curr. *Top. Microbiol. Immunol*. (2004) 284:1-50). These diseases are transmitted primarily by the oral route and it appears initiation and progression of the disease is based on the misfolding of a normal cellular protein ($PrP^C$) into a self-propagating and infectious conformation, ($PrP^{Sc}$).

$PrP^{Sc}$ is thought to serve as a template to recruit normal cellular prion protein ($PrP^C$) to the infectious form of $PrP^{Sc}$ in an autocatalytic process (Prusiner S. B., *Proc. Nat. Acad. Sci. USA* (1998) 95:13363-13383). Transmission of $PrP^{Sc}$ within a population is believed to occur primarily through either environmental contamination by infected body fluids or by recycling of animal proteins within the food chain. For example, BSE is believed to be the result of cannibalism in which faulty industrial practices produce prion-contaminated feed for cattle. There is now considerable concern that bovine prions may have been passed to humans, resulting in a new form of CJD.

Efforts to eliminate BSE transmission have focused primarily on the removal of animal protein from ruminant feeds (Smith et al., *Br. Med. Bull*. (2003) 66:185-198). However, the occurrence of BSE in cattle following the elimination of feed exposure has raised concerns regarding persistent environmental contamination by $PrP^{Sc}$. The persistence of $PrP^{Sc}$ in the environment means that new strategies are required to minimize the risk of animal exposure or infection when animals are housed in a contaminated environment. Furthermore, strategies may be required to eliminate or minimize the risk of a $PrP^{Sc}$ shedding into the environment.

The pathogenesis of scrapie and BSE has been studied using a variety of experimental models and it is evident that prion diseases can be orally transmitted in sheep (Heggebo et al., *J. Gen. Virol*. (2000) 81:2327-2337), cattle (Terry et al., *Vet. Rec*. (2003) 152:387-392) and possibly cervids (Sigurdson et al., *J. Gen. Virol*. (2001) 82:2327-2334). These animal models have consistently revealed that following oral challenge, $PrP^{Sc}$ can be detected in mucosa-associated lymphoid tissues (MALT) which include the tonsils, and Peyer's patches within the small intestine. It appears that these tissues function as a primary site of prion propagation before the $PrP^{Sc}$ is transported by splanchic innervation to the brainstem and spinal cord (Sigurdson et al., *Br. Med. Bull*. (2003) 66:199-212; Marsh et al., *Rev. Sci. Tech*. (1992) 11:539-550).

The follicular dendritic cell, which is present within the lymphoid follicles of MALT, lymph nodes, and the spleen, appears to be of particular importance in the peripheral propagation of $PrP^{Sc}$ (Mabbott et al., *J. Virol*. (2003) 77:6845-6854). These cells are long-lived, express high levels of $PrP^C$, and are specialized to trap, retain, and present antigen. The tingible body macrophage, which is also present within lymphoid follicles, may also play a role in regulating prion disease by degrading $PrP^{Sc}$ (Jeffrey et al., *J. Pathol*. (2000) 191:323-332). Thus, lymphoid tissues provide a critical link in the pathogenesis of prion diseases and may also provide a site where the balance between the generation and destruction of $PrP^{Sc}$ may be altered through the application of immunoprophylaxis.

Several investigations have confirmed that antibodies directed against $PrP^C$ can clear cell lines infected with $PrP^{Sc}$ (Enari et al., *Proc. Natl. Acad. Sci. USA* (2001) 98:9295-9299; Peretz et al., *Nature* (2001) 412:739-743). These observations have been interpreted as evidence that antibodies may be able to interfere with the intermolecular interactions between $PrP^C$ or the compartmental cycling of this protein and thereby disrupt the conversion of $PrP^C$ to $PrP^{Sc}$. However, antibodies directed against $PrP^C$, a normal cell surface protein, may have adverse consequences in vivo. For example, circulating antibodies against $PrP^C$ may trigger complement-dependent lysis of cells or possibly induce autoimmune disease by breaking tolerance to this molecule. Alternatively, antibodies directed against $PrP^C$ may impair or alter the function of this normal cellular protein by either triggering apoptosis in neurons (White et al., *Am J. Pathol*. (1999) 155:1723-1730) or inappropriate activation of cell signaling cascades (Cashman et al., *Cell* (1999) 61:185-192; Mouillet-Richard et al., *Science* (2000) 289:1925-1928).

It has been demonstrated that the conversion of recombinant mouse prion protein to a β-sheet enriched form is accompanied by increased solvent exposure of tyrosine (Y) side chains (Paramithiotis et al., *Nat. Med*. (2003) 9:893-899). Six of the 11 Y residues in the protease-resistant core region of $PrP^{Sc}$ are present in conserved bi-tyrosine pairs in mouse, hamster, sheep, bovine, human, elk, mule deer and whitetail deer PrP. Two bi-tyrosine pairs [YY], located in the helix one and β-strand two, are in conjunction with a C-terminal arginine [R] which creates a YYR motif, (FIG. 1). U.S. Pat. No. 7,041,807 describes rabbit polyclonal antisera raised against YYR peptide and immunoprecipitation of $PrP^{Sc}$ from scrapie-infected mouse brain but did not $PrP^C$ from uninfected brains. Furthermore, a series of murine monoclonal antibodies (mAbs) specific for the YYR motif were reported as capable of immunoprecipitating $PrP^{Sc}$ from scrapie infected mouse and hamster brains, scrapie infected sheep brain, and BSE-infected bovine brain. These anti-$PrP^{Sc}$ antibodies were raised using YYR peptide formulated in conventional adjuvants in animals expressing endogenous $PrP^C$. Furthermore, neither the rabbit polyclonal antisera or the murine mAbs displayed a detectable reaction with surface proteins on normal cells.

In spite of the considerable potential of the YYR epitope in generating antibody responses that are specific to $PrP^{Sc}$ its application as a vaccine target is restricted by the limited immunogenicity of this motif. As $PrP^C$ is widely expressed, and in particular at the surfaces of B and T cells, wild-type animals are highly tolerant of antigens of $PrP^C$ making it difficult to induce potent antibody responses. This is of particular importance as the ability for antibodies to function as prion therapeutics is directly related to their titer (White et al., *Nature* (2003) 422:80-83). As such, the ability to induce robust and sustained antibody responses is believed to be a critical determinant of vaccine efficacy.

Thus, there remains a need for the development of effective strategies for the treatment, prevention and diagnosis of prion infection.

SUMMARY OF THE INVENTION

The invention relates to prion-derived peptides, polynucleotides encoding these peptides, and antibodies generated using these peptides. The peptides display enhanced immunogenicity over that displayed by the YYR epitope and induce robust, $PrP^{Sc}$-specific antibody responses. Thus, the peptides, polynucleotides, and/or antibodies described herein are useful in compositions and methods for treating and preventing prion diseases, as well as for detecting the presence of pathogenic prions, for example in a biological sample.

Due to the specificity of the antibodies directed against peptides of the invention, the risk of adverse effects that may occur using $PrP^{C}$-specific immunoprophylaxis is reduced. Moreover, the uptake and destruction of infectious prions by cells, such as tingible body macrophages may be enhanced, before they become completely resistant to proteases. Furthermore, $PrP^{Sc}$-specific antibodies may impair the interaction between $PrP^{c}$ and $PrP^{Sc}$ which is a prerequisite for the recruitment process to form prion protein.

Accordingly, in one embodiment, the invention is directed to an immunogenic peptide comprising the amino acid sequence NQVYYRP (SEQ ID NO:15).

In another embodiment, the invention is directed to an immunogenic peptide comprising two or more repeats of the amino acid sequence VYYRP (SEQ ID NO:10) in a linear or an inverted orientation.

In certain embodiments, the peptide comprises two or more repeats of the amino acid sequence QVYYRP (SEQ ID NO:12) in a linear or an inverted orientation, or two or more repeats of the amino acid sequence QVYYRPV (SEQ ID NO:13) in a linear or an inverted orientation, or two or more repeats of the amino acid sequence NQVYYRP (SEQ ID NO:15) in a linear or an inverted orientation, or two or more repeats of the amino acid sequence QVYYRPVDQYSNQN (SEQ ID NO:35) in a linear or an inverted orientation, or an amino acid sequence selected from the group consisting of SEQ ID NOS:27-32 and 36.

In some embodiments, any of the peptides above can be linked to a carrier molecule, such as a carrier molecule capable of enhancing the immunogenicity of the immunogenic peptide. In certain embodiments, the carrier molecule is RTX toxin, such a leukotoxin polypeptide, including but not limited to LKT 352.

In additional embodiments, the invention is directed to a composition comprising any of the immunogenic peptides described above and a pharmaceutically acceptable vehicle.

In further embodiments, the invention is directed to a method of producing a composition comprising combining one or more of the immunogenic peptides described above with a pharmaceutically acceptable vehicle.

In another embodiment, the invention is directed to a polynucleotide comprising a coding sequence encoding any one of the immunogenic peptides described above.

In a further embodiment, the invention is directed to a recombinant vector comprising:

(a) a polynucleotide as described above; and (b) control elements that are operably linked to said polynucleotide whereby the coding sequence can be transcribed and translated in a host cell.

In additional embodiments, the invention is directed to host cells transformed with the recombinant vector.

In further embodiments, the invention is directed to methods of producing an immunogenic peptide comprising:

(a) providing a population of host cells as described above; and (b) culturing the population of cells under conditions whereby the peptide encoded by the coding sequence present in the recombinant vector is expressed.

In another embodiment, the invention is directed to a composition comprising a polynucleotide as described above and a pharmaceutically acceptable vehicle.

In additional embodiments, the invention is directed to methods of producing a composition comprising combining a polynucleotide as described above with a pharmaceutically acceptable vehicle.

In further embodiments, the invention is directed to antibodies specific for an immunogenic peptide as described above, such as polyclonal or monoclonal antibodies.

In additional embodiments, the invention is directed to compositions comprising the antibodies and a pharmaceutically acceptable vehicle.

In another embodiment, the invention is directed to methods of producing a composition comprising combining the antibodies above with a pharmaceutically acceptable vehicle.

In additional embodiments, the invention is directed to a method of treating or preventing a prion disease comprising administering a therapeutic amount of any one of the compositions detailed above.

In a further embodiment, the invention is directed to a method of detecting prion antibodies in a biological sample comprising:

(a) providing a biological sample;

(b) reacting the biological sample with an immunogenic peptide as described above under conditions which allow prion antibodies, when present in the biological sample, to bind to the immunogenic peptide to form an antibody/antigen complex; and (c) detecting the presence or absence of the complex, thereby detecting the presence or absence of prion antibodies in said sample.

In another embodiment, the invention is directed to immunodiagnostic test kits for detecting prion infection, the test kits comprising an immunogenic peptide as described above, and instructions for conducting the immunodiagnostic test.

These and other embodiments of the subject invention will readily occur to those of skill in the art in view of the disclosure herein.

BRIEF DESCRIPTION OF THE FIGURES

FIG. 1 shows an alignment of the PrP protein from sheep (SEQ ID NO:1), bovine (SEQ ID NO:2), human (SEQ ID NO:3), mouse (SEQ ID NO:4), elk (SEQ NO:5), mule deer (SEQ ID NO:33), and whitetail deer (SEQ ID NO:34). The conserved YYR motifs are boxed. The second box in the figure represents the β-strand two YYR region.

FIG. 3A shows anti-Lkt titers (squares) and anti-SN1 titers (circles) and FIG. 3B shows anti-SN1 titers.

FIG. 4A shows median antibody titers using SN2 (circles), SN4 (squares), SN6 (triangles) and SN8 (inverted triangles). FIGS. 4B-4E show antibody titers produced using SN2 (4B), SN4 (4C), SN6 (4D) and SN8 (4E).

FIGS. 11A-11I (SEQ ID NOS:6, 7 and 37) show the nucleotide sequence and predicted amino acid sequence of leukotoxin 352 (LKT 352) from plasmid pAA352. Both the structural gene for LKT 352 and the sequences of the flanking vector regions are shown.

DETAILED DESCRIPTION OF THE INVENTION

Figure 2A:
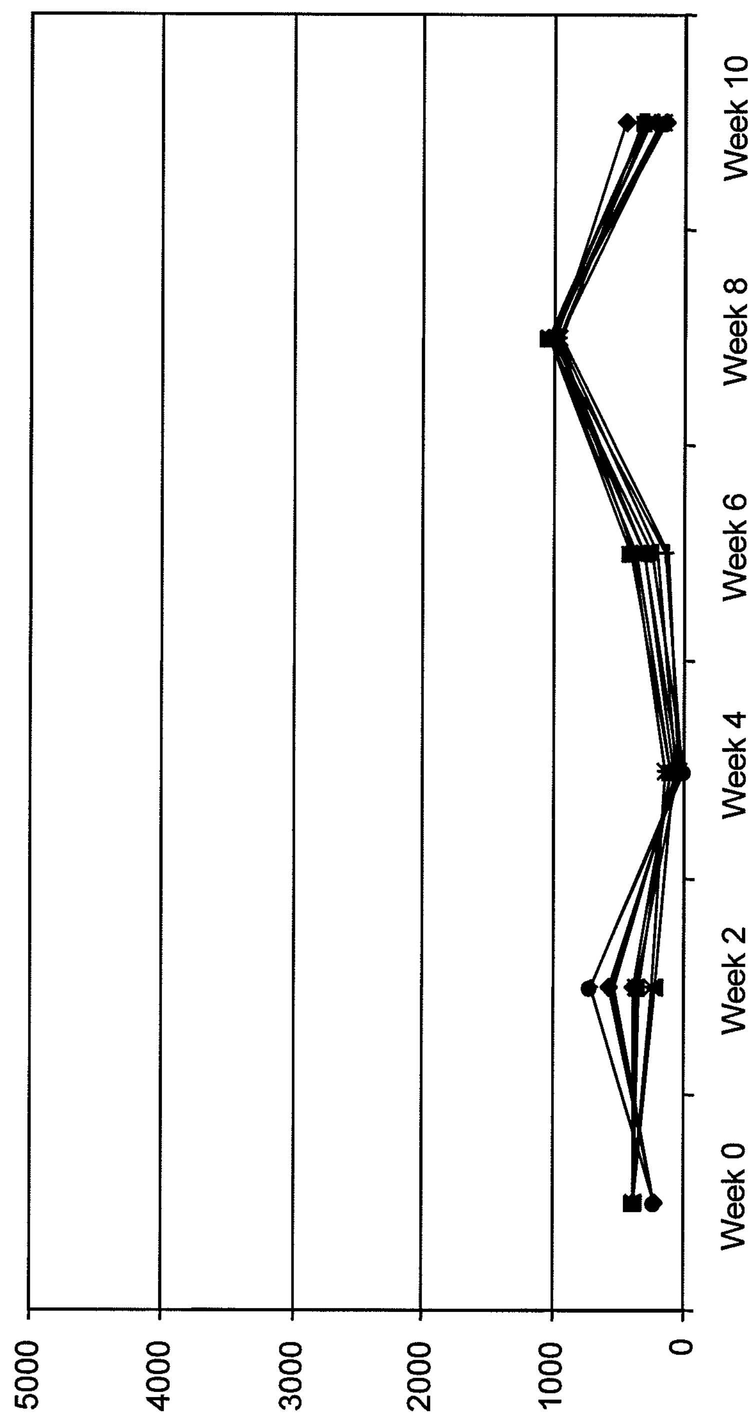
FIGS. 2A and 2B show antibody titers of mice immunized with either KLH-YYR (FIG. 2A) or Lkt-YYR (FIG. 2B). Each line corresponds to an individual animal.

The practice of the present invention will employ, unless otherwise indicated, conventional methods of chemistry, biochemistry, recombinant DNA techniques and immunology, within the skill of the art. Such techniques are explained fully in the literature. See, e.g., *Handbook of Experimental Immunology*, Vols. I-IV (D. M. Weir and C. C. Blackwell eds., Blackwell Scientific Publications); T. E. Creighton, *Proteins: Structures and Molecular Properties* (W.H. Freeman and Company); A. L. Lehninger, *Biochemistry* (Worth Publishers, Inc.); Sambrook, et al., *Molecular Cloning: A Laboratory Manual; Methods In Enzymology* (S. Colowick and N. Kaplan eds., Academic Press, Inc.); *Remington's Pharmaceutical Sciences*, (Easton, Pa.: Mack Publishing Company; *Methods In Enzymology* (S. Colowick and N. Kaplan, eds., Academic Press, Inc.

All publications, patents and patent applications cited herein, whether supra or infra, are hereby incorporated by reference in their entireties.

The following amino acid abbreviations are used throughout the text:

| | | | |
|---|---|---|---|
| Alanine: | Ala (A) | Arginine: | Arg (R) |
| Asparagine: | Asn (N) | Aspartic acid: | Asp (D) |
| Cysteine: | Cys (C) | Glutamine: | Gln (Q) |
| Glutamic acid: | Glu (E) | Glycine: | Gly (G) |
| Histidine: | His (H) | Isoleucine: | Ile (I) |
| Leucine: | Leu (L) | Lysine: | Lys (K) |
| Methionine: | Met (M) | Phenylalanine: | Phe (F) |
| Proline: | Pro (P) | Serine: | Ser (S) |
| Threonine: | Thr (T) | Tryptophan: | Trp (W) |
| Tyrosine: | Tyr (Y) | Valine: | Val (V) |

1. DEFINITIONS

In describing the present invention, the following terms will be employed, and are intended to be defined as indicated below.

It must be noted that, as used in this specification and the appended claims, the singular forms “a”, “an” and “the” include plural referents unless the content clearly dictates otherwise. Thus, for example, reference to “a peptide” includes a mixture of two or more such peptides, and the like.

As used herein, the term “prion” refers to a proteinaceous infectious agent that lacks nucleic acid. (See, e.g., Bolton, et al., *Science* (1982) 218:1309-1311; Prusiner, et al., *Biochemistry* (1982) 21:6942-6950; McKinley, et al. *Cell* (1983) 35:57-62; and Prusiner, *Proc. Natl. Acad. Sci. USA* (1998) 95:13363-13383. As explained above, the prion protein occurs normally in the nonpathogenic $PrP^C$ form and under appropriate conditions, is folded into the pathogenic $PrP^{Sc}$ form. The pathogenic conformation of the prion protein typically includes at least one region that can adapt a β-helical conformation (referred to as a “β-helical region”). Prions are naturally produced in a wide variety of mammalian species, including human, sheep, cattle, mice, deer, elk, among others.

By “prion disease” is meant a disease caused in whole or in part by a pathogenic prion particle ($PrP^{Sc}$). In humans these diseases include Creutzfeldt-Jakob disease (CJD), Gerstmann-Straussler-Scheinker syndrome (GSS), Fatal Familial Insomnia (FFI), and Kuru (see, e.g., Harrison's Principles of Internal Medicine, Isselbacher et al., eds., McGraw-Hill, Inc. New York, (1994); Medori et al., *N. Engl. J. Med*. (1992) 326: 444-449.). In non-human mammals, the diseases include sheep scrapie, bovine spongiform encephalopathy (BSE), transmissible mink encephalopathy, and chronic wasting disease of captive mule deer and elk (Gajdusek, (1990) Subacute Spongiform Encephalopathies: Transmissible Cerebral Amyloidoses Caused by Unconventional Viruses. Pp. 2289-2324 In: Virology, Fields, ed. New York: Raven Press, Ltd.).

The terms “polypeptide” and “protein” refer to a polymer of amino acid residues and are not limited to a minimum length of the product. Thus, peptides, oligopeptides, dimers, multimers, and the like, are included within the definition. Both full-length proteins and fragments thereof are encompassed by the definition. The terms also include postexpression modifications of the polypeptide, for example, glycosylation, acetylation, phosphorylation and the like. Furthermore, for purposes of the present invention, a “polypeptide” refers to a protein which includes modifications, such as deletions, additions and substitutions, to the native sequence, so long as the protein maintains the desired activity. These modifications may be deliberate, as through site-directed mutagenesis, or may be accidental, such as through mutations of hosts which produce the proteins or errors due to PCR amplification.

The term "peptide" as used herein refers to a fragment of a polypeptide. Thus, a peptide can include a C-terminal deletion, an N-terminal deletion and/or an internal deletion of the native polypeptide, so long as the entire protein sequence is not present. A peptide will generally include at least about 3-10 contiguous amino acid residues of the full-length molecule, and can include at least about 15-25 contiguous amino acid residues of the full-length molecule, or at least about 20-50 or more contiguous amino acid residues of the full-length molecule, or any integer between 3 amino acids and the number of amino acids in the full-length sequence, provided that the peptide in question retains the ability to elicit the desired biological response.

A prion "peptide" is a polypeptide that includes less than the full-length sequence of a prion protein. Moreover, a prion peptide will include at least one epitope such that an immunologic response can be generated. A prion peptide can be derived from any species, such as, but not limited to, any of the PrP sequences shown in FIG. 1. A prion peptide can include a portion of the native PrP sequence, repeats of a portion of the native sequence as linear repeats or inverted repeats in a symmetrical or asymmetrical orientation (discussed more fully below), or can include amino acid sequences from multiple species, or even non-prion sequences.

By "immunogenic" protein, polypeptide or peptide is meant a molecule which includes one or more epitopes and thus can modulate an immune response. Such peptides can be identified using any number of epitope mapping techniques, well known in the art. See, e.g., *Epitope Mapping Protocols* in Methods in Molecular Biology, Vol. 66 (Glenn E. Morris, Ed., 1996) Humana Press, Totowa, N.J. For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al. (1984) *Proc. Natl. Acad. Sci. USA* 81:3998-4002; Geysen et al. (1986) *Molec. Immunol.* 23:709-715, all incorporated herein by reference in their entireties. Similarly, conformational epitopes are readily identified by determining spatial conformation of amino acids such as by, e.g., x-ray crystallography and 2-dimensional nuclear magnetic resonance. See, e.g., *Epitope Mapping Protocols*, supra. Antigenic regions of proteins can also be identified using standard antigenicity and hydropathy plots, such as those calculated using, e.g., the Omiga version 1.0 software program available from the Oxford Molecular Group. This computer program employs the Hopp/Woods method, Hopp et al., *Proc. Natl. Acad. Sci. USA* (1981) 78:3824-3828 for determining antigenicity profiles, and the Kyte-Doolittle technique, Kyte et al., *J. Mol. Biol.* (1982) 157:105-132 for hydropathy plots.

Immunogenic peptides, for purposes of the present invention, will usually be at least about 2 amino acids in length, more preferably about 5 amino acids in length, and even at least about 10 to about 15 amino acids in length. There is no critical upper limit to the length of the peptide, which can comprise nearly the full-length of the protein sequence, or even a fusion protein comprising two or more epitopes.

As used herein, the term "epitope" generally refers to the site on an antigen which is recognized by a T-cell receptor and/or an antibody. Preferably it is a short peptide derived from or as part of a protein antigen. Several different epitopes may be carried by a single antigenic molecule. The term "epitope" also includes modified sequences of amino acids which stimulate responses which recognize the whole organism. The epitope can be generated from knowledge of the amino acid and corresponding DNA sequences of the peptide or polypeptide, as well as from the nature of particular amino acids (e.g., size, charge, etc.) and the codon dictionary, without undue experimentation. See, e.g., Ivan Roitt, Essential Immunology, 1988; Kendrew, supra; Janis Kuby, Immunology, 1992 e.g., pp. 79-81.

An "immunological response" to an antigen or composition is the development in a subject of a humoral and/or a cellular immune response to an antigen present in the composition of interest. For purposes of the present invention, a "humoral immune response" refers to an immune response mediated by antibody molecules, while a "cellular immune response" is one mediated by T-lymphocytes and/or other white blood cells. One important aspect of cellular immunity involves an antigen-specific response by cytolytic T-cells ("CTL"s). CTLs have specificity for peptide antigens that are presented in association with proteins encoded by the major histocompatibility complex (MHC) and expressed on the surfaces of cells. CTLs help induce and promote the destruction of intracellular microbes, or the lysis of cells infected with such microbes. Another aspect of cellular immunity involves an antigen-specific response by helper T-cells. Helper T-cells act to help stimulate the function, and focus the activity of, nonspecific effector cells against cells displaying peptide antigens in association with MHC molecules on their surface. A "cellular immune response" also refers to the production of cytokines, chemokines and other such molecules produced by activated T-cells and/or other white blood cells, including those derived from CD4+ and CD8+ T-cells.

Thus, an immunological response as used herein may be one that stimulates the production of antibodies. The antigen of interest may also elicit production of CTLs. Hence, an immunological response may include one or more of the following effects: the production of antibodies by B-cells; and/or the activation of suppressor T-cells and/or memory/effector T-cells directed specifically to an antigen or antigens present in the composition or vaccine of interest. These responses may serve to neutralize infectivity, and/or mediate antibody-complement, or antibody dependent cell cytotoxicity, (ADCC) to provide protection to an immunized host. Such responses can be determined using standard immunoassays and neutralization assays, well known in the art. (See, e.g., Montefiori et al. (1988) *J. Clin Microbiol.* 26:231-235; Dreyer et al. (1999) *AIDS Res Hum Retroviruses* (1999) 15(17):1563-1571). The innate immune system of mammals also recognizes and responds to molecular features of pathogenic organisms via activation of Toll-like receptors and similar receptor molecules on immune cells. Upon activation of the innate immune system, various non-adaptive immune response cells are activated to, e.g., produce various cytokines, lymphokines and chemokines. Cells activated by an innate immune response include immature and mature Dendritic cells of the monocyte and plasmacytoid lineage (MDC, PDC), as well as gamma, delta, alpha and beta T cells and B cells and the like. Thus, the present invention also contemplates an immune response wherein the immune response involves both an innate and adaptive response.

An "immunogenic composition" is a composition that comprises an immunogenic molecule where administration of the composition to a subject results in the development in the subject of a humoral and/or a cellular immune response to the molecule of interest.

An "antigen" refers to a molecule, such as a protein, polypeptide, or fragment thereof, containing one or more epitopes (either linear, conformational or both) that will stimulate a host's immune-system to make a humoral and/or cellular antigen-specific response. The term is used interchangeably with the term "immunogen." Antibodies such as anti-idiotype antibodies, or fragments thereof, and synthetic peptide mimotopes, which can mimic an antigen or antigenic determinant, are also captured under the definition of antigen as used herein. Similarly, an oligonucleotide or polynucleotide which expresses an antigen or antigenic determinant in vivo, such as in DNA immunization applications, is also included in the definition of antigen herein.

By "carrier" is meant any molecule which when associated with an antigen of interest, imparts immunogenicity to the antigen.

The term "RTX" toxin, as used herein refers to a protein belonging to the family of molecules characterized by the carboxy-terminus consensus amino acid sequence Gly-Gly-X-Gly-X-Asp (SEQ ID NO:38) (Highlander et al., *DNA* (1989) 8:15-28), where X is Lys, Asp, Val or Asn. Such proteins include, among others, leukotoxins derived from *P. haemolytica* and *Actinobacillus pleuropneumonias*, as well as *E. coli* alpha hemolysin (Strathdee et al., *Infect. Immun*. (1987) 55:3233-3236; Lo, *Can. J. Vet. Res*. (1990) 54:S33-S35; Welch, *Mol. Microbiol*. (1991) 5:521-528). This family of toxins is known as the "RTX" family of toxins (Lo, *Can. J. Vet. Res*. (1990) 54:S33-S35). In addition, the term "RTX toxin" refers to a member of the RTX family which is chemically synthesized, isolated from an organism expressing the same, or recombinantly produced. Furthermore, the term intends an immunogenic protein having an amino acid sequence substantially homologous to a contiguous amino acid sequence found in the particular native RTX molecule. Thus, the term includes both full-length and partial sequences, as well as analogues. Although native full-length RTX toxins display cytotoxic activity, the term "RTX toxin" also intends molecules which remain immunogenic yet lack the cytotoxic character of native molecules. In the chimeras produced according to the present invention, a selected RTX polypeptide sequence imparts enhanced immunogenicity to a fused prion peptide.

The term "leukotoxin polypeptide" or "LKT polypeptide" intends an RTX toxin derived from *P. haemolytica, Actinobacillus pleuropneumoniae*, among others, as defined above. The nucleotide sequences and corresponding amino acid sequences for several leukotoxins are known. See, e.g., U.S. Pat. Nos. 4,957,739 and 5,055,400; Lo et al., *Infect. Immun*. (1985) 50:667-67; Lo et al., *Infect. Immun*. (1987) 55:1987-1996; Strathdee et al., *Infect. Immun*. (1987) 55:3233-3236; Highlander et al., *DNA* (1989) 8:15-28; Welch, *Mol. Microbiol*. (1991) 5:521-528. A selected leukotoxin polypeptide sequence imparts enhanced immunogenicity to a fused prion peptide.

A prion peptide that is linked to a carrier displays "enhanced immunogenicity" when it possesses a greater capacity to elicit an immune response than the corresponding prion peptide alone. Such enhanced immunogenicity can be determined by administering the particular prion peptide/carrier complex and prion peptide controls to animals and comparing antibody titers against the two using standard assays such as radioimmunoassays and ELISAs, well known in the art.

"Substantially purified" generally refers to isolation of a substance (compound, polynucleotide, protein, polypeptide, polypeptide composition) such that the substance comprises the majority percent of the sample in which it resides. Typically in a sample, a substantially purified component comprises 50%, preferably 80%-85%, more preferably 90-95% of the sample. Techniques for purifying polynucleotides and polypeptides of interest are well-known in the art and include, for example, ion-exchange chromatography, affinity chromatography and sedimentation according to density.

By "isolated" is meant, when referring to a polypeptide, that the indicated molecule is separate and discrete from the whole organism with which the molecule is found in nature or is present in the substantial absence of other biological macro-molecules of the same type. The term "isolated" with respect to a polynucleotide is a nucleic acid molecule devoid, in whole or part, of sequences normally associated with it in nature; or a sequence, as it exists in nature, but having heterologous sequences in association therewith; or a molecule disassociated from the chromosome.

An "antibody" intends a molecule that "recognizes," i.e., specifically binds to an epitope of interest present in an antigen. By "specifically binds" is meant that the antibody interacts with the epitope in a "lock and key" type of interaction to form a complex between the antigen and antibody, as opposed to non-specific binding that might occur between the antibody and, for instance, components in a mixture that includes the test substance with which the antibody is reacted. Thus, an anti-prion peptide antibody is a molecule that specifically binds to an epitope of the prion peptide in question. The term "antibody" as used herein includes antibodies obtained from both polyclonal and monoclonal preparations, as well as, the following: hybrid (chimeric) antibody molecules (see, for example, Winter et al., *Nature* (1991) 349:293-299; and U.S. Pat. No. 4,816,567); F(ab')2 and F(ab) fragments; Fv molecules (non-covalent heterodimers, see, for example, Inbar et al., *Proc Natl Acad Sci USA* (1972) 69:2659-2662; and Ehrlich et al., *Biochem* (1980) 19:4091-4096); single-chain Fv molecules (sFv) (see, for example, Huston et al., *Proc Natl Acad Sci USA* (1988) 85:5879-5883); dimeric and trimeric antibody fragment constructs; minibodies (see, e.g., Pack et al., *Biochem* (1992) 31:1579-1584; Cumber et al., *J Immunology* (1992) 149B: 120-126); humanized antibody molecules (see, for example, Riechmann et al., *Nature* (1988) 332:323-327; Verhoeyan et al., *Science* (1988) 239:1534-1536; and U.K. Patent Publication No. GB 2,276,169, published 21 Sep. 1994); and, any functional fragments obtained from such molecules, wherein such fragments retain immunological binding properties of the parent antibody molecule.

As used herein, the term "monoclonal antibody" refers to an antibody composition having a homogeneous antibody population. The term is not limited regarding the species or source of the antibody, nor is it intended to be limited by the manner in which it is made. The term encompasses whole immunoglobulins as well as fragments such as Fab, $F(ab')_2$, Fv, and other fragments, as well as chimeric and humanized homogeneous antibody populations, that exhibit immunological binding properties of the parent monoclonal antibody molecule.

"Homology" refers to the percent identity between two polynucleotide or two polypeptide moieties. Two nucleic acid, or two polypeptide sequences are "substantially homologous" to each other when the sequences exhibit at least about 50% sequence identity, preferably at least about 75% sequence identity, more preferably at least about 80%-85% sequence identity, more preferably at least about 90% sequence identity, and most preferably at least about 95%-98% sequence identity over a defined length of the molecules. As used herein, substantially homologous also refers to sequences showing complete identity to the specified sequence.

In general, "identity" refers to an exact nucleotide-to-nucleotide or amino acid-to-amino acid correspondence of two polynucleotides or polypeptide sequences, respectively. Percent identity can be determined by a direct comparison of the sequence information between two molecules by aligning the sequences, counting the exact number of matches between the two aligned sequences, dividing by the length of the shorter sequence, and multiplying the result by 100. Readily available computer programs can be used to aid in the analysis, such as ALIGN, Dayhoff, M. O. in *Atlas of Protein Sequence and Structure* M. O. Dayhoff ed., 5 Suppl. 3:353-358, National biomedical Research Foundation, Washington, D.C., which adapts the local homology algorithm of Smith and Waterman *Advances in Appl. Math.* 2:482-489, 1981 for peptide analysis. Programs for determining nucleotide sequence identity are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent identity of a particular nucleotide sequence to a reference sequence can be determined using the homology algorithm of Smith and Waterman with a default scoring table and a gap penalty of six nucleotide positions.

Another method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs are readily available.

Alternatively, homology can be determined by hybridization of polynucleotides under conditions which form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *DNA Cloning*, supra; *Nucleic Acid Hybridization*, supra.

The terms "polynucleotide," "oligonucleotide," "nucleic acid" and "nucleic acid molecule" are used herein to include a polymeric form of nucleotides of any length, either ribonucleotides or deoxyribonucleotides. This term refers only to the primary structure of the molecule. Thus, the term includes triple-, double- and single-stranded DNA, as well as triple-, double- and single-stranded RNA. It also includes modifications, such as by methylation and/or by capping, and unmodified forms of the polynucleotide. More particularly, the terms "polynucleotide," "oligonucleotide," "nucleic acid" and "nucleic acid molecule" include polydeoxyribonucleotides (containing 2-deoxy-D-ribose), polyribonucleotides (containing D-ribose), any other type of polynucleotide which is an N- or C-glycoside of a purine or pyrimidine base, and other polymers containing nonnucleotidic backbones, for example, polyamide (e.g., peptide nucleic acids (PNAs)) and polymorpholino (commercially available from the Anti-Virals, Inc., Corvallis, Oreg., as Neugene) polymers, and other synthetic sequence-specific nucleic acid polymers providing that the polymers contain nucleobases in a configuration which allows for base pairing and base stacking, such as is found in DNA and RNA. There is no intended distinction in length between the terms "polynucleotide," "oligonucleotide," "nucleic acid" and "nucleic acid molecule," and these terms will be used interchangeably. Thus, these terms include, for example, 3'-deoxy-2',5'-DNA, oligodeoxyribonucleotide N3' P5' phosphoramidates, 2'-O-alkyl-substituted RNA, double- and single-stranded DNA, as well as double- and single-stranded RNA, DNA:RNA hybrids, and hybrids between PNAs and DNA or RNA, and also include known types of modifications, for example, labels which are known in the art, methylation, "caps," substitution of one or more of the naturally occurring nucleotides with an analog, internucleotide modifications such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalklyphosphoramidates, aminoalkylphosphotriesters), those containing pendant moieties, such as, for example, proteins (including nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide. In particular, DNA is deoxyribonucleic acid.

The term "derived from" is used herein to identify the original source of a molecule but is not meant to limit the method by which the molecule is made which can be, for example, by chemical synthesis or recombinant means.

"Recombinant" as used herein to describe a nucleic acid molecule means a polynucleotide of genomic, cDNA, viral, semisynthetic, or synthetic origin which, by virtue of its origin or manipulation is not associated with all or a portion of the polynucleotide with which it is associated in nature. The term "recombinant" as used with respect to a protein or polypeptide means a polypeptide produced by expression of a recombinant polynucleotide. In general, the gene of interest is cloned and then expressed in transformed organisms, as described further below. The host organism expresses the foreign gene to produce the protein under expression conditions.

"Recombinant host cells", "host cells," "cells", "cell lines," "cell cultures", and other such terms denoting microorganisms or higher eukaryotic cell lines cultured as unicellular entities refer to cells which can be, or have been, used as recipients for recombinant vector or other transferred DNA, and include the original progeny of the original cell which has been transfected.

A "coding sequence" or a sequence which "encodes" a selected polypeptide, is a nucleic acid molecule which is transcribed (in the case of DNA) and translated (in the case of mRNA) into a polypeptide in vivo when placed under the control of appropriate regulatory sequences (or "control elements"). The boundaries of the coding sequence can be determined by a start codon at the 5' (amino) terminus and a translation stop codon at the 3' (carboxy) terminus. A coding sequence can include, but is not limited to, cDNA from viral, procaryotic or eucaryotic mRNA, genomic DNA sequences from viral or procaryotic DNA, and even synthetic DNA sequences. A transcription termination sequence may be located 3' to the coding sequence.

Typical "control elements," include, but are not limited to, transcription promoters, transcription enhancer elements, transcription termination signals, polyadenylation sequences (located 3' to the translation stop codon), sequences for optimization of initiation of translation (located 5' to the coding sequence), and translation termination sequences. "Operably linked" refers to an arrangement of elements wherein the components so described are configured so as to perform their usual function. Thus, a given promoter operably linked to a coding sequence is capable of effecting the expression of the coding sequence when the proper enzymes are present. The promoter need not be contiguous with the coding sequence, so long as it functions to direct the expression thereof. Thus, for example, intervening untranslated yet transcribed sequences can be present between the promoter sequence and the coding sequence and the promoter sequence can still be considered "operably linked" to the coding sequence.

"Encoded by" refers to a nucleic acid sequence which codes for a polypeptide sequence, wherein the polypeptide sequence or a portion thereof contains an amino acid sequence of at least 3 to 5 amino acids, more preferably at least 8 to 10 amino acids, and even more preferably at least 15 to 20 or more amino acids from a polypeptide encoded by the nucleic acid sequence.

"Expression cassette" or "expression construct" refers to an assembly which is capable of directing the expression of the sequence(s) or gene(s) of interest. An expression cassette generally includes control elements, as described above, such as a promoter which is operably linked to (so as to direct transcription of) the sequence(s) or gene(s) of interest, and often includes a polyadenylation sequence as well. Within certain embodiments of the invention, the expression cassette described herein may be contained within a plasmid construct. In addition to the components of the expression cassette, the plasmid construct may also include, one or more selectable markers, a signal which allows the plasmid construct to exist as single-stranded DNA (e.g., a M13 origin of replication), at least one multiple cloning site, and a "mammalian" origin of replication (e.g., a SV40 or adenovirus origin of replication).

The term "transfection" is used to refer- to the uptake of foreign DNA by a cell. A cell has been "transfected" when exogenous DNA has been introduced inside the cell membrane. A number of transfection techniques are generally known in the art. See, e.g., Graham et al. (1973) *Virology,* 52:456, Sambrook et al. (1989) *Molecular Cloning, a laboratory manual*, Cold Spring Harbor Laboratories, New York, Davis et al. (1986) *Basic Methods in Molecular Biology*, Elsevier, and Chu et al. (1981) *Gene* 13:197. Such techniques can be used to introduce one or more exogenous DNA moieties into suitable host cells. The term refers to both stable and transient uptake of the genetic material, and includes uptake of peptide- or antibody-linked DNAs.

A "vector" is capable of transferring nucleic acid sequences to target cells (e.g., viral vectors, non-viral vectors, particulate carriers, and liposomes). Typically, "vector construct," "expression vector," and "gene transfer vector," mean any nucleic acid construct capable of directing the expression of a nucleic acid of interest and which can transfer nucleic acid sequences to target cells. Thus, the term includes cloning and expression vehicles, as well as viral vectors.

"Gene transfer" or "gene delivery" refers to methods or systems for reliably inserting DNA or RNA of interest into a host cell. Such methods can result in transient expression of non-integrated transferred DNA, extrachromosomal replication and expression of transferred replicons (e.g., episomes), or integration of transferred genetic material into the genomic DNA of host cells. Gene delivery expression vectors include, but are not limited to, vectors derived from bacterial plasmid vectors, viral vectors, non-viral vectors, alphaviruses, pox viruses and vaccinia viruses. When used for immunization, such gene delivery expression vectors may be referred to as vaccines or vaccine vectors.

As used herein, a "biological sample" refers to a sample of tissue or fluid isolated from a subject, including but not limited to, for example, blood, plasma, serum, fecal matter, urine, bone marrow, bile, spinal fluid, lymph fluid, samples of the skin, external secretions of the skin, respiratory, intestinal, and genitourinary tracts, tears, saliva, milk, blood cells, organs, biopsies and also samples of in vitro cell culture constituents including but not limited to conditioned media resulting from the growth of cells and tissues in culture medium, e.g., recombinant cells, and cell components.

By "vertebrate subject" is meant any member of the subphylum chordata, including, without limitation, humans and other primates, including non-human primates such as chimpanzees and other apes and monkey species; farm animals such as cattle, sheep, pigs, goats and horses; domestic mammals such as dogs and cats; non-domestic animals such as elk, deer, mink and feral cats; laboratory animals including rodents such as mice, rats and guinea pigs; birds, including domestic, wild and game birds such as chickens, turkeys and other gallinaceous birds, ducks, geese, and the like. The term does not denote a particular age. Thus, both adult and newborn individuals are intended to be covered.

By "therapeutically effective amount" in the context of the immunogenic compositions is meant an amount of an immunogen (e.g., a prion peptide) which will induce an immunological response, either for antibody production or for treatment or prevention of infection.

For purposes of the present invention, an "effective amount" of a carrier will be that amount which enhances an immunological response to a prion peptide.

As used herein, "treatment" refers to any of (i) the prevention of infection or reinfection, as in a traditional vaccine, or (ii) the reduction or elimination of symptoms from an infected individual. Treatment may be effected prophylactically (prior to infection) or therapeutically (following infection).

2. MODES OF CARRYING OUT THE INVENTION

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of methods and materials similar or equivalent to those described herein can be used in the practice of the present invention, the preferred materials and methods are described herein.

Prion isoform conversion occurs at the cell surface or a compartment close to the cell surface (Caughey et al., *J. Biol. Chem.* (1991) 27:18217-23; Borchelt et al., *J. Cell Biol.*

(1990) 110:743-52) which ensures that antibodies are able to interfere in this process. Thus, immunoprophylaxis can be used to prevent the infection of animals exposed to $PrP^{Sc}$. Alternatively, immunoprophylaxis following exposure of animals to feed or an environment contaminated with $PrP^{Sc}$ may effectively reduce the production of $PrP^{Sc}$ or increase its destruction within infected animals. In this way the shedding of $PrP^{Sc}$ by infected animals can be reduced or eliminated and the cycle of disease transmission can be broken.

The present invention thus provides immunological compositions and methods for treating and/or preventing prion disease. The invention is based on the discovery of prion-derived peptides that display enhanced immunogenicity over that displayed by the YYR epitope described in U.S. Pat. No. 7,041,807. The peptides of the present invention induce robust, $PrP^{Sc}$-specific antibody responses. Thus, the peptides, polynucleotides and/or antibodies described herein are useful in compositions and methods for treating and preventing prion diseases. Immunization can be achieved by any of the methods known in the art including, but not limited to, use of peptide vaccines or DNA immunization. Such methods are described in detail below. Moreover, the peptides described herein can be used for detecting the presence of pathogenic prions, for example in a biological sample.

In order to further an understanding of the invention, a more detailed discussion is provided below regarding the prion peptides, production thereof, compositions comprising the same, and methods of using such compositions in the treatment or prevention of prion infection, as well as in the diagnosis of infection.

A. Prion Peptides

The prion peptides of the invention include at least one epitope derived from the YYR (tyrosine-tyrosine-arginine) region of the prion PrP protein, and particularly, epitopes derived from the β-strand two YYR region, i.e., the region represented by the second box in FIG. 1. The peptides are preferably expansions and fusions of this region. In particular, the peptides typically include YYR and at least two additional flanking amino acids from the β-strand two YYR region, such as 2, 3, 4, 5, 6, 7, 8, 9, 10 . . . 15 . . . 20 or more flanking amino acids, but less than the full-length of the PrP protein. The expansion can be symmetrical, i.e., equal numbers of flanking amino acids, or asymmetrical, i.e., unequal numbers of flanking amino acids. Thus, for example, with reference to the bovine sequence in FIG. 1, the peptides of the invention can include sequences corresponding to YYRP (SEQ ID NO:8); VYYR (SEQ ID NO:9); VYYRP (SEQ ID NO:10); QVYYR (SEQ ID NO:11); QVYYRP (SEQ ID NO:12); QVYYRPV (SEQ ID NO:13); NQVYYR (SEQ ID NO:14); NQVYYRP (SEQ ID NO:15); NQVYYRPV (SEQ ID NO:16); PNQVYYRP (SEQ ID NO:17); PNQVYYRPV (SEQ ID NO:18); QVYYRPVDQYSNQN (SEQ ID NO:35), etc. The foregoing sequences are merely illustrative and prion peptides of the present invention can include additional flanking sequences from the YYR region as shown in FIG. 1. The flanking amino acids will be determined in part by the species of interest. Thus, for example, in humans, the peptides above may include YYRPM (SEQ ID NO:19) rather than YYRPV (SEQ ID NO:20), VYYRPM (SEQ ID NO:21) rather than VYYRPV (SEQ ID NO:22), QVYYRPM (SEQ ID NO:23) rather than QVYYRPV (SEQ ID NO:13), NQVYYRPM (SEQ ID NO:24) rather than NQVYYRPV (SEQ ID NO:16), and the like. According to the present invention, then, YYRPM (SEQ ID NO:19) is a sequence "corresponding to" YYRPV (SEQ ID NO:20), NQVYYRPM (SEQ ID NO:24) is a sequence "corresponding to" the sequence NQVYYRPV (SEQ ID NO:16), and the like.

Additionally, the peptides of the invention may include fusions of more than one prion peptide and the fusions may include the peptides present as linear repeats, in the same orientation, i.e., the C-terminal amino acid of the first prion peptide is fused to the N-terminal amino acid of the repeat of the prion peptide, the C-terminal amino acid of this repeat is fused to the N-terminal amino acid of the next repeat, etc. Alternatively, one or more of the repeats can be present in an inverted orientation, i.e., the C-terminal amino acid of the first prion peptide is fused to the C-terminal amino acid of the repeat of the prion peptide, etc. Representative fusions are shown in Table 1 in the Examples. As shown, prion peptide SN1 includes eight linear repeats of the YYR epitope and has the sequence YYRYYRYYRYYRYYRYYRYYRYYR (SEQ ID NO:25); SN2 includes 12 repeats of the YYR epitope, some of which are present in the inverted orientation and has the sequence YYRRYYRYYYYRRYYRYYYYR-RYYRYYYYRRYYRYY (SEQ ID NO:26); SN3 includes 8 linear repeats of the VYYRP (SEQ ID NO:10) peptide and has the sequence VYYRPVYYRPVYYRPVYYRPVYYR-PVYYRPVYYRPVYYRP (SEQ ID NO:27); SN4 includes 12 repeats of the VYYRP (SEQ ID NO:10) peptide, some of which are present in the inverted orientation and has the sequence VYYRPPRYYVPRYYVVYYRPPRYYVPRYYVVYYRPPRYYVPRYYVVYYRPPRYYVPRYYV (SEQ ID NO:28); SN5 includes eight linear repeats of the QVYYRPV (SEQ ID NO:13) peptide and has the sequence QVYYR-PVQVYYRPVQVYYRPVQVYYRPVQVYYR-PVQVYYRPVQVYYRPVQVYYRPV (SEQ ID NO:29); SN6 includes 12 repeats of the QVYYRPV (SEQ ID NO:13) peptide, some of which are present in the inverted orientation and has the sequence QVYYRPV-VPRYYVQVPRYYVQQVYYRPV-VPRYYVQVPRYYVQQVYYRPVVPRYYVQVPRYYVQQVYYRPVVPRYYVQVPRYYVQ (SEQ ID NO:30); SN7 includes 8 linear repeats of the NQVYYRP (SEQ ID NO:15) peptide and has the sequence NQVYYRP-NQVYYRPNQVYYRPNQVYYRPNQVYYRP-NQVYYRPNQVYYRPNQVYYRP (SEQ ID NO:31); SN8 includes 12 repeats of the NQVYYRP (SEQ ID NO:15) peptide, some of which are present in the inverted orientation and has the sequence NQVYYRPPRYYVQNPRYYVQN-NQVYYRPPRYYVQNPRYYVQNNQVYYRP-PRYYVQNPRYYVQNNQVYYRPPRYYVQNPRYYVQN (SEQ ID NO:32); SN6b includes 12 repeats of the QVYYR-PVDQYSNQN (SEQ ID NO:35) peptide, some of which are present in the inverted orientation and has the sequence QVYYRPVDQYSNQNNQNSYQD-VPRYYVQNQNSYQDVPRYYVQQVYYRPVDQYSNQNNQNSYQDVPRYYVQNQNSYQD-VPRYYVQQVYYRPVDQYSNQNNQNSYQDVPRYYVQNQNSYQDVPRYYVQQVYYR-PVDQYSNQNNQNSYQDVPRYYVQNQN-SYQDVPRYYVQ (SEQ ID NO:36). Prion peptides SN1-SN8 and SN6b are representative and it is to be understood that other fusions will find use in the present invention so long as the fusions are immunogenic, as described above.

The repeats present in the fusions can be derived from the same species or from different species in which prions are present. Moreover, there can be 2 or more repeats, such as 3, 4, 5, 6, 7, 8, 9, 10 . . . 15 . . . 20 . . . 25 or more repeats present.

Thus, the prion peptides may also correspond to a molecule of the general formula prion epitope-X-prion epitope, wherein X is selected from the group consisting of a peptide linkage, an amino acid spacer group and [prion epitope]$_n$, where n is greater than or equal to 1. Spacer sequences can be used between selected prion epitopes in order to confer increased immunogenicity on the subject constructs. Accordingly, a selected spacer sequence may encode a wide variety of moieties of one or more amino acids in length. Selected spacer groups may preferably provide enzyme cleavage sites so that the expressed fusions can be processed by proteolytic enzymes in vivo (by APC's or the like) to yield a number of peptides—each of which contain at least one epitope. Further, spacer groups may be constructed so that the junction region between selected prion epitopes comprises a clearly foreign sequence to the immunized subject, thereby conferring enhanced immunogenicity upon the associated prion epitopes. Additionally, spacer sequences may be constructed so as to provide T-cell antigenicity, such as sequences which encode amphipathic and/or α-helical peptide sequences which are generally regarded in the art as providing immunogenic helper T-cell epitopes. In this regard, the choice of particular T-cell epitopes to be provided by such spacer sequences may vary depending on the particular vertebrate species to be vaccinated.

The prion peptides can be conjugated with a carrier molecule as discussed more fully below.

B. Prion Peptide Conjugates

In order to enhance immunogenicity of the prion peptides, the peptides may be conjugated with a carrier. By "carrier" is meant any molecule which when associated with an antigen of interest, imparts immunogenicity to the antigen. Examples of suitable carriers include large, slowly metabolized macromolecules such as: proteins; polysaccharides, such as sepharose, agarose, cellulose, cellulose beads and the like; polymeric amino acids such as polyglutamic acid, polylysine, and the like; amino acid copolymers; inactive virus particles; bacterial toxins such as tetanus toxoid, serum albumins, keyhole limpet hemocyanin, thyroglobulin, ovalbumin, sperm whale myoglobin, and other proteins well known to those skilled in the art. Other suitable carriers for the antigens of the present invention include VP6 polypeptides of rotaviruses, or functional fragments thereof, as disclosed in U.S. Pat. No. 5,071,651.

These carriers may be used in their native form or their functional group content may be modified by, for example, succinylation of lysine residues or reaction with Cys-thiolactone. A sulfhydryl group may also be incorporated into the carrier (or antigen) by, for example, reaction of amino functions with 2-iminothiolane or the N-hydroxysuccinimide ester of 3-(4-dithiopyridyl propionate. Suitable carriers may also be modified to incorporate spacer arms (such as hexamethylene diamine or other bifunctional molecules of similar size) for attachment of peptides.

Prion peptides can also be conjugated with a member of the RTX family of toxins (as described further below), such as a *Pasteurella haemolytica* leukotoxin (LKT) polypeptide. See, e.g., International Publication No. WO 93/08290, published 29 Apr. 1993, as well as U.S. Pat. Nos. 5,238,823, 5,273,889, 5,723,129, 5,837,268, 5,422,110, 5,708,155, 5,969,126, 6,022,960, 6,521,746 and 6,797,272, all incorporated herein by reference in their entireties.

Leukotoxin polypeptide carriers are derived from proteins belonging to the family of molecules characterized by the carboxy-terminus consensus amino acid sequence Gly-Gly-X-Gly-X-Asp (SEQ ID NO:38) (Highlander et al., *DNA* (1989) 8:15-28), where X is Lys, Asp, Val or Asn. Such proteins include, among others, leukotoxins derived from *P. haemolytica* and *Actinobacillus pleuropneumoniae*, as well as *E. coli* alpha hemolysin (Strathdee et al., *Infect. Immun.* (1987) 55:3233-3236; Lo, *Can. J. Vet. Res.* (1990) 54:S33-S35; Welch, *Mol. Microbiol.* (1991) 5:521-528). This family of toxins is known as the "RTX" family of toxins (Lo, *Can. J. Vet. Res.* (1990) 54:533-535). The nucleotide sequences and corresponding amino acid sequences for several leukotoxins are known. See, e.g., U.S. Pat. Nos. 4,957,739 and 5,055,400; Lo et al., *Infect. Immun.* (1985) 50:667-67; Lo et al., *Infect. Immun.* (1987) 55:1987-1996; Strathdee et al., *Infect. Immun.* (1987) 55:3233-3236; Highlander et al., *DNA* (1989) 8:15-28; Welch, *Mol. Microbiol.* (1991) 5:521-528. Particular examples of immunogenic leukotoxin polypeptides for use herein include LKT 342, LKT 352, LKT 111, LKT 326 and LKT 101 which are described in greater detail below.

By "LKT 352" is meant a protein which is derived from the lktA gene present in plasmid pAA352 (FIG. 10) and described in U.S. Pat. No. 5,476,657, incorporated herein by reference in its entirety. LKT 352 has an N-terminal truncation of the native leukotoxin sequence and includes amino acids 38-951 of the native molecule. Thus, the gene in plasmid pAA352 encodes a truncated leukotoxin, having 914 amino acids which lacks the cytotoxic portion of the molecule. The nucleotide and amino acid sequences of LKT 352 is shown in FIGS. 11A-11I.

By "LKT 111" is meant a leukotoxin polypeptide which is derived from the lktA gene present in plasmid pCB111. The plasmid and nucleotide sequence of this gene and the corresponding amino acid sequence are described in U.S. Pat. Nos. 5,723,129 and 5,969,126, incorporated herein by reference in their entireties. The gene encodes a shortened version of leukotoxin which was developed from the recombinant leukotoxin gene present in plasmid pAA352 by removal of an internal DNA fragment of approximately 1300 bp in length. The LKT 111 polypeptide has an estimated molecular weight of 52 kDa (as compared to the 99 kDa LKT 352 polypeptide), retains the ability to act as a carrier molecule, and contains convenient restriction sites for use in producing the fusion proteins of the present invention.

By "LKT 101" is meant a leukotoxin polypeptide which is derived from the lktA gene present in plasmid pAA101. The plasmid and sequence of LKT 101 is described in U.S. Pat. No. 5,476,657 (see FIG. 3 therein), incorporated herein by reference in its entirety. The LKT 101 polypeptide is expressed from a C-terminally truncated form of the lktA gene which contains the 5' end of the gene up to the unique Pst1 restriction endonuclease site. Thus, LKT 101 includes the first 377 amino acids of native, full-length, *P. haemolytica* leukotoxin.

By "LKT 342" is meant a leukotoxin polypeptide which is derived from the lktA gene present in plasmid pAA342, described in U.S. Pat. No. 5,476,657, incorporated herein in its entirety. LKT 342 has an N-terminal and C-terminal truncation of the native leukotoxin sequence and includes amino acids 38-334 of native leukotoxin.

The various LKT molecules described above are representative and other leukotoxin molecules which enhance the immunogenicity of the prion peptides will also find use herein. Moreover, the leukotoxin molecules need not be physically derived from the sequence present in the corresponding plasmids but may be generated in any manner, including for example, by chemical synthesis or recombinant production, as described below.

Additionally, the prion peptides can be fused to either the carboxyl or amino terminals or both of the carrier molecule, or at sites internal to the carrier.

Carriers can be physically conjugated to the prion peptides of interest, using standard coupling reactions. Alternatively, chimeric molecules can be prepared recombinantly for use in the present invention, such as by fusing a gene encoding a suitable polypeptide carrier to one or more copies of a gene, or fragment thereof, encoding for a selected prion peptide.

C. Production of Prion Peptides and Conjugates

The prion peptides described herein and conjugates with carrier molecules, can be prepared in any suitable manner (e.g. recombinant expression, purification from cell culture, chemical synthesis, etc.) and in various forms (e.g. native, mutant, fusions, etc.). Means for preparing such peptides and conjugates are well understood in the art. Peptides and conjugates are preferably prepared in substantially pure form (i.e. substantially free from other host cell or non host cell proteins).

The prion peptides and conjugates thereof can be conveniently synthesized chemically, by any of several techniques that are known to those skilled in the peptide art. In general, these methods employ the sequential addition of one or more amino acids to a growing peptide chain. Normally, either the amino or carboxyl group of the first amino acid is protected by a suitable protecting group. The protected or derivatized amino acid can then be either attached to an inert solid support or utilized in solution by adding the next amino acid in the sequence having the complementary (amino or carboxyl) group suitably protected, under conditions that allow for the formation of an amide linkage. The protecting group is then removed from the newly added amino acid residue and the next amino acid (suitably protected) is then added, and so forth. After the desired amino acids have been linked in the proper sequence, any remaining protecting groups (and any solid support, if solid phase synthesis techniques are used) are removed sequentially or concurrently, to render the final polypeptide. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide. See, e.g., J. M. Stewart and J. D. Young, *Solid Phase Peptide Synthesis* (Pierce Chemical Co., Rockford, Ill. 1984) and G. Barany and R. B. Merrifield, *The Peptides: Analysis, Synthesis, Biology*, editors E. Gross and J. Meienhofer, Vol. 2, (Academic Press, New York, 1980), pp. 3-254, for solid phase peptide synthesis techniques; and M. Bodansky, Principles of Peptide Synthesis, (Springer-Verlag, Berlin 1984) and E. Gross and J. Meienhofer, Eds., *The Peptides: Analysis, Synthesis, Biology*, Vol. 1, for classical solution synthesis.

Typical protecting groups include t-butyloxycarbonyl (Boc), 9-fluorenylmethoxycarbonyl (Fmoc) benzyloxycarbonyl (Cbz); p-toluenesulfonyl (Tx); 2,4-dinitrophenyl; benzyl (Bzl); biphenylisopropyloxycarboxy-carbonyl, t-amyloxycarbonyl, isobornyloxycarbonyl, o-bromobenzyloxycarbonyl, cyclohexyl, isopropyl, acetyl, o-nitrophenylsulfonyl and the like. Typical solid supports are cross-linked polymeric supports. These can include divinylbenzene cross-linked-styrene-based polymers, for example, divinylbenzene-hydroxymethylstyrene copolymers, divinylbenzene-chloromethylstyrene copolymers and divinylbenzene-benzhydrylaminopolystyrene copolymers.

The peptides of the present invention can also be chemically prepared by other methods such as by the method of simultaneous multiple peptide synthesis. See, e.g., Houghten *Proc. Natl. Acad. Sci. USA* (1985) 82:5131-5135; U.S. Pat. No. 4,631,211.

Alternatively, the above-described prion peptides and conjugates can be produced recombinantly. Once coding sequences for the desired proteins have been isolated or synthesized, they can be cloned into any suitable vector or replicon for expression. Numerous cloning vectors are known to those of skill in the art, and the selection of an appropriate cloning vector is a matter of choice. A variety of bacterial, yeast, plant, mammalian and insect expression systems are available in the art and any such expression system can be used. Optionally, a polynucleotide encoding these proteins can be translated in a cell-free translation system. Such methods are well known in the art.

Examples of recombinant DNA vectors for cloning and host cells which they can transform include the bacteriophage λ (*E. coli*), pBR322 (*E. coli*), pACYC177 (*E. coli*), pKT230 (gram-negative bacteria), pGV1106 (gram-negative bacteria), pLAFR1 (gram-negative bacteria), pME290 (non-*E. coli* gram-negative bacteria), pHV14 (*E. coli* and *Bacillus subtilis*), pBD9 (*Bacillus*), pIJ61 (*Streptomyces*), pUC6 (*Streptomyces*), YIp5 (*Saccharomyces*), YCp19 (*Saccharomyces*) and bovine papilloma virus (mammalian cells). See, generally, DNA Cloning: Vols. I & II, supra; Sambrook et al., supra; B. Perbal, supra.

Insect cell expression systems, such as baculovirus systems, can also be used and are known to those of skill in the art and described in, e.g., Summers and Smith, Texas Agricultural Experiment Station Bulletin No. 1555 (1987). Materials and methods for baculovirus/insect cell expression systems are commercially available in kit form from, inter alia, Invitrogen, San Diego Calif. ("MaxBac" kit).

Plant expression systems can also be used to produce the immunogenic proteins. Generally, such systems use virus-based vectors to transfect plant cells with heterologous genes. For a description of such systems see, e.g., Porta et al., Mol. Biotech. (1996) 5:209-221; and Hackiand et al., Arch. Virol. (1994) 139:1-22.

Viral systems, such as a vaccinia based infection/transfection system, as described in Tomei et al., J. Virol. (1993) 67:4017-4026 and Selby et al., J. Gen. Virol. (1993) 74:1103-1113, will also find use with the present invention. In this system, cells are first transfected in vitro with a vaccinia virus recombinant that encodes the bacteriophage T7 RNA polymerase. This polymerase displays exquisite specificity in that it only transcribes templates bearing T7 promoters. Following infection, cells are transfected with the DNA of interest, driven by a T7 promoter. The polymerase expressed in the cytoplasm from the vaccinia virus recombinant transcribes the transfected DNA into RNA which is then translated into protein by the host translational machinery. The method provides for high level, transient, cytoplasmic production of large quantities of RNA and its translation product(s).

The coding sequence can be placed under the control of a promoter, ribosome binding site (for bacterial expression) and, optionally, an operator (collectively referred to herein as "control" elements), so that the DNA sequence encoding the desired immunogenic peptide is transcribed into RNA in the host cell transformed by a vector containing this expression construction. The coding sequence may or may not contain a signal peptide or leader sequence. Leader sequences can be removed by the host in post-translational processing. See, e.g., U.S. Pat. Nos. 4,431,739; 4,425,437; 4,338,397.

Other regulatory sequences may also be desirable which allow for regulation of expression of the peptide sequences relative to the growth of the host cell. Such regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

The control sequences and other regulatory sequences may be ligated to the coding sequence prior to insertion into a vector. Alternatively, the coding sequence can be cloned directly into an expression vector which already contains the control sequences and an appropriate restriction site.

In some cases it may be necessary to modify the coding sequence so that it may be attached to the control sequences with the appropriate orientation; i.e., to maintain the proper reading frame. It may also be desirable to produce mutants or analogs of the immunogenic peptides. Mutants or analogs may be prepared by the deletion of a portion of the sequence encoding the peptide, by insertion of a sequence, and/or by substitution of one or more nucleotides within the sequence. Techniques for modifying nucleotide sequences, such as site-directed mutagenesis, are well known to those skilled in the art. See, e.g., Sambrook et al., supra; DNA Cloning, Vols. I and II, supra; Nucleic Acid Hybridization, supra.

The expression vector is then used to transform an appropriate host cell. A number of mammalian cell lines are known in the art and include immortalized cell lines available from the American Type Culture Collection (ATCC), such as, but not limited to, Chinese hamster ovary (CHO) cells, HeLa cells, baby hamster kidney (BHK) cells, monkey kidney cells (COS), human hepatocellular carcinoma cells (e.g., Hep G2), as well as others. Similarly, bacterial hosts such as *E. coli, Bacillus subtilis*, and *Streptococcus* spp., will find use with the present expression constructs. Yeast hosts useful in the present invention include inter alia, *Saccharomyces cerevisiae, Candida albicans, Candida maltosa, Hansenula polymorpha, Kluyveromyces fragilis, Kluyveromyces lactis, Pichia guillerimondii, Pichia pastoris, Schizosaccharomyces pombe* and *Yarrowia lipolytica*. Insect cells for use with baculovirus expression vectors include, inter alia, *Aedes aegypti, Autographa californica, Bomrbyx mori, Drosophila melanogaster, Spodoptera frugiperda*, and *Trichoplusia ni*.

Depending on the expression system and host selected, the peptides of the present invention are produced by growing host cells transformed by an expression vector described above under conditions whereby the protein of interest is expressed. The selection of the appropriate growth conditions is within the skill of the art. The cells are then disrupted, using chemical, physical or mechanical means, which lyse the cells yet keep the peptides substantially intact. Intracellular proteins can also be obtained by removing components from the cell wall or membrane, e.g., by the use of detergents or organic solvents, such that leakage of the immunogenic polypeptides occurs. Such methods are known to those of skill in the art and are described in, e.g., Protein Purification Applications: A Practical Approach, (E. L. V. Harris and S. Angal, Eds., 1990).

For example, methods of disrupting cells for use with the present invention include but are not limited to: sonication or ultrasonication; agitation; liquid or solid extrusion; heat treatment; freeze-thaw; desiccation; explosive decompression; osmotic shock; treatment with lytic enzymes including proteases such as trypsin, neuraminidase and lysozyme; alkali treatment; and the use of detergents and solvents such as bile salts, sodium dodecylsulphate, Triton TRITON, NP40 and CHAPS. The particular technique used to disrupt the cells is largely a matter of choice and will depend on the cell type in which the polypeptide is expressed, culture conditions and any pre-treatment used.

Following disruption of the cells, cellular debris is removed, generally by centrifugation, and the intracellularly produced peptide is further purified, using standard purification techniques such as but not limited to, column chromatography, ion-exchange chromatography, size-exclusion chromatography, electrophoresis, HPLC, immunoadsorbent techniques, affinity chromatography, immunoprecipitation, and the like.

For example, one method for obtaining the intracellular peptide of the present invention involves affinity purification, such as by immunoaffinity chromatography using specific antibodies. The choice of a suitable affinity resin is within the skill in the art. After affinity purification, the peptide can be further purified using conventional techniques well known in the art, such as by any of the techniques described above.

D. Prion Peptide Antibodies

The prion peptides of the present invention can be used to produce antibodies for therapeutic, diagnostic and purification purposes. These antibodies may be polyclonal or monoclonal antibody preparations, monospecific antisera, human antibodies, or may be hybrid or chimeric antibodies, such as humanized antibodies, altered antibodies, $F(ab')_2$ fragments, F(ab) fragments, Fv fragments, single-domain antibodies, dimeric or trimeric antibody fragment constructs, minibodies, or functional fragments thereof which bind to the antigen in question. Antibodies are produced using techniques well known to those of skill in the art and disclosed in, for example, U.S. Pat. Nos. 4,011,308; 4,722,890; 4,016,043; 3,876,504; 3,770,380; and 4,372,745.

For example, the prion peptides can be used to produce prion-specific polyclonal and monoclonal antibodies for use in diagnostic and detection assays, for purification and for use as therapeutics, such as for passive immunization. Such polyclonal and monoclonal antibodies specifically bind to the prion peptides in question. In particular, the prion peptides can be used to produce polyclonal antibodies by administering the peptide to a mammal, such as a mouse, a rat, a rabbit, a goat, or a horse. Serum from the immunized animal is collected and the antibodies are purified from the plasma by, for example, precipitation with ammonium sulfate, followed by chromatography, preferably affinity chromatography. Techniques for producing and processing polyclonal antisera are known in the art.

Mouse and/or rabbit monoclonal antibodies directed against epitopes present in the cell surface antigen can also be readily produced. In order to produce such monoclonal antibodies, the mammal of interest, such as a rabbit or mouse, is immunized, such as by mixing or emulsifying the antigen in saline, preferably in an adjuvant such as Freund's complete adjuvant ("FCA"), and injecting the mixture or emulsion parenterally (generally subcutaneously or intramuscularly). The animal is generally boosted 2-6 weeks later with one or more injections of the antigen in saline, preferably using Freund's incomplete adjuvant ("FIA").

Antibodies may also be generated by in vitro immunization, using methods known in the art. See, e.g., James et al., *J. Immunol. Meth*. (1987) 100:5-40.

Polyclonal antisera is then obtained from the immunized animal. However, rather than bleeding the animal to extract serum, the spleen (and optionally several large lymph nodes) is removed and dissociated into single cells. If desired, the spleen cells (splenocytes) may be screened (after removal of nonspecifically adherent cells) by applying a cell suspension to a plate or well coated with the antigen. B-cells, expressing membrane-bound immuno-globulin specific for the antigen, will bind to the plate, and are not rinsed away with the rest of the suspension. Resulting B-cells, or all dissociated splenocytes, are then induced to fuse with cells from an immortalized cell line (also termed a "fusion partner"), to form hybridomas. Typically, the fusion partner includes a property that allows selection of the resulting hybridomas using specific media. For example, fusion partners can be hypoxanthine/aminopterin/thymidine (HAT)-sensitive.

If rabbit-rabbit hybridomas are desired, the immortalized cell line will be from a rabbit. Such rabbit-derived fusion partners are known in the art and include, for example, cells of lymphoid origin, such as cells from a rabbit plasmacytoma as described in Spieker-Polet et al., *Proc. Natl. Acad. Sci. USA* (1995) 92:9348-9352 and U.S. Pat. No. 5,675,063, or the TP-3 fusion partner described in U.S. Pat. No. 4,859,595, incorporated herein by reference in their entireties. If a rabbit-mouse hybridoma or a rat-mouse or mouse-mouse hybridoma, or the like, is desired, the mouse fusion partner will be derived from an immortalized cell line from a mouse, such as a cell of lymphoid origin, typically from a mouse myeloma cell line. A number of such cell lines are known in the art and are available from the ATCC.

Fusion is accomplished using techniques well known in the art. Chemicals that promote fusion are commonly referred to as fusogens. These agents are extremely hydrophilic and facilitate membrane contact. One particularly preferred method of cell fusion uses polyethylene glycol (PEG). Another method of cell fusion is electrofusion. In this method, cells are exposed to a predetermined electrical discharge that alters the cell membrane potential. Additional methods for cell fusion include bridged-fusion methods. In this method, the antigen is biotinylated and the fusion partner is avidinylated. When the cells are added together, an antigen-reactive B cell-antigen-biotin-avidin-fusion partner bridge is formed. This permits the specific fusion of an antigen-reactive cell with an immortalizing cell. The method may additionally employ chemical or electrical means to facilitate cell fusion.

Following fusion, the cells are cultured in a selective medium (e.g., HAT medium). In order to enhance antibody secretion, an agent that has secretory stimulating effects can optionally be used, such as IL-6. See, e.g., Liguori et al., *Hybridoma* (2001) 20:189-198. The resulting hybridomas can be plated by limiting dilution, and are assayed for the production of antibodies which bind specifically to the immunizing antigen (and which do not bind to unrelated antigens). The selected monoclonal antibody-secreting hybridomas are then cultured either in vitro (e.g., in tissue culture bottles or hollow fiber reactors), or in vivo (e.g., as ascites in mice). For example, hybridomas producing prion peptide-specific antibodies can be identified using RIA or ELISA and isolated by cloning in semi-solid agar or by limiting dilution. Clones producing the desired antibodies can be isolated by another round of screening.

An alternative technique for generating the monoclonal antibodies of the present invention is the selected lymphocyte antibody method (SLAM). This method involves identifying a single lymphocyte that is producing an antibody with the desired specificity or function within a large population of lymphoid cells. The genetic information that encodes the specificity of the antibody (i.e., the immunoglobulin $V_H$ and $V_L$ DNA) is then rescued and cloned. See, e.g., Babcook et al., *Proc. Natl. Acad. Sci. USA* (1996) 93:7843-7848, for a description of this method.

For further descriptions of rabbit monoclonal antibodies and methods of making the same from rabbit-rabbit and rabbit-mouse fusions, see, e.g., U.S. Pat. No. 5,675,063 (rabbit-rabbit); U.S. Pat. No. 4,859,595 (rabbit-rabbit); U.S. Pat. No. 5,472,868 (rabbit-mouse); and U.S. Pat. No. 4,977,081 (rabbit-mouse). For a description of the production of conventional mouse monoclonal antibodies, see, e.g., Kohler and Milstein, *Nature* (1975) 256:495-497.

It may be desirable to provide chimeric antibodies. By "chimeric antibodies" is intended antibodies that are preferably derived using recombinant techniques and which comprise both human (including immunologically "related" species, e.g., chimpanzee) and non-human components. Such antibodies are also termed "humanized antibodies." Preferably, humanized antibodies contain minimal sequence derived from non-human immunoglobulin sequences. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. See, for example, U.S. Pat. Nos. 5,225,539; 5,585,089; 5,693,761; 5,693,762; 5,859,205. In some instances, framework residues of the human immunoglobulin are replaced by corresponding non-human residues (see, for example, U.S. Pat. Nos. 5,585,089; 5,693,761; 5,693,762). Furthermore, humanized antibodies may comprise residues that are not found in the recipient antibody or in the donor antibody. These modifications are made to further refine antibody performance (e.g., to obtain desired affinity). In general, the humanized antibody will comprise substantially all of at least one, and typically two, variable domains, in which all or substantially all of the hypervariable regions correspond to those of a non-human immunoglobulin and all or substantially all of the framework regions are those of a human immunoglobulin sequence. The humanized antibody optionally also will comprise at least a portion of an immunoglobulin constant region (Fc), typically that of a human immunoglobulin. For further details see Jones et al., *Nature* (1986) 331:522-525; Riechmann et al., *Nature* (1988) 332:323-329; and Presta, *Curr. Op. Struct. Biol.* (1992) 2:593-596.

Also encompassed are xenogeneic or modified antibodies produced in a non-human mammalian host, more particularly a transgenic mouse, characterized by inactivated endogenous immunoglobulin (Ig) loci. In such transgenic animals, competent endogenous genes for the expression of light and heavy subunits of host immunoglobulins are rendered-non-functional and substituted with the analogous human immunoglobulin loci. These transgenic animals produce human antibodies in the substantial absence of light or heavy host immunoglobulin subunits. See, for example, U.S. Pat. No. 5,939,598.

Antibody fragments which retain the ability to recognize the peptide of interest, will also find use herein. A number of antibody fragments are known in the art which comprise antigen-binding sites capable of exhibiting immunological binding properties of an intact antibody molecule. For example, functional antibody fragments can be produced by cleaving a constant region, not responsible for antigen binding, from the antibody molecule, using e.g., pepsin, to produce F(ab')2 fragments. These fragments will contain two antigen binding sites, but lack a portion of the constant region from each of the heavy chains. Similarly, if desired, Fab fragments, comprising a single antigen binding site, can be produced, e.g., by digestion of polyclonal or monoclonal antibodies with papain. Functional fragments, including only the variable regions of the heavy and light chains, can also be produced, using standard techniques such as recombinant production or preferential proteolytic cleavage of immunoglobulin molecules. These fragments are known as FV. See, e.g., Inbar et al., *Proc. Nat. Acad. Sci. USA* (1972) 69:2659-2662; Hochman et al., *Biochem.* (1976) 15:2706-2710; and Ehrlich et al., *Biochem.* (1980) 19:4091-4096.

A phage-display system can be used to expand antibody molecule populations in vitro. Saiki, et al., *Nature* (1986) 324:163; Scharf et al., *Science* (1986) 233:1076; U.S. Pat. Nos. 4,683,195 and 4,683,202; Yang et al., *J Mol. Biol.* (1995)

254:392; Barbas, III et al., *Methods: Comp. Meth Enzymol.* (1995) 8:94; Barbas, III et al., *Proc Natl Acad Sci USA* (1991) 88:7978.

Once generated, the phage display library can be used to improve the immunological binding affinity of the Fab molecules using known techniques. See, e.g., Figini et al., *J. Mol. Biol.* (1994) 239:68. The coding sequences for the heavy and light chain portions of the Fab molecules selected from the phage display library can be isolated or synthesized, and cloned into any suitable vector or replicon for expression. Any suitable expression system can be used, including those described above.

Single chain antibodies can also be produced. A single-chain Fv ("sFv" or "scFv") polypeptide is a covalently linked VH-VL heterodimer which is expressed from a gene fusion including VH- and VL-encoding genes linked by a peptide-encoding linker. Huston et al., *Proc. Nat. Acad. Sci. USA* (1988) 85:5879-5883. A number of methods have been described to discern and develop chemical structures (linkers) for converting the naturally aggregated, but chemically separated, light and heavy polypeptide chains from an antibody V region into an sFv molecule which will fold into a three dimensional structure substantially similar to the structure of an antigen-binding site. See, e.g., U.S. Pat. Nos. 5,091,513, 5,132,405 and 4,946,778. The sFv molecules may be produced using methods described in the art. See, e.g., Huston et al., *Proc. Nat. Acad. Sci. USA* (1988) 85:5879-5883; U.S. Pat. Nos. 5,091,513, 5,132,405 and 4,946,778. Design criteria include determining the appropriate length to span the distance between the C-terminus of one chain and the N-terminus of the other, wherein the linker is generally formed from small hydrophilic amino acid residues that do not tend to coil or form secondary structures. Such methods have been described in the art. See, e.g., U.S. Pat. Nos. 5,091,513, 5,132,405 and 4,946,778. Suitable linkers generally comprise polypeptide chains of alternating sets of glycine and serine residues, and may include glutamic acid and lysine residues inserted to enhance solubility.

"Mini-antibodies" or "minibodies" will also find use with the present invention. Minibodies are sFv polypeptide chains which include oligomerization domains at their C-termini, separated from the sFv by a hinge region. Pack et al., *Biochem.* (I 992) 31:1579-1584. The oligomerization domain comprises self-associating $\alpha$-helices, e.g., leucine zippers, that can be further stabilized by additional disulfide bonds. The oligomerization domain is designed to be compatible with vectorial folding across a membrane, a process thought to facilitate in vivo folding of the polypeptide into a functional binding protein. Generally, minibodies are produced using recombinant methods well known in the art. See, e.g., Pack et al., *Biochem.* (1992) 31:1579-1584; Cumber et al., *J. Immunology* (1992) 149B:120-126.

Polynucleotide sequences encoding the antibodies and immunoreactive fragments thereof, described above, are readily obtained using standard techniques, well known in the art, such as those techniques described above with respect to the recombinant production of the prion peptides.

For subjects known to have a prion disease, an anti-prion peptide antibody may have therapeutic benefit and can be used to confer passive immunity to the subject in question. Alternatively, antibodies can be used in diagnostic applications, described further below, as well as for purification of the prion peptides.

E. Compositions

The prion peptides, conjugates thereof, nucleic acids and/or antibodies, can be formulated into compositions for delivery to subjects for either inhibiting infection, or for enhancing an immune response to prion proteins. Compositions of the invention may comprise or be co-administered with a non-prion antigen or combination of antigens. Methods of preparing such formulations are described in, e.g., *Remington's Pharmaceutical Sciences*, Mack Publishing Company, Easton, Pa., 18 Edition, 1990. The compositions of the present invention can be prepared as injectables, either as liquid solutions or suspensions. Solid forms suitable for solution in or suspension in liquid vehicles prior to injection may also be prepared. The preparation may also be emulsified or the active ingredient encapsulated in liposome vehicles. The active immunogenic ingredient is generally mixed with a compatible pharmaceutical vehicle, such as, for example, water, saline, dextrose, glycerol, ethanol, or the like, and combinations thereof. In addition, if desired, the vehicle may contain minor amounts of auxiliary substances such as wetting or emulsifying agents and pH buffering agents.

If used to modulate an immune response, additional adjuvants which enhance the effectiveness of the composition may also be added to the formulation. Adjuvants may include for example, muramyl dipeptides, pyridine, aluminum hydroxide, dimethyldioctadecyl ammonium bromide (DDA), oils, oil-in-water emulsions, saponins, cytokines, and other substances known in the art.

The peptides may be used in their native form or their functional group content may be modified by, for example, succinylation of lysine residues or reaction with Cys-thiolactone. A sulfhydryl group may also be incorporated by, for example, reaction of amino functions with 2-iminothiolane or the N-hydroxysuccinimide ester of 3-(4-dithiopyridyl propionate.

Furthermore, the peptides and conjugates thereof may be formulated into compositions in either neutral or salt forms. Pharmaceutically acceptable salts include the acid addition salts (formed with the free amino groups of the active polypeptides) and which are formed with inorganic acids such as, for example, hydrochloric or phosphoric acids, or such organic acids as acetic, oxalic, tartaric, mandelic, and the like. Salts formed from free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

Injectable formulations will contain a "pharmaceutically effective amount" of the active ingredient, that is, an amount capable of achieving the desired response in a subject to which the composition is administered. In the treatment and prevention of prion disease, for example, a "pharmaceutically effective amount" would preferably be an amount which reduces or ameliorates the symptoms of the disease in question. The exact amount is readily determined by one skilled in the art using standard tests. The prion peptide, conjugate thereof and/or nucleic acid will typically range from about 1% to about 95% (w/w) of the composition, or even higher or lower if appropriate. With the present formulations, 1 μg to 2 mg, such as 100 μg to 1 mg, of active ingredient per ml of injected solution should be adequate to treat or prevent infection when a dose of 1 to 5 ml per subject is administered. If an adjuvant is used to enhance the immune response to co-delivered prion peptides or conjugates thereof, the amount of adjuvant delivered will generally be in the range of 2 ng to 5 mg, more generally 5 ng to 500 ng, for example 10 ng to 250 ng, or any amount within these stated ranges. The quantity to be administered depends on the subject to be treated, the capacity of the subject's immune system to synthesize antibodies, and the degree of protection desired. Effective dosages can be readily established by one of ordinary skill in the art through routine trials establishing dose response curves.

The composition can be administered parenterally, e.g., by intratracheal, intramuscular, subcutaneous, intraperitoneal, intravenous injection, or by delivery directly to the lungs, such as through aerosol administration. The subject is administered at least one dose of the composition. Moreover, the subject may be administered as many doses as is required to bring about the desired biological effect.

Additional formulations which are suitable for other modes of administration include suppositories and, in some cases, aerosol, intranasal, oral formulations, and sustained release formulations. For suppositories, the vehicle composition will include traditional binders and carriers, such as, polyalkaline glycols, or triglycerides. Such suppositories may be formed from mixtures containing the active ingredient in the range of about 0.5% to about 10% (w/w), preferably about 1% to about 2%. Oral vehicles include such normally employed excipients as, for example, pharmaceutical grades of mannitol, lactose, starch, magnesium, stearate, sodium saccharin cellulose, magnesium carbonate, and the like. These oral vaccine compositions may be taken in the form of solutions, suspensions, tablets, pills, capsules, sustained release formulations, or powders, and contain from about 10% to about 95% of the active ingredient, preferably about 25% to about 70%.

Intranasal formulations will usually include vehicles that neither cause irritation to the nasal mucosa nor significantly disturb ciliary function. Diluents such as water, aqueous saline or other known substances can be employed with the subject invention. The nasal formulations may also contain preservatives such as, but not limited to, chlorobutanol and benzalkonium chloride. A surfactant may be present to enhance absorption of the subject proteins by the nasal mucosa.

Controlled or sustained release formulations are made by incorporating the protein into carriers or vehicles such as liposomes, nonresorbable impermeable polymers such as ethylenevinyl acetate copolymers and HYTREL copolymers, swellable polymers such as hydrogels, resorbable polymers such as collagen and certain polyacids or polyesters such as those used to make resorbable sutures, polyphosphazenes, alginate, microparticles, gelatin nanospheres, chitosan nanoparticles, and the like. The prion peptide, conjugates and/or nucleic acids described herein can also be delivered using implanted mini-pumps, well known in the art.

Prime-boost methods can be employed where one or more compositions are delivered in a "priming" step and, subsequently, one or more compositions are delivered in a "boosting" step. In certain embodiments, priming and boosting with one or more compositions described herein is followed by additional boosting. The compositions delivered can include the same prion peptides or conjugates thereof, or different prion peptides or conjugates thereof, given in any order and via any administration route.

The prion peptides can also be administered via a carrier virus which expresses the same. Carrier viruses which will find use herein include, but are not limited to, the vaccinia and other pox viruses, adenovirus, and herpes virus. By way of example, vaccinia virus recombinants expressing the proteins can be constructed as follows. The DNA encoding a particular protein is first inserted into an appropriate vector so that it is adjacent to a vaccinia promoter and flanking vaccinia DNA sequences, such as the sequence encoding thymidine kinase (TK). This vector is then used to transfect cells which are simultaneously infected with vaccinia. Homologous recombination serves to insert the vaccinia promoter plus the gene encoding the desired immunogen into the viral genome. The resulting TK-recombinant can be selected by culturing the cells in the presence of 5-bromodeoxyuridine and picking viral plaques resistant thereto.

F. Nucleic Acid-Based Immunization Methods

Generally, nucleic acid-based vaccines for use with the present invention will include relevant regions encoding a prion peptide, with suitable control sequences and, optionally, ancillary therapeutic nucleotide sequences. The nucleic acid molecules are prepared in the form of vectors which include the necessary elements to direct transcription and translation in a recipient cell, as described above.

In order to augment an immune response in an immunized subject, the nucleic acid molecules can be administered in conjunction with ancillary substances, such as pharmacological agents, adjuvants, or in conjunction with delivery of vectors encoding biological response modifiers such as cytokines and the like.

Once prepared, the nucleic acid vaccine compositions can be delivered to the subject using known methods. In this regard, various techniques for immunization with antigen-encoding DNAs have been described. See, e.g., U.S. Pat. No. 5,589,466 to Felgner et al.; Tang et al. (1992) *Nature* 358:152; Davis et al. (1993) *Hum. Molec. Genet.* 2:1847; Ulmer et al. (1993) *Science* 258:1745; Wang et al. (1993) *Proc. Natl. Acad. Sci. USA* 90:4156; Eisenbraun et al. (1993) *DNA Cell Biol.* 12:791; Fynan et al. (1993) *Proc. Natl. Acad. Sci. USA* 90:12476; Fuller et al. (1994) *AIDS Res. Human Retrovir.* 10:1433; and Raz et al. (1994) *Proc. Natl. Acad. Sci. USA* 91:9519. General methods for delivering nucleic acid molecules to cells in vitro, for the subsequent reintroduction into the host, can also be used, such as liposome-mediated gene transfer. See, e.g., Hazinski et al. (1991) *Am. J. Respir. Cell Mol. Biol.* 4:206-209; Brigham et al. (1989) *Am. J. Med. Sci.* 298:278-281; Canonico et al. (1991) *Clin. Res.* 39:219 A; and Nabel et al. (1990) *Science* 249:1285-1288. Thus, the nucleic acid vaccine compositions can be delivered in either liquid or particulate form using a variety of known techniques. Typical vaccine compositions are described above.

G. Tests to Determine the Efficacy of an Immune Response

One way of assessing efficacy of therapeutic treatment involves monitoring infection after administration of a composition of the invention. One way of assessing efficacy of prophylactic treatment involves monitoring immune responses against the prion peptides in the compositions of the invention after administration of the composition.

Another way of assessing the immunogenicity of the component proteins of the immunogenic compositions of the present invention is to express the proteins recombinantly and to screen the subject's sera by immunoblot. A positive reaction between the protein and the serum indicates that the subject has previously mounted an immune response to the protein in question—that is, the protein is an immunogen. This method may also be used to identify immunodominant proteins and/or epitopes.

Another way of checking efficacy of therapeutic treatment involves monitoring infection after administration of the compositions of the invention. One way of checking efficacy of prophylactic treatment involves monitoring immune responses both systemically (such as monitoring the level of IgG1 and IgG2a production) and mucosally (such as monitoring the level of IgA production) against the antigens in the compositions of the invention after administration of the composition. Typically, serum-specific antibody responses are determined post-immunization but pre-challenge whereas mucosal specific antibody body responses are determined post-immunization and post-challenge. The immunogenic compositions of the present invention can be evaluated in in vitro and in vivo animal models prior to host administration.

The efficacy of immunogenic compositions of the invention can also be determined in vivo by challenging animal models of infection with the immunogenic compositions. The immunogenic compositions may or may not be derived from the same strains as the challenge strains. Preferably the immunogenic compositions are derivable from the same strains as the challenge strains.

The immune response may be one or both of a TH1 immune response and a TH2 response. The immune response may be an improved or an enhanced or an altered immune response. The immune response may be one or both of a systemic and a mucosal immune response. Preferably the immune response is an enhanced systemic and/or mucosal response.

An enhanced systemic and/or mucosal immunity is reflected in an enhanced TH1 and/or TH2 immune response. Preferably, the enhanced immune response includes an increase in the production of IgG1 and/or IgG2a and/or IgA. Preferably the mucosal immune response is a TH2 immune response. Preferably, the mucosal immune response includes an increase in the production of IgA.

Activated TH2 cells enhance antibody production and are therefore of value in responding to extracellular infections. Activated TH2 cells may secrete one or more of IL-4, IL-5, IL-6, and IL-10. A TH2 immune response may result in the production of IgG1, IgE, IgA and memory B cells for future protection.

A TH2 immune response may include one or more of an increase in one or more of the cytokines associated with a TH2 immune response (such as IL-4, IL-5, IL-6 and IL-10), or an increase in the production of IgG1, IgE, IgA and memory B cells. Preferably, the enhanced TH2 immune response will include an increase in IgG1 production.

A TH1 immune response may include one or more of an increase in CTLs, an increase in one or more of the cytokines associated with a TH1 immune response (such as IL-2, IFNγ, and TNFβ), an increase in activated macrophages, an increase in NK activity, or an increase in the production of IgG2a. Preferably, the enhanced TH1 immune response will include an increase in IgG2a production.

Immunogenic compositions of the invention, in particular, immunogenic composition comprising one or more antigens of the present invention may be used either alone or in combination with other antigens optionally with an immunoregulatory agent capable of eliciting a Th1 and/or Th2 response.

The immunogenic compositions of the invention will preferably elicit both a cell mediated immune response as well as a humoral immune response in order to effectively address an infection. This immune response will preferably induce long lasting (e.g., neutralizing) antibodies and a cell mediated immunity that can quickly respond upon exposure to one or more infectious antigens. By way of example, evidence of neutralizing antibodies in patient blood samples is considered as a surrogate parameter for protection.

H. Diagnostic Assays

Antibodies, produced as described above, can be used in vivo, i.e., injected into subjects suspected of having prion disease, for diagnostic or therapeutic uses. The use of antibodies for in vivo diagnosis is well known in the art. The label used will depend on the imaging modality chosen. Radioactive labels such as Indium-111, Technetium-99m, or Iodine-131 can be used for planar scans or single photon emission computed tomography (SPECT). Positron emitting labels such as Fluorine-19 can also be used for positron emission tomography (PET). For MRI, paramagnetic ions such as Gadolinium (III) or Manganese (II) can be used. Localization of the label within the patient allows determination of the presence of the disease.

The antibodies can also be used in standard in vitro immunoassays, to screen biological samples such as blood and/or tissues for the presence or absence of the infectious form of prions, $PrP^{Sc}$. Thus, the antibodies produced as described above, can be used in assays to diagnose prion disease. The antibodies can be used as either the capture component and/or the detection component in the assays, as described further below. Thus, the presence of prion disease can be determined by the presence of $PrP^{Sc}$ antigens and/or anti-prion peptide antibodies.

For example, the presence of $PrP^{Sc}$ antigens antigens can be detected using standard electrophoretic and immunodiagnostic techniques, including immunoassays such as competition, direct reaction, or sandwich type assays. Such assays include, but are not limited to, Western blots; agglutination tests; enzyme-labeled and mediated immunoassays, such as enzyme-linked immunosorbent assays ("ELISAs"); biotin/avidin type assays; radioimmunoassays; immunoelectrophoresis; immunoprecipitation, etc. The reactions generally include revealing labels such as fluorescent, chemiluminescent, radioactive, or enzymatic labels or dye molecules, or other methods for detecting the formation of a complex between the antigens and the antibodies described above.

Assays can also be conducted in solution, such that the antigens and antibodies thereto form complexes under precipitating conditions. The precipitated complexes can then be separated from the test sample, for example, by centrifugation. The reaction mixture can be analyzed to determine the presence or absence of antibody-antigen complexes using any of a number of standard methods, such as those immunodiagnostic methods described above.

I. Kits

The invention also provides kits comprising one or more containers of compositions of the invention. Compositions can be in liquid form or can be lyophilized, as can individual antigens. Suitable containers for the compositions include, for example, bottles, vials, syringes, and test tubes. Containers can be formed from a variety of materials, including glass or plastic. A container may have a sterile access port (for example, the container may be an intravenous solution bag or a vial having a stopper pierceable by a hypodermic injection needle).

The kit can further comprise a second container comprising a pharmaceutically-acceptable buffer, such as phosphate-buffered saline, Ringer's solution, or dextrose solution. It can also contain other materials useful to the end-user, including other pharmaceutically acceptable formulating solutions such as buffers, diluents, filters, needles, and syringes or other delivery device. The kit may further include a third component comprising an adjuvant.

The kit can also comprise a package insert containing written instructions for methods of inducing immunity or for treating infections. The package insert can be an unapproved draft package insert or can be a package insert approved by the Food and Drug Administration (FDA) or other regulatory body.

The invention also provides a delivery device pre-filled with the immunogenic compositions of the invention.

Similarly, antibodies can be provided in kits, with suitable instructions and other necessary reagents, in order to conduct immunoassays as described above. The kit can also contain, depending on the particular immunoassay used, suitable labels and other packaged reagents and materials (i.e. wash buffers and the like). Standard immunoassays, such as those described above, can be conducted using these kits.

3. EXPERIMENTAL

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Materials and Methods

Figure 10:
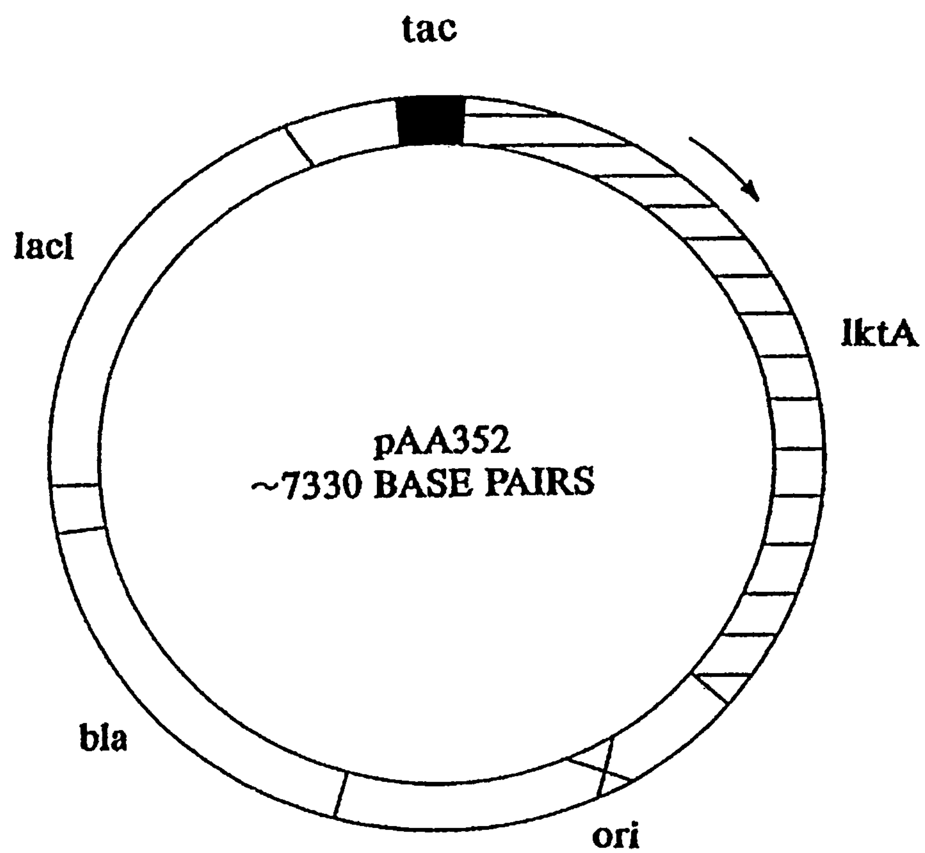
FIG. 10 depicts the structure of Plasmid pAA352 wherein tac is the hybrid trp::lac promoter from *E. coli*; bla represents the β-lactamase gene (ampicillin resistance); ori is the ColE1-based plasmid origin of replication; lktA is the *P. haemolytica* leukotoxin structural gene; and lac1 is the *E. coli* lac operon repressor. The direction of transcription/translation of the leukotoxin gene is indicated by the arrow. The size of each component is not drawn to scale.
Figures 12A, 12B:
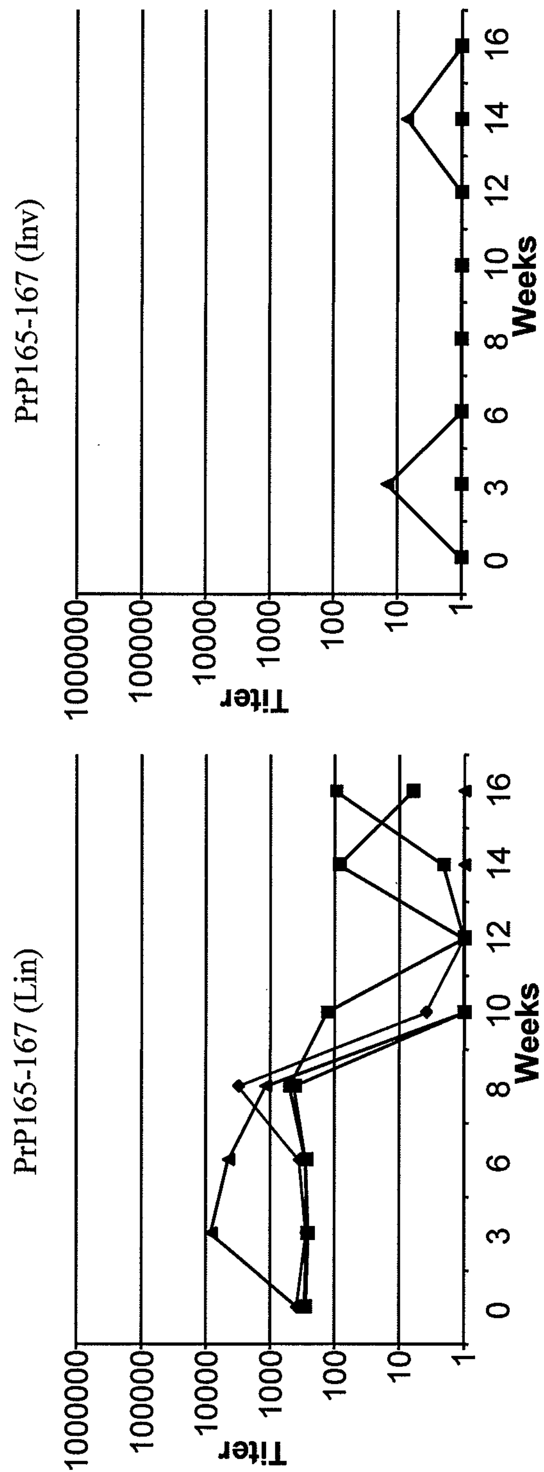
FIGS. 12A-12I show individual antibody titers in sheep immunized with PrP165-167 (Lin) (SN1, FIG. 12A); PrP165-167 (Inv) (SN2, FIG. 12B); PrP164-168 (Lin) (SN3, FIG. 12C); PrP164-168 (Inv) (SN4, FIG. 12D); PrP163-169 (Lin) (SN5, FIG. 12E); PrP163-169 (Inv) (SN6, FIG. 12F); PrP162-168 (Lin) (SN7, FIG. 12G); PrP162-168 (Inv) (SN8, FIG. 12H); PrP162-177 (Inv) (SN6b, FIG. 12I).
Figures 12C, 12D:
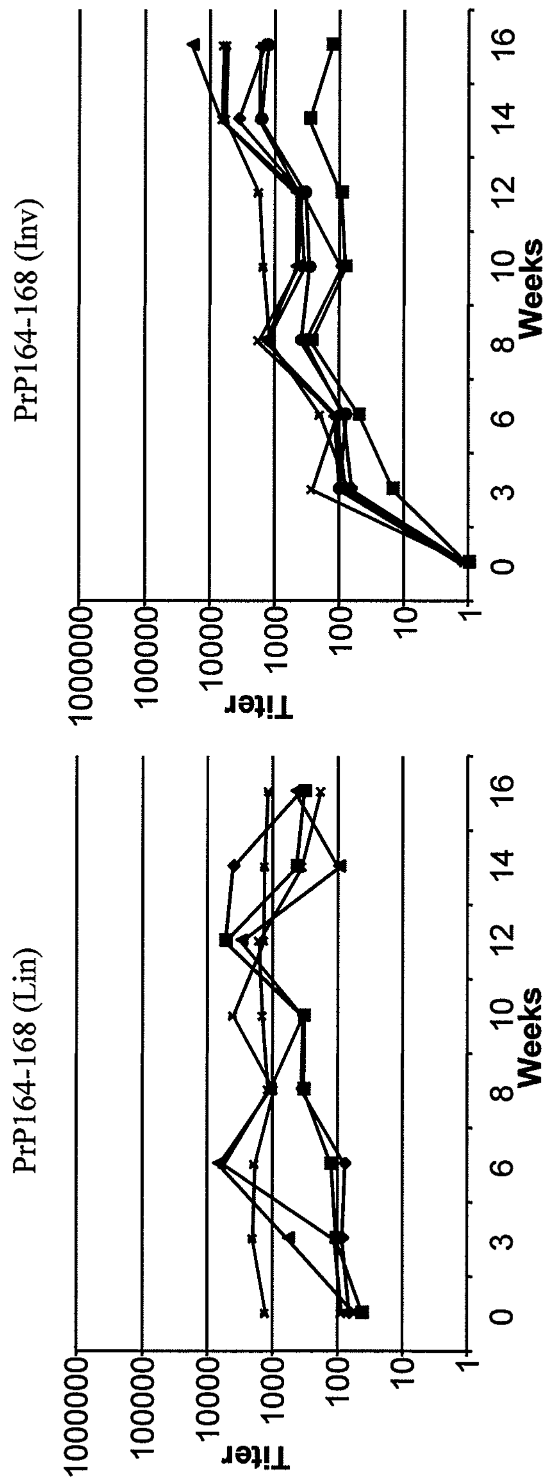
Figures 12E, 12F:
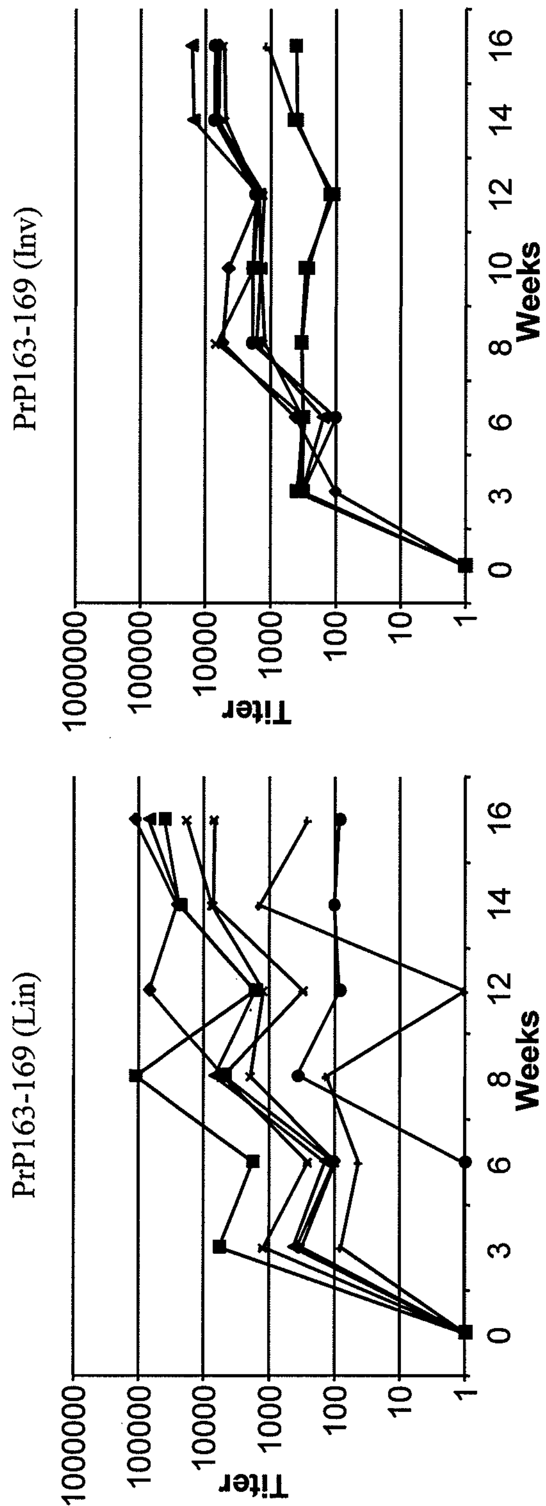
Figure 12H:
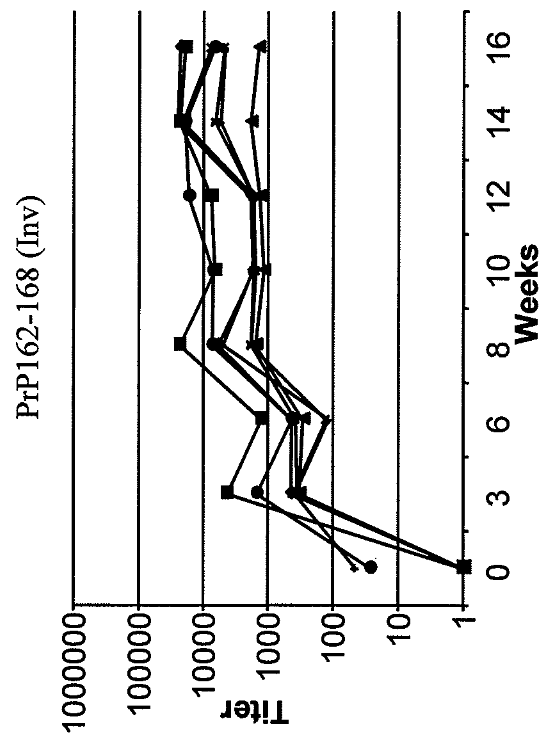
Figure 12G:
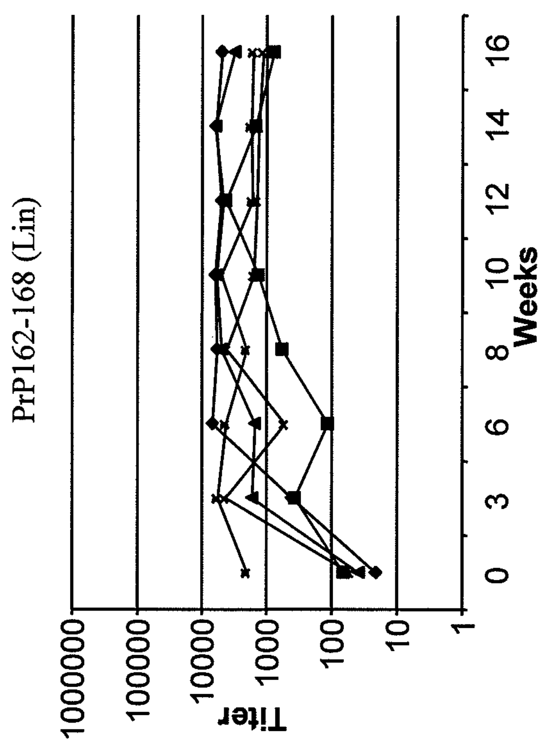
Figure 12I:
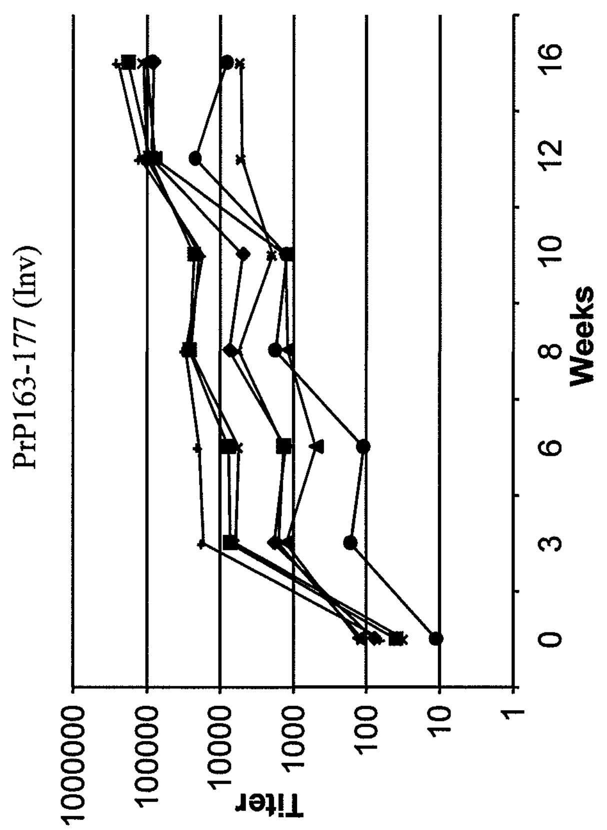

A. Construction and Purification of Lkt Constructs:

Genes expressing the desired YYR-based antigens were synthesized by Codon Devices (Cambridge, Mass.) and BioBasic (Markham, ON) and provided in a generic pUC plasmid. The appropriate fragments were removed via restriction digestion with BamHI and NcoI (New England BioLabs, Ipswich, Mass.) and ligated into the plasmid pAA352 as described in U.S. Pat. Nos. 5,476,657; 5,422,110; 5,723,129 and 5,837,268, incorporated herein by reference in their entireties. Plasmid pAA352 is depicted in FIG. 10 and expresses LKT 352, the sequence of which is depicted in FIG. 11. LKT 352 is derived from the lktA gene of *Pasteurella haemolytica* leukotoxin and is a truncated leukotoxin molecule, having 914 amino acids and an estimated molecular weight of around 99 kDa, which lacks the cytotoxic portion of the molecule.

Antigens were expressed as C-terminal fusions of the Lkt protein. A series of plasmid constructs were created representing different expansions of the YYR epitope as well as different presentations of the antigens as either linear or inverted repeats. The various constructs and the designed names (SN1 through SN8) are presented in Table 1. All plasmids were sequenced to ensure the fidelity of sequence and reading frame.

Chimeric LktA expression vectors were transformed into BL21(DE3) followed by growth and IPTG induction by standard protocols. The recombinant proteins were produced as inclusion bodies. The solubilized protein was then purified under denaturing conditions using HIS-BIND Resin columns (Novagen, Mississauga, ON). The isolated protein was determined to be approximately 85% pure, which is of sufficient purity for immunization trials.

The presence of the incorporated epitopes on the Lkt proteins was confirmed through Western blot analysis employing a monoclonal antibody specific to the engineered poly-histidine groups (Qiagen, Mississauga, ON). A reactive band of the appropriate molecular weight was observed for each SN constructs and the Lkt control did not produce a reactive species.

TABLE 1

Antigen Sequences and Orientation of Constructs

| Construct | Formal Name | Antigen | Presentation | Sequence |
|---|---|---|---|---|
| SN1 | PrP165-167 (Lin) | YYR | $(\rightarrow\rightarrow)_4$ | YYRYYRYYRYYRYYRYYRYYRYYR (SEQ ID NO: 25) |
| SN2 | PrP165-167 (Inv) | YYR | $(\rightarrow\leftarrow\leftarrow)_4$ | YYRRYYRYYYYRRYYRYYYYRRYY RYYYYRRYYRYY (SEQ ID NO: 26) |
| SN3 | PrP164-168 (Lin) | VYYRP (SEQ ID NO: 10) | $(\rightarrow\rightarrow)_4$ | VYYRPVYYRPVYYRPVYYRVVYYRP VYYRPVYYRPVYYRP (SEQ ID NO: 27) |
| SN4 | PrP164-168 (Inv) | VYYRP (SEQ ID NO: 10) | $(\rightarrow\leftarrow\leftarrow)_4$ | VYYRPPRYYVPRYYVVYYRPPRYYV PRYYVVYYRPPRYYVPRYYVVYYRP PRYYVPRYYV (SEQ ID NO: 28) |
| SN5 | PrP163-169 (Lin) | QVYYRPV (SEQ ID NO: 13) | $(\rightarrow\rightarrow)_4$ | QVYYRPVQVYYRPVQVYYRPVQVY YRPVQVYYRPVQVYYRPVQVYYRP VQVYYRPV (SEQ ID NO: 29) |
| SN6 | PrP163-169 (Inv) | QVYYRPV (SEQ ID NO: 13) | $(\rightarrow\leftarrow\leftarrow)_4$ | QVYYRPVVPRYYVQVPRYYVQQVY YRPVVPRYYVQVPRYYVQQVYYRP VVPRYYVQVPRYYVQQVYYRPVVP RYYVQVPRYYVQ (SEQ ID NO: 30) |
| SN7 | PrP162-168 (Lin) | NQVYYRP (SEQ ID NO: 15) | $(\rightarrow\rightarrow)_4$ | NQVYYRPNQVYYRPNQVYYRPNQV YYRPNQVYYRPNQVYYRPNQVYYR PNQVYYRP (SEQ ID NO: 31) |
| SN8 | PrP162-168 (Inv) | NQVYYRP (SEQ ID NO: 15) | $(\rightarrow\leftarrow\leftarrow)_4$ | NQVYYRPPRYYVQNPRYYVQNNQV YYRPPRYYVQNPRYYVQNNQVYYR PPRYYVQNPRYYVQNNQVYYRPPR YYVQNPRYYVQN (SEQ ID NO: 32) |

TABLE 1-continued

Antigen Sequences and Orientation of Constructs

| Construct | Formal Name | Antigen | Presentation | Sequence |
|---|---|---|---|---|
| SN6b | PrP163-177 (Inv) | QVYYRPV DQYSNQN (SEQ ID NO: 35) | (→←←)$_4$ | QVYYRPVDQYSNQNNQNSYQDVPR YYVQNQNSYQDVPRYYVQQVYYRP VDQYSNQNNQNSYQDVPRYYVQNQ NSYQDVPRYYVQQVYYRPVDQYSN QNNQNSYQDVPRYYVQNQNSYQDV PRYYVQQVYYRPVDQYSNQNNQNS YQDVPRYYVQNQNSYQDVPRYYVQ (SEQ ID NO: 36) |

B. Formulation and Delivery:

For sheep, animals were immunized subcutaneously (s.c) with varying concentrations of the Lkt fusion constructs in 650 μL of PBS (0.188M $Na_2HPO_4$, 0.012M $NaH_2PO_4$, 1.8% NaCl, pH 7.8) with 30% EMULSIGEN PLUS, an oil-in-water emulsion comprising a light mineral oil as well as 0.05% formalin, and 30 μg/mL gentamicin as preservatives, available from MVP Laboratories, Ralston, Nebr. Vaccines were administered at six week intervals.

Balb/c mice were immunized s.c with 10 μg, of either Lkt or keyhole limpet hemocyanin (KLH) constructs, and were brought to a final volume of 50 μl with PBS. The adjuvant consisted of EMULSIGEN PLUS. Mice were immunized at three week intervals.

C. Peptide Synthesis:

All peptides were chemically synthesized on a Pioneer solid-phase peptide synthesizer (PerSeptive Biosystems, Foster City, Calif.) using Fmoc (9-fluorenylmethoxy carbonyl) chemistry. The peptide chains were synthesized from the carboxyl terminus to the amino terminus onto [5-(4-Fmoc-aminomethyl-3,5-dimethyloxyphenoxy) valeric acid]-polyethylene glycol-polystyrene (PAL-PEG-PS) resin. Fmoc-protecting groups at the amino terminus were deprotected with piperidine. The peptides were cleaved from the resin with concurrent deprotection of the side chain-protecting groups by treating the resin-bound peptide with trifluoroacetic acid (TFA) (9.3 parts) in the presence of scavengers (anisole-ethyl-methyl sulfide-1,2-ethanedithiol[3:3:1]), for 7 h. The crude peptides were filtered from the resin, and the TFA was evaporated. Diethyl ether was added to the residues to precipitate the crude peptide. The peptides were isolated and purified by high-performance liquid chromatography (HPLC) on Vydac protein $C_4$ columns (1.0 by 25 cm) eluting with a linear gradient of 10% buffer A ($H_2O$-0.1% TFA)-90% buffer B (acetonitrile-$H_2O$ [90/10]-0.01% TFA) for 40 min at a flow rate of 3 ml/minute. The purity and molecular weight of the respective peptides were confirmed by matrix-assisted laser desorption ionization (MALDI)-time of flight mass spectrometry on a PE Biosystems Voyager system 4068 (National Research Council, Plant Biotechnology Institute, Saskatoon, Canada) and by amino acid analysis.

D. ELISAs:

In order to assess the specificity of the Ab responses for the particular antigens, 96-well polystyrene microtiter plates (Immulon 2, Dynatech, Gaithersburg, Md.) were coated overnight with 0.5 μg per well of the corresponding peptide that was expressed as the Lkt fusion. Plates were washed six times with distilled water ($dH_20$) then blocked with 200 μL per well of TBST (TBS: Tris-buffered saline, 10 mmol/L Tris, 150 mmol/L NaCl, 0.05% TWEEN 20) and 1% skim milk. Plates were incubated for one hour at room temperature and then washed 6 times in $dH_20$, Serum samples were diluted 1:10 in TBST with 1% skim milk and then serially diluted 1:4 in TBST plus 1% skim milk. Plates were incubated for 2 h and then washed 6 times with $dH_20$. 100 μL of Alkaline phosphatase (AP)-conjugated rabbit anti-sheep IgG or AP-conjugated goat anti-mouse IgG (from Kirkgaard and Perry Laboratories, Gaithersburg, Md.) diluted to 1:2500 were added to each well to detect bound ovine and murine Ab, respectively. After a 1 h incubation, plates were washed 6 times with $dH_20$. 100 μL of p-nitrophenyl phosphate PNNP (Sigma, Oakville ON,) was added to each well and incubated for 2 h. ELISA titers were expressed as the reciprocal of the highest dilution resulting in a reading of two standard deviations above the value of a negative control serum.

E. Immunoprecipitation of $PrP^{Sc}$

Antisera from sheep immunized with SN3, SN4 or SN8 were evaluated for the ability to recognize $PrP^{Sc}$. Antibodies conjugated to magnetic beads were used in immunoprecipitation assays of brain homogenates of uninfected hamsters and 263K scrapie infected hamsters.

Example 1

Immunization of Mice with LKt-YYR

To facilitate a direct comparison of the Lkt carrier with more traditional peptide antigen delivery systems, mice (n=10) were immunized with 10 μg of the YYR peptide antigen either chemically conjugated to KLH or expressed as a C-terminal fusion of Lkt in 30% EMULSIGEN PLUS. Immunizations were performed on a 4 week interval and antibodies were determined through peptide ELISAs to the SN1 peptide bi-weekly.

Figure 2B:
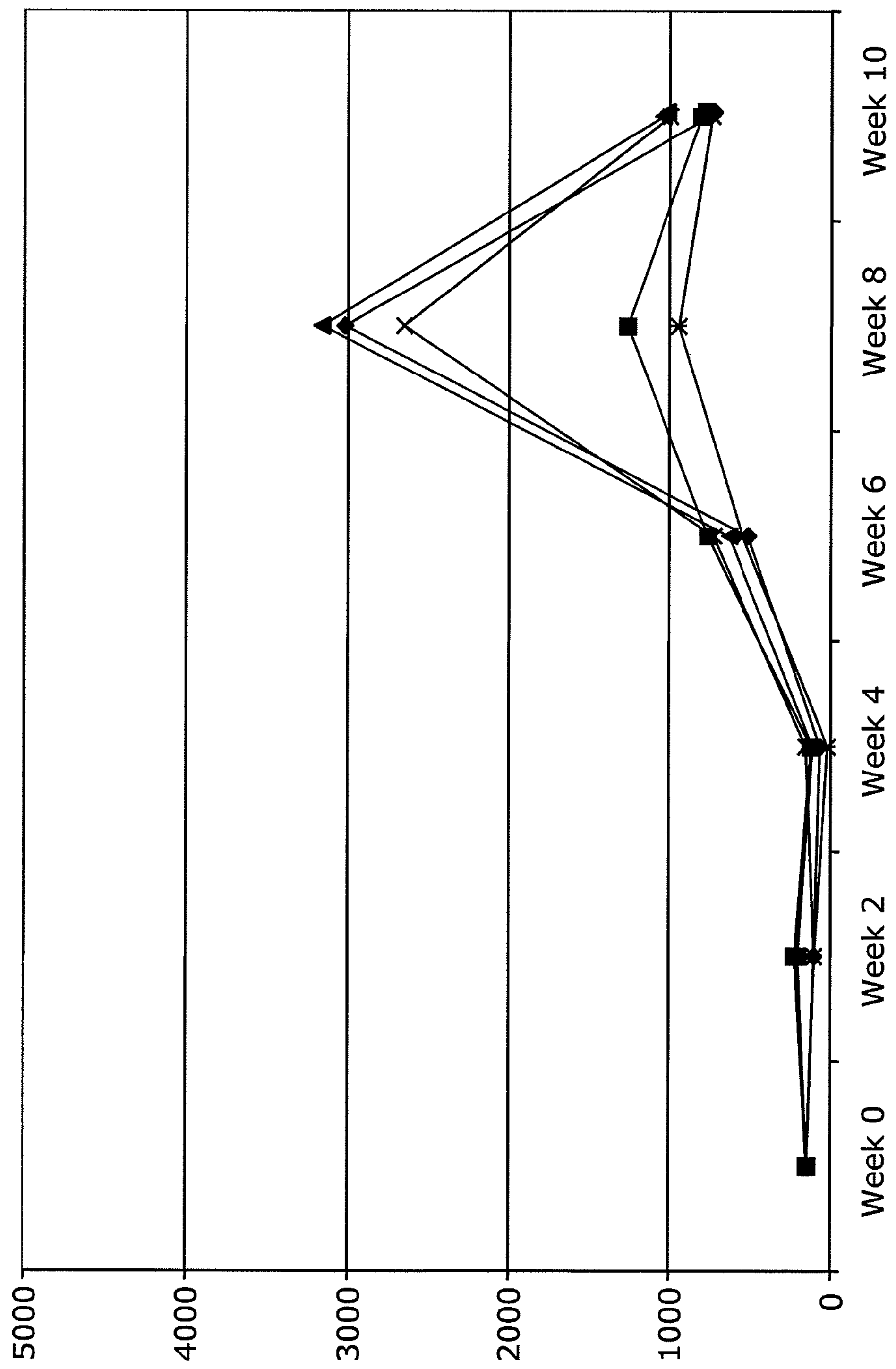

Consistent with previous reports, using traditional delivery strategies, the YYR peptide was weakly immunogenic with none of the animals achieving titers over a thousand even after three immunizations (FIG. 2A). In contrast to the limited immunogenicity with the KLH carrier, the Lkt fusion constructs generated significantly higher responses in all of the animals verifying the value of this delivery system for inducing immune responses against this particular antigen (FIG. 2B).

Example 2

Immunization of Sheep with LKt-YYR

As immunological responses to particular epitopes are often species-specific the ability for the Lkt-YYR construct to induce antibody responses in sheep was evaluated. This is a relevant species for a prion vaccine and also introduces the obstacle of genetic variability as outbred populations of animals, such as sheep, are typically variable in their immunological responses. Sheep (n=3) were immunized with 200 μg of LKT-SN1 in 30% EMULSIGEN PLUS. Immunizations were performed on a 6 week interval and antibodies were determined through peptide ELISAs to the SN1 peptide bi-weekly.

Figure 3A:
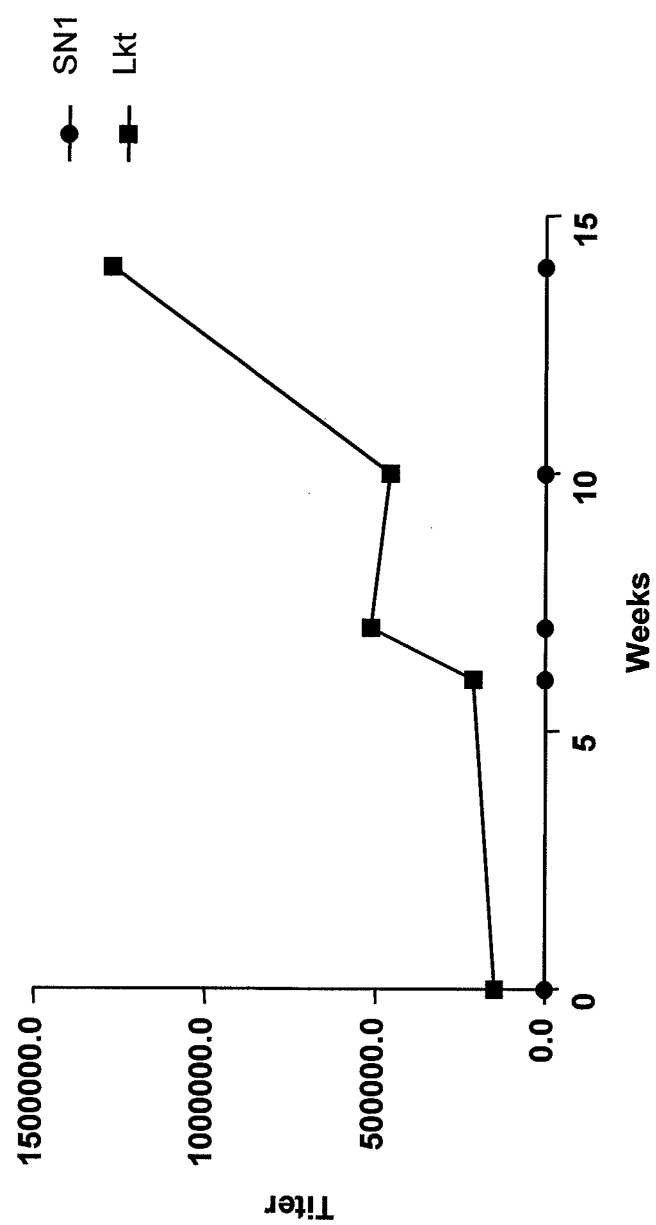
FIGS. 3A and 3B show the antibody titers in sheep immunized with Lkt-SN1.
Figure 3B:
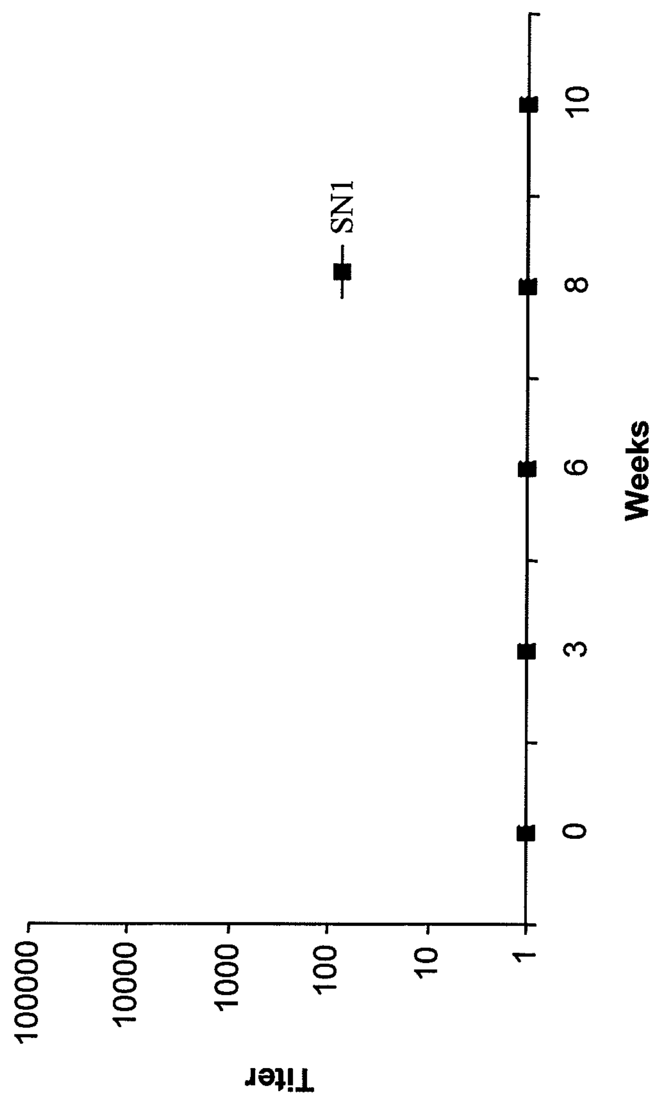
Figure 4A:
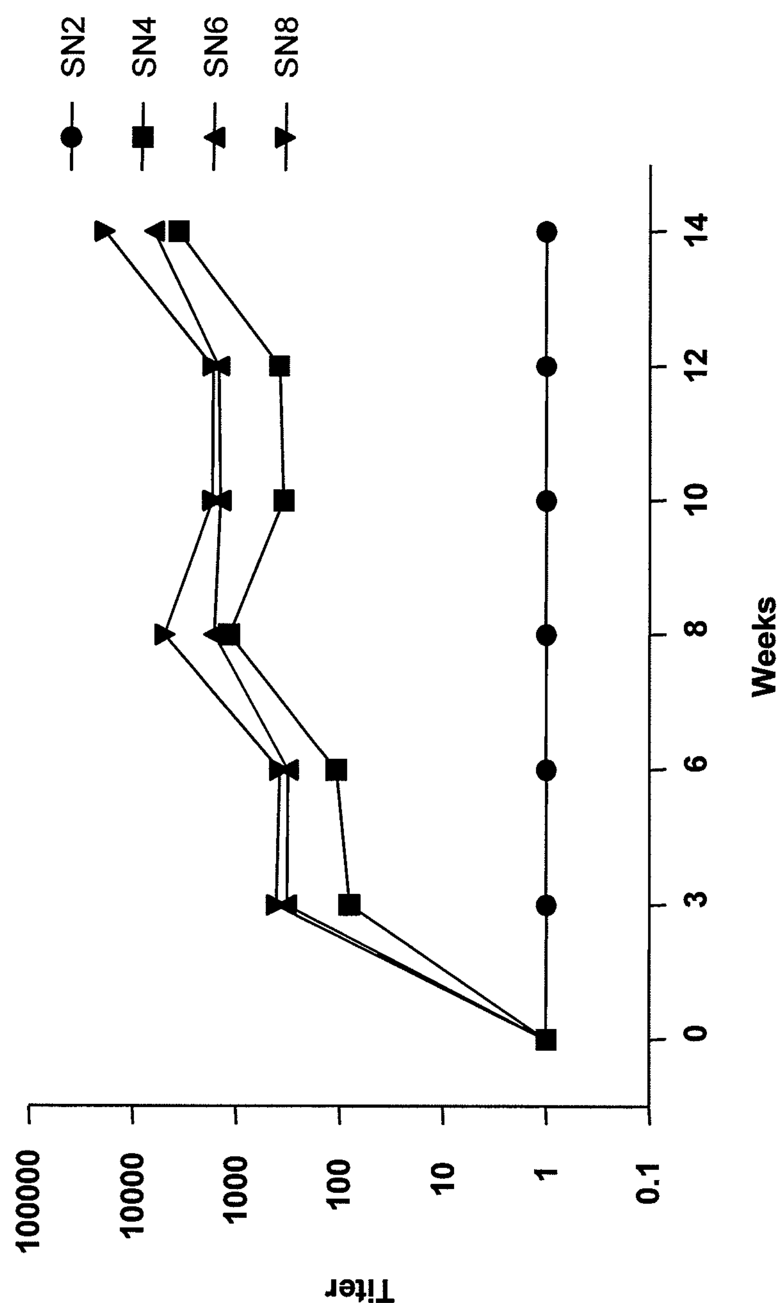
FIGS. 4A-4E show antibody titers in sheep immunized with expanded YYR epitopes.
Figure 4C:
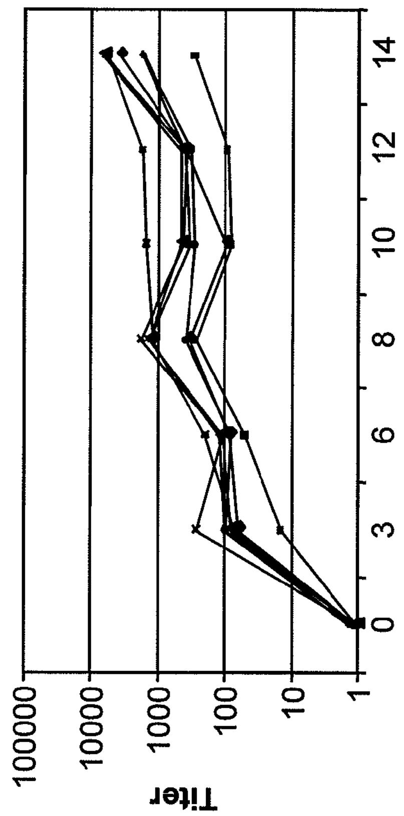
Figure 4E:
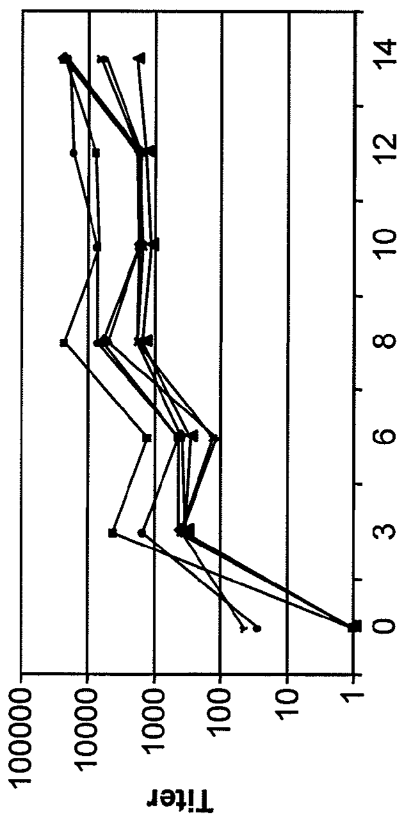
Figure 4B:
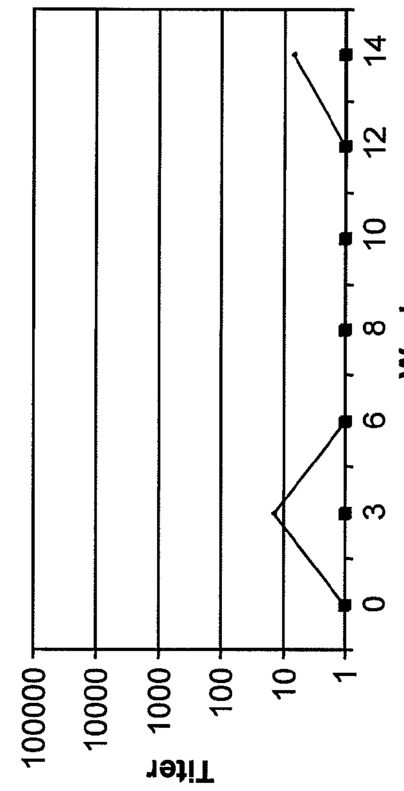
Figure 4D:
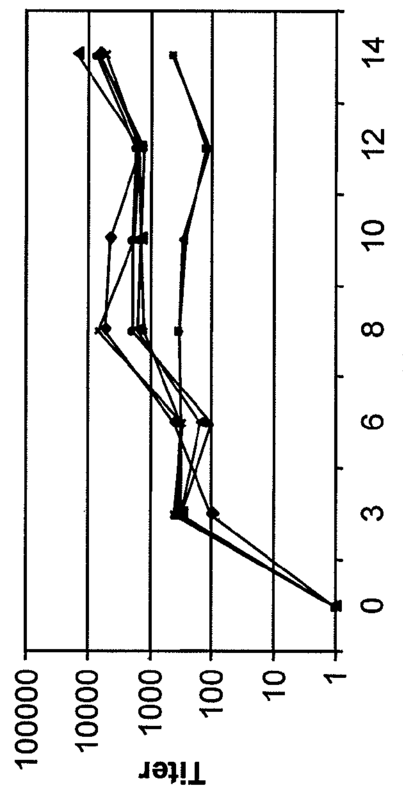

In contrast to the responses which were observed in mice, the Lkt-YYR constructs failed to induce any measurable YYR-specific antibodies in sheep even after three immunizations (FIGS. 3A and 3B). This was not a consequence of an absence of an immune response against the carrier as strong antibody responses against Lkt were observed in all animals (FIG. 3A). This indicates that the limited immunogenicity of the YYR epitope prevent its utilization as a vaccine target in sheep and likely other ruminants. This also demonstrates that the Lkt carrier alone is insufficient to overcome the limited immunogenicity of the YYR epitope and that additional measures of epitope optimization are required.

Example 3

Expansion of the YYR Epitope

In order to evaluate whether the immunogenicity of the YYR epitope in sheep could be enhanced, various expanded epitopes were synthesized with the sequences and orientations shown in Table 1. Expansion of the YYR epitope was done through symmetrical additions to both the amino and carboxy termini of the YYR epitope, to generate the five amino acid epitopes VYYRP (SEQ ID NO:10) and QVYYRPV (SEQ ID NO:13), respectively. Additional constructs with seven and fourteen residue cores were generated through asymmetrical expansion of the YYR epitope based on consideration of the crystallographic structure of $PrP^{C}$. While the tendency for the $PrP^{Sc}$ isoform to aggregate in insoluble fibers which are not amenable for structural investigations prevents direct observation of epitopes uniquely exposed in $PrP^{Sc}$ it is nevertheless possible to use the structure of $PrP^{C}$ to identify regions of the protein which are sequestered away from the surface and antibody recognition. Specifically, it was determined that asymmetrical expansion towards the N-terminus would provide an epitope which would be sequestered in the non-infectious conformation of the protein to minimize the likelihood of cross-reactivity of the antibodies generated with $PrP^{C}$.

Example 4

Immunization of Sheep with Expanded Epitopes

Lkt-YYR, as well as each of the expanded epitope constructs presented as inverted repeats (SN2, SN4, SN6 and SN8) were identically formulated (50 μg protein in 30% EMULSIGEN PLUS) and used to immunize sheep (n=7) at six week intervals. Antibody titers were determined using peptide ELISAs bi-weekly.

Consistent with the earlier results, the YYR-based vaccine failed to induce antibody responses in any of the animals, again verifying that even with optimized formulation and delivery the YYR epitope is not immunogenic in sheep (FIG. 4). For each of the expanded epitopes, increased antibody responses were observed after the primary immunization as well as each of the following two boosts (FIG. 4). The non-symmetrical SN8 expansion displayed the most immunogenicity of the constructs considered. The expanded epitopes appeared to elicit relatively sustained responses in that no significant decline in titers was observed between the immunizations.

Figure 13:
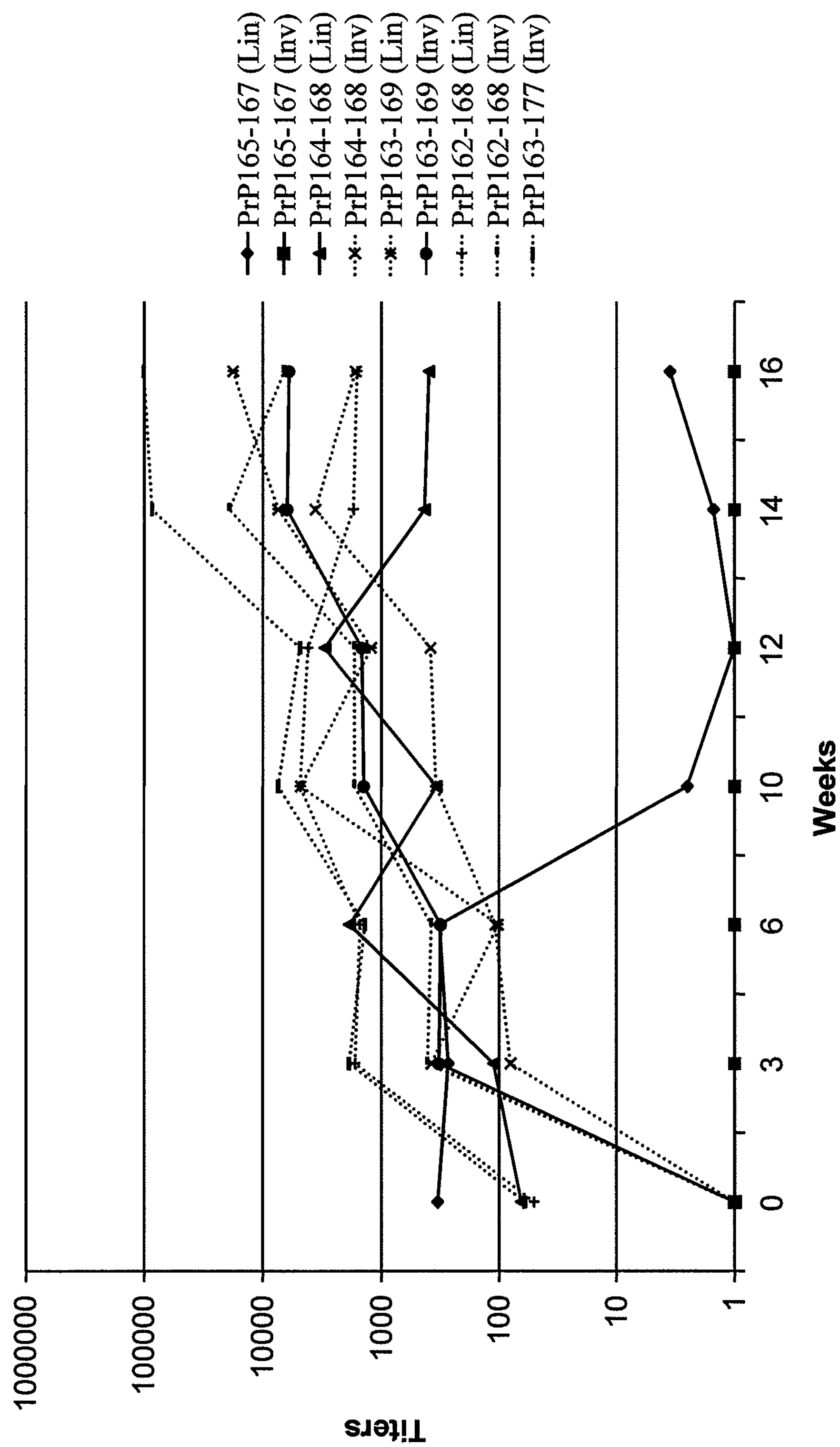
FIG. 13 shows the median antibody titers in sheep immunized with PrP165-167 (Lin) (SN1); PrP165-167 (Inv) (SN2); PrP164-168 (Lin) (SN3); PrP164-168 (Inv) (SN4); PrP163-169 (Lin) (SN5); PrP163-169 (Inv) (SN6); PrP162-168 (Lin) (SN7); PrP162-168 (Inv) (SN8); and PrP162-177 (Inv) (SN6b).

In an additional experiment, constructs SN1, SN2, SN3, SN4, SN5, SN6, SN7, SN8 and SN6b were used to immunize groups of 7 sheep and titers determined as above. FIG. 12 shows individual results and FIG. 13 shows the median titers at week 16 which were 3.5 for SN1; 0 for SN2; 391 for SN3; 1592 for SN4; 17709 for SN5; 6638 for SN6; 1592 for SN7; 6638 for SN8 and 100598 for SN6b. Consistent with those results above, the expanded epitopes showed enhanced immunogenicity, with the SN6b expansion displaying the most immunogenicity.

Example 5

Optimization of Vaccine Dose

The development of a vaccine that induces consistent immune responses is often problematic, particularly for outbred populations such as sheep and cattle and typically requires considerable effort to optimize the formulation and consideration of various adjuvants. The efficacy of the Lkt is dose-dependent in a species-specific fashion.

A dose titration of the SN4 construct was performed in sheep to determine the optimal dose for maximal antibody response. Sheep (n=5) were immunized with Lkt-SN4 concentrations indicated in FIG. 5 in 30% EMULSIGEN PLUS. Immunizations were performed on a 6 week interval and titers were determined using bi-weekly peptide ELISAs.

Figure 5:
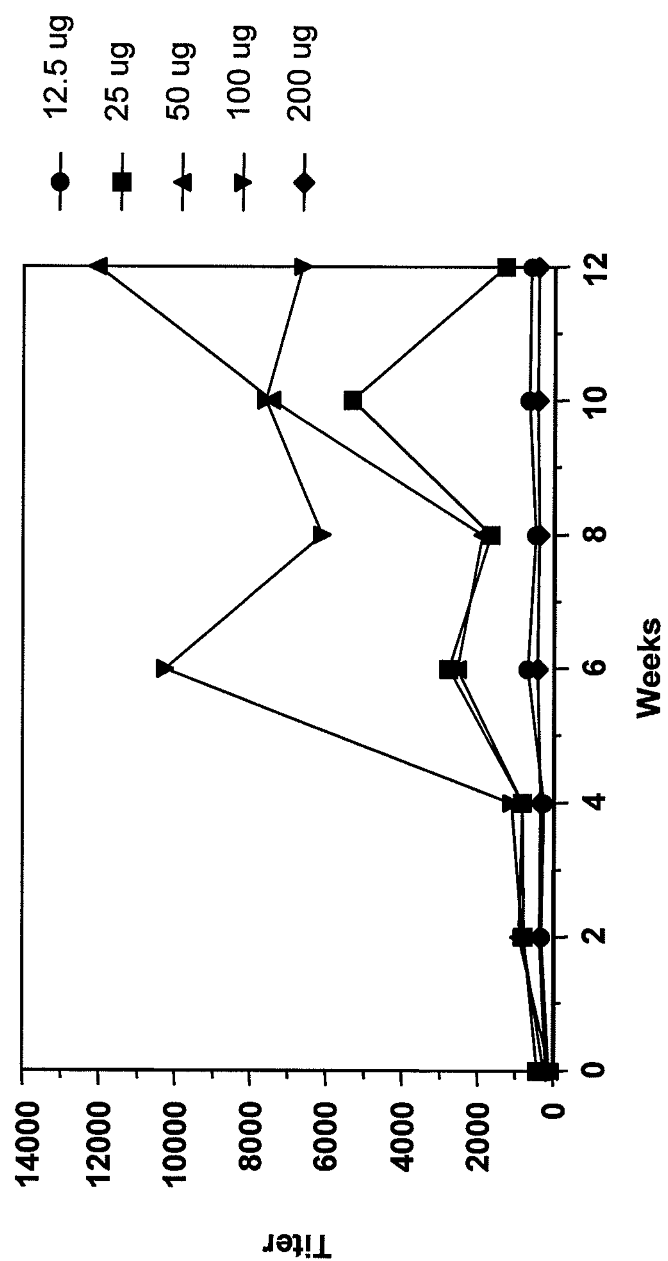
FIG. 5 shows the antibody titers in sheep immunized with the indicated concentrations of Lkt-SN4 in 30% EMULSIGEN PLUS.

As shown in FIG. 5, the highest and lowest doses tested, 12.5 and 200 μg, resulted in the lowest antibody titers while the 50 μg dose was found to give an optimal response.

Example 6

Reactivity of Antibodies with Expanded Epitopes with $PrP^{c}$

Figure 6:
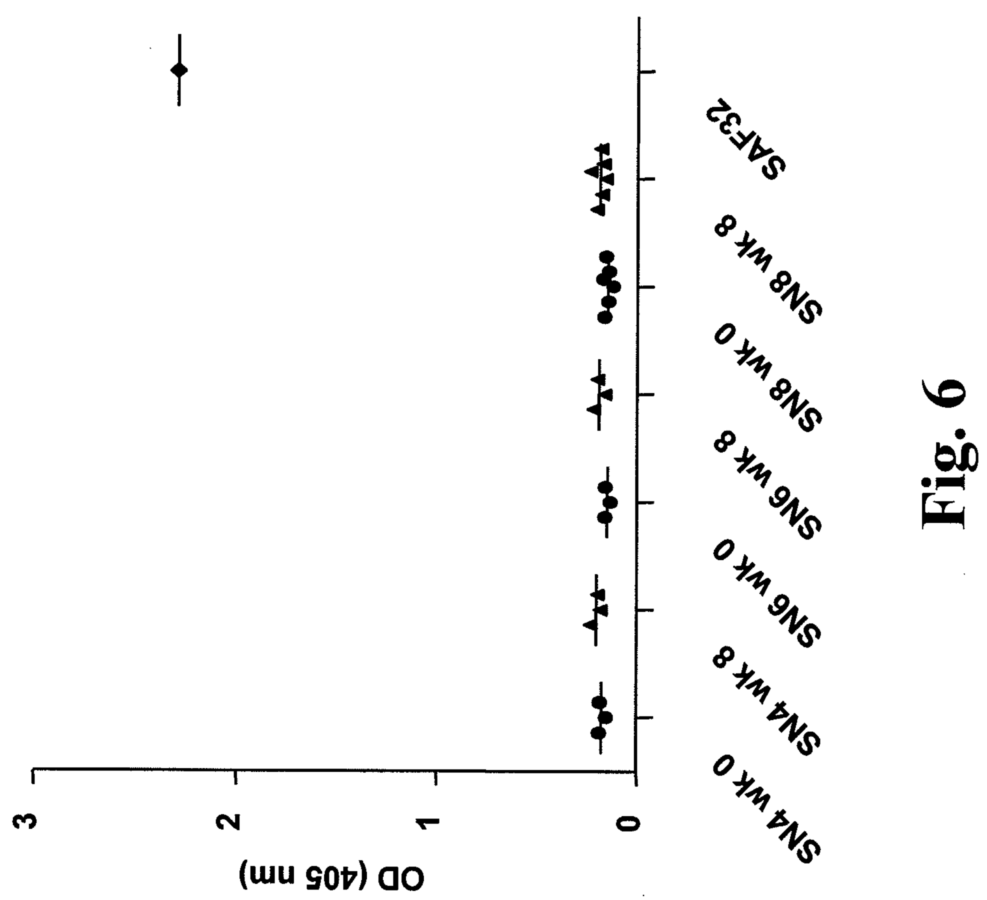
FIG. 6 shows the reactivity of sera from sheep immunized with SN4, SN6 and SN8 with $PrP^c$. Each triangle represents an individual animal.

While expansion of the YYR epitope overcomes the limitation of immunogenicity, it is essential to ensure that the corresponding antibodies retain the ability to discriminate $PrP^{Sc}$ from $PrP^{C}$. To investigate this, high titer sera from sheep immunized with SN4, SN6 or SN8, as well as the corresponding pre-immune serum, was evaluated through ELISAs for reactivity against recombinant $PrP^{C}$. As shown in FIG. 6, no reactivity with $PrP^{C}$ was observed with each of the constructs.

Example 7

Reactivity of Antibodies with Expanded Epitopes with $PrP^{Sc}$

Figure 7:
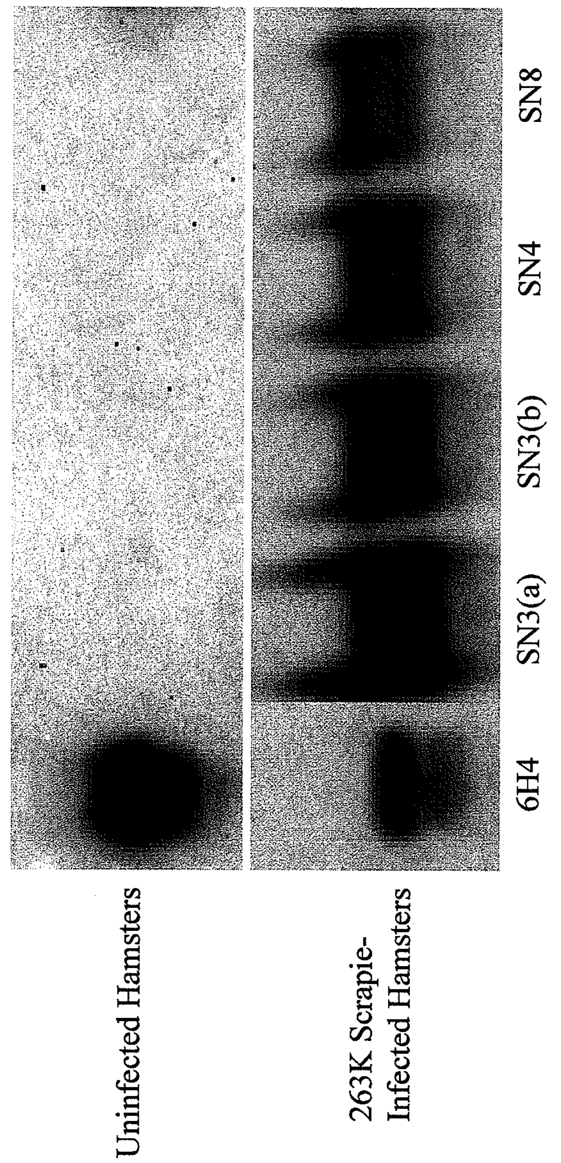
FIG. 7 shows the reactivity of sera from sheep immunized with SN3, SN4 or SN8 with $PrP^{Sc}$. SN3a and SN3b refer to antibodies purified from two different animals immunized with SN3.

In addition to ensuring that antibodies against the expanded epitopes do not cross-react with $PrP^{C}$ it is also essential to demonstrate their ability to bind the misfolded conformation of the protein. Antisera from sheep immunized with SN3, SN4 or SN8 were evaluated for the ability to recognize $PrP^{Sc}$. Antibodies conjugated to magnetic beads were used in immunoprecipitation assays of brain homogenates of uninfected or scrapie 263-infected hamsters. As shown in FIG. 7, sera from the SN3, SN4 and SN8 constructs effectively immunoprecipitated $PrP^{Sc}$. SN3a and SN3b refer to antibodies purified from two different animals immunized with SN3. Notably no cross-reactivity with $PrP^{C}$ was observed from the homogenates of the uninfected animals verifying that the antibodies do not react with $PrP^{C}$.

Figure 14:
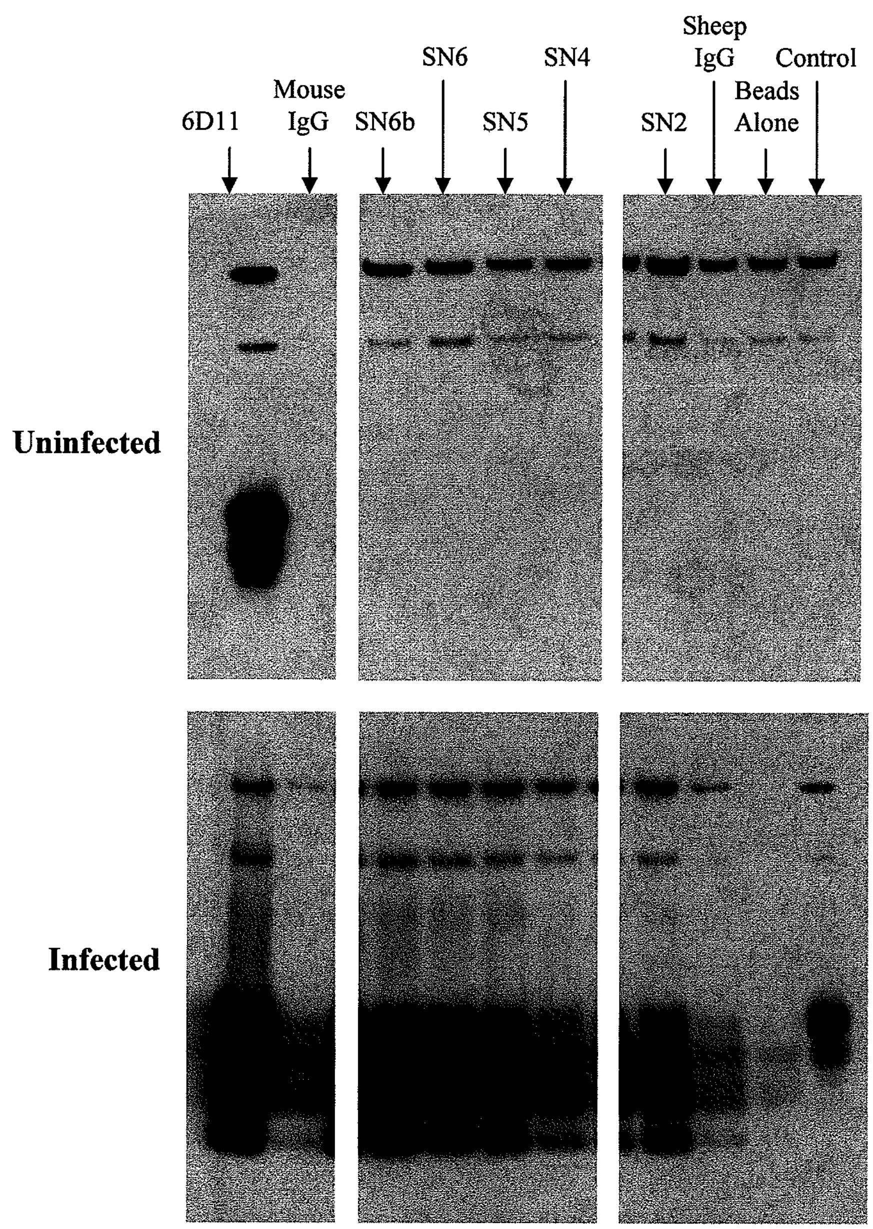
FIG. 14 shows the reactivity of sera from sheep immunized with SN2, SN4, SN5, SN6 or SN6b with $PrP^{Sc}$.

Similarly, antisera from sheep immunized with SN2, SN4, SN5, SN6 and SN6b were evaluated for the ability to recognize $PrP^{Sc}$ as described above. As shown in FIG. 14, sera from all of these constructs effectively immunoprecipitated $PrP^{Sc}$ while no cross-reactivity with $PrP^{C}$ was observed from the homogenates of the uninfected animals.

Example 8

Reactivity of Antibodies to SN8 with YYR Peptides

Figure 8:
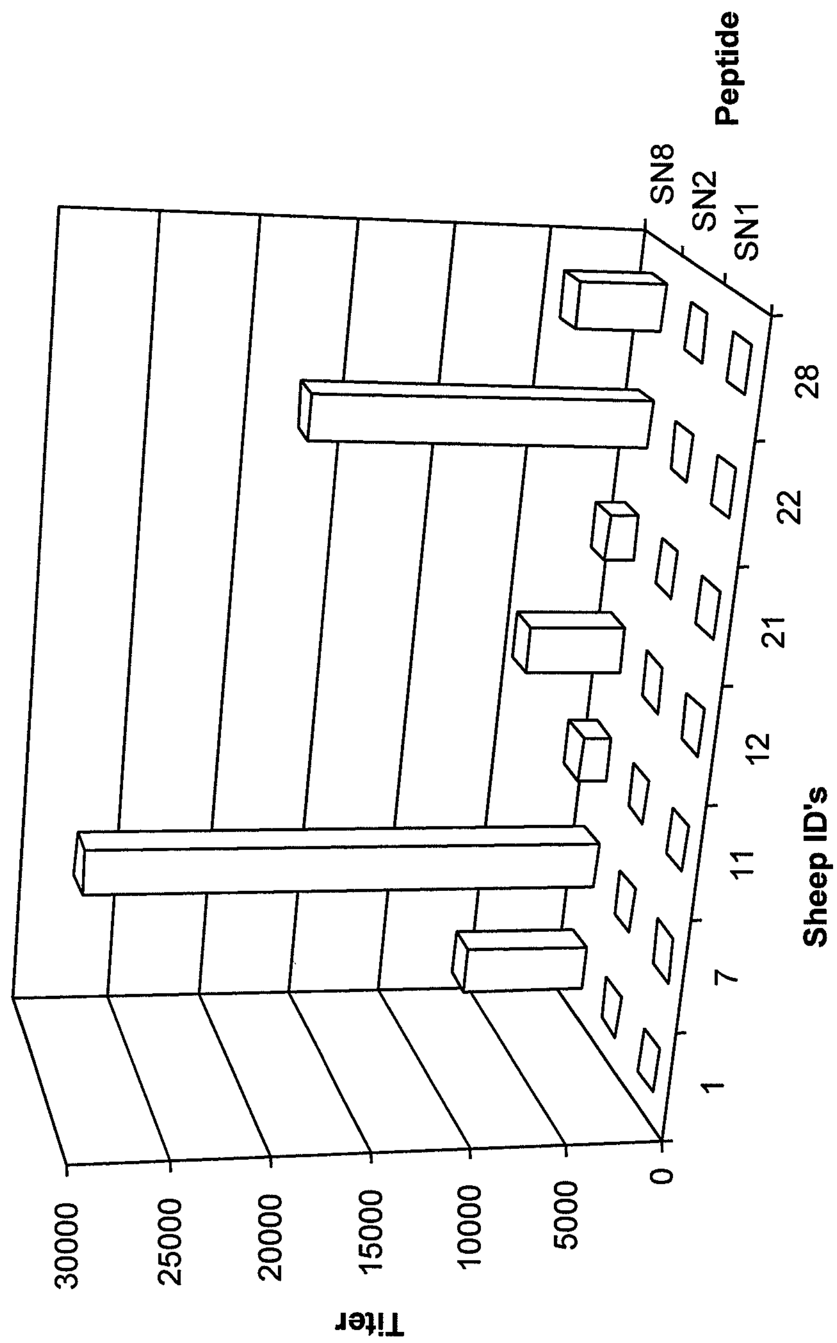
FIG. 8 shows the reactivity of serum from sheep immunized with SN8 with SN1, SN2 and SN8.

In order to determine whether the antibodies raised to the SN8 expanded epitope cross-reacted with YYR unexpanded peptides, sheep (n=7) were immunized with 50 μg of Lkt-SN8 in 30% EMULSIGEN PLUS. Immunizations were performed on a 6 week interval. High titer sera from week 8 were examined using peptide ELISAs against peptides SN1, SN2 and SN8. As shown in FIG. 8, serum from sheep immunized with SN8 did not cross-react with the unexpanded YYR peptides.

Example 9

Lkt Carrier does not Break Tolerance Against $PrP^{C}$

Figure 9:
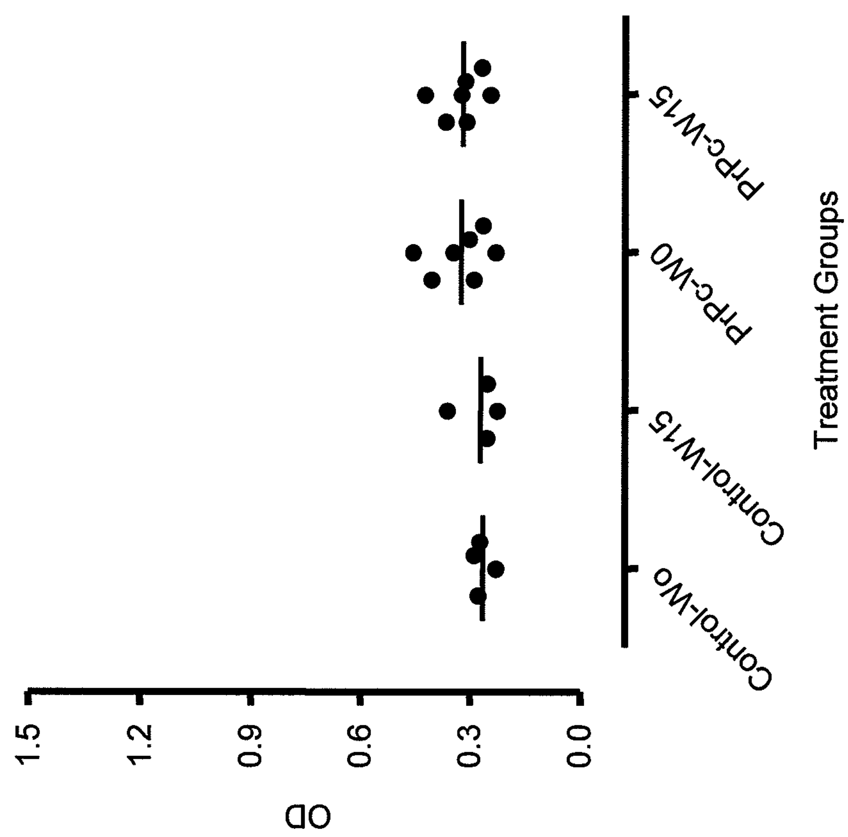
FIG. 9 shows the results of an experiment demonstrating that the Lkt carrier does not break tolerance against $PrP^c$.

In inducing and maintaining antibody responses which are specific to a particular conformation of a self-protein, it is essential that epitope spreading not occur such that the animal breaks tolerance against the protein. To investigate the potential of the Lkt carrier to break tolerance against $PrP^{C}$ a recombinant fusion of the carrier with the full length $PrP^{C}$ was created and administered for three immunizations. In particular, scrapie-susceptible sheep were immunized with either the Lkt carrier (n=4) or Lkt-$PrP^{C}$ (n=7) at 6 week intervals. Immune responses against $PrP^{C}$ were determined using ELISA using recombinant $PrP^{C}$ protein for the pre-immune serum. Serum was collected two weeks after the third immunization. As shown in FIG. 9, no increase in antibody titers against recombinant $PrP^{C}$ was observed as compared to animals which were immunized with the Lkt carrier alone. The inability of the carrier to break tolerance against $PrP^{C}$, even using the full-length molecule as an antigen, supports its safety.

Prion diseases represent a novel form of infectivity whereby the infectious agent is the misfolded conformation of a self-protein. This novel form of infectivity is not recognized by the immune system which allows for unfettered progression of the disease within the host once the misfolding cascade has been initiated. To date antibody responses have not been able to discriminate the normal and infectious forms of the protein.

The YYR epitope has limited immunogenicity. Here through expansion of the epitope, we demonstrate that it is possible to induce robust responses against antigens of self protein that retain their specificity both in the sense of discrimination of different conformations of the protein but also in that epitope spreading to the remainder of the protein does not occur.

This is a significant finding for the production of vaccines against prion diseases. Importantly, as the expanded epitopes described above are conserved across a wide range of biologically relevant species including cattle, sheep, elk, deer and humans, this vaccine is expected to have application for various prion diseases, including without limitation, BSE, scrapie, chronic wasting disease and various forms of both inherited as well as contracted human prion diseases.

As the misfolding of self-proteins is the basis for a variety of other diseases including ALS, Alzheimers and Parkinson's, this strategy for induction of immune responses against cryptic epitopes may have broader applications in the immunotherapy of protein misfolding diseases.

Thus, the present application describes prion expanded epitopes as well as methods of use thereof. Although preferred embodiments of the subject invention have been described in some detail, it is understood that obvious variations can be made without departing from the spirit and the scope of the invention as defined by the appended claims.

The invention claimed is:

1. An isolated immunogenic peptide comprising three or more fused repeats of the amino acid sequence QVYYRPVDQYSNQN (SEQ ID NO:35), wherein one or more of the three repeats is in an inverted orientation.

2. The immunogenic peptide of claim 1, wherein said peptide comprises the amino acid sequence of SEQ ID NO:36.

3. The immunogenic peptide of claim 1, linked to a carrier molecule.

4. The immunogenic peptide of claim 3, wherein the carrier molecule is capable of enhancing the immunogenicity of the immunogenic peptide.

5. The immunogenic peptide of claim 3, wherein the carrier molecule is a leukotoxin polypeptide.

6. The immunogenic peptide of claim 5, wherein the leukotoxin polypeptide is LKT 352.

7. A composition comprising the immunogenic peptide of claim 1 and a pharmaceutically acceptable vehicle.

8. A method of producing a composition comprising combining the immunogenic peptide of claim 1 with a pharmaceutically acceptable vehicle.

9. A method of eliciting an immune response to a prion in a mammal comprising administering to said mammal an immunologically effective amount of the composition of claim 7.

10. A method of detecting presence or absence of prion antibodies in a biological sample comprising:

(a) providing a biological sample;

(b) reacting said biological sample with an immunogenic peptide according to claim 1 under conditions which allow prion antibodies, when present in the biological sample, to bind specifically to said immunogenic peptide to form an antibody-antigen complex; and (c) detecting the presence or the absence of said complex, thereby detecting the presence or the absence of the prion antibodies in said sample.

11. An immunodiagnostic test kit for detecting prion infection, said test kit comprising the immunogenic peptide of claim 1, and instructions for conducting an immunodiagnostic test.

12. The immunogenic peptide of claim 2, linked to a carrier molecule.

13. The immunogenic peptide of claim 12, wherein the carrier molecule is capable of enhancing the immunogenicity of the immunogenic peptide.

14. The immunogenic peptide of claim 12, wherein the carrier molecule is a leukotoxin polypeptide.

15. The immunogenic peptide of claim 14, wherein the leukotoxin polypeptide is LKT 352.

16. A composition comprising the immunogenic peptide of claim 2 and a pharmaceutically acceptable vehicle.

17. A composition comprising the immunogenic peptide of claim 15 and a pharmaceutically acceptable vehicle.

* * * * *